US008124068B2

(12) United States Patent
Horwitz et al.

(10) Patent No.: US 8,124,068 B2
(45) Date of Patent: *Feb. 28, 2012

(54) RECOMBINANT INTRACELLULAR PATHOGEN IMMUNOGENIC COMPOSITIONS AND METHODS OF USE

(75) Inventors: Marcus A. Horwitz, Los Angeles, CA (US); Gunter Harth, Los Angeles, CA (US); Michael V. Tullius, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 12/581,795

(22) Filed: Oct. 19, 2009

(65) Prior Publication Data

US 2010/0092518 A1   Apr. 15, 2010

Related U.S. Application Data

(62) Division of application No. 10/595,385, filed as application No. PCT/US2004/034206 on Oct. 15, 2004, now Pat. No. 7,622,107.

(60) Provisional application No. 60/512,565, filed on Oct. 16, 2003.

(51) Int. Cl.
*A01N 63/00* (2006.01)
*A01N 65/00* (2009.01)
*C12N 1/12* (2006.01)
*C12N 1/20* (2006.01)

(52) U.S. Cl. .................. 424/93.1; 424/93.2; 435/252.3; 435/253.1

(58) Field of Classification Search .................. None
See application file for complete search history.

(56) References Cited

U.S. PATENT DOCUMENTS

| | | | |
|---|---|---|---|
| 5,504,005 A | 4/1996 | Bloom et al. | |
| 5,583,038 A | 12/1996 | Stover | |
| 5,591,632 A | 1/1997 | O'Donnell et al. | |
| 5,679,515 A | 10/1997 | Stover et al. | |
| 5,700,683 A | 12/1997 | Stover et al. | |
| 5,736,367 A | 4/1998 | Haun et al. | |
| 5,776,465 A | 7/1998 | O'Donnell et al. | |
| 5,807,723 A | 9/1998 | Aldovini et al. | |
| 5,830,475 A | 11/1998 | Aldovini et al. | |
| 5,854,055 A | 12/1998 | Bloom et al. | |
| 5,866,403 A | 2/1999 | Aldovini et al. | |
| 5,869,057 A | 2/1999 | Rock | |
| 6,015,696 A | 1/2000 | Yamada et al. | |
| 6,471,967 B1 | 10/2002 | Horwitz et al. | |
| 6,924,118 B2 * | 8/2005 | Horwitz et al. | 424/9.1 |
| 7,622,107 B2 * | 11/2009 | Horwitz et al. | 424/93.1 |

FOREIGN PATENT DOCUMENTS

| | | |
|---|---|---|
| EP | 1164488 A | 12/2001 |
| WO | 88/06626 | 9/1988 |
| WO | 98/31388 A | 7/1998 |
| WO | 03/070164 A | 8/2003 |
| WO | 2004/031356 | 4/2004 |

OTHER PUBLICATIONS

Chambers et al. "Identification of a *Mycobacterium bovis* BCG Auxotrophic Mutant that Protects Guinea Pigs against *M. bovis* and Hematogenous Spread of *Mycobacterium tuberculosis* without Sensitization to Tuberculin." Infection and Immunity, Dec. 2000, p. 7094-7099, vol. 68, No. 12.

Smith et al. "Characterization of Auxotrophic Mutants of *Mycobacterium tuberculosis* and Their Potential as Vaccine Candidates." Infection and Immunity, Feb. 2001, p. 1142-1150, vol. 69, No. 2.

Tullius et al. "High Extracellular Levels of *Mycobacterium tuberculosis* Glutamine Synthetase and Superoxide Dismutase in Actively Growing Cultures Are Due to High Expression and Extracellular Stability Rather than to a Protein-Specific Export Mechanism." Infection and Immunity, Oct. 2001, p. 6348-6363, vol. 69, No. 10.

Cirillo et al., "Bacterial Vaccine Vectors and Bacillus Calmette-Guerin", Clinical Infectious Diseases, 20:1001-9 (1995).

Fuerst et al., "Development and Analysis of Recombinant BCG Vector Systems", AIDS Research and Human Retroviruses, 8:1451-5 (1992).

Hanson et al., "Efficacy and Safety of Live Recombinant BCG Vaccines", Dev. Biol. Stand., 84:229-36 (1995).

Harth et al., "High-Level Heterologous Expression and Secretion in Rapidly Growing Nonpathogenic Mycobacteria of Four Major *Mycobacterium tuberculosis* Extracellular Proteins Considered to be Leading Vaccine Candidates and Drug Targets", Infection and Immunity, 65:2321-8 (1997).

Harth et al., "Novel Insights into the Genetics, Biochemistry, and Immunocytochemistry of the 30-Kilodalton Major Extracellular Protein of *Mycobacterium tuberculosis*", Infection and Immunity, 64:3038-47 (1996).

Horwtiz et al., "Recombinant Bacillus Calmette-Guerin (BCG) Vaccines Expressing the *Mycobacterium tuberculosis* 30-kDa Major Secretory Protein Induce Greater Protective Immunity Against Tuberculosis Than Conventional BCG Vaccines in a Highly Susceptible Animal Model", PNAS, 97:13853-8 (2000).

Langermann et al., "Protective Humoral Response Against Pneumococcal Infection in Mice Elicited by Recombinant Bacille Calmette-Guerin Vaccines Expressing Pneumococcal Surface Protein A", J Exp Med., 180:2277-86 (1994).

Langermann et al., "Systemic and Mucosal Immunity Induced by BCG Vector Expressing Outer-Surface Protein A of *Borrelia burgdorferi*", Nature, 372:552-5 (1994).

(Continued)

*Primary Examiner* — Albert Navarro
(74) *Attorney, Agent, or Firm* — K&L Gates LLP; Louis C. Cullman; Michelle Glasky Bergman

(57) ABSTRACT

Immunogenic compositions comprising recombinant attenuated intracellular pathogens that have been transformed to express recombinant immunogenic antigens of the same or other intracellular pathogens are provided. Exemplary immunogenic compositions include, but are not limited to attenuated recombinant *Mycobacteria* expressing the major extracellular non-fusion proteins of *Mycobacteria* and/or other intracellular pathogens. Other embodiments are provided wherein the recombinant attenuated intracellular pathogen is auxotrophic.

9 Claims, 13 Drawing Sheets

OTHER PUBLICATIONS

Lee et al., "T-Cell Epitope Mapping of the Three Most Abundant Extracellular Proteins of *Mycobacterium tuberculosis* in Outbred Guinea Pigs", Infection and Immunity, 67:2665-70 (1999).

Naito et al., "The Antigen 85 Complex Vaccine Against Experimental *Mycobacterium leprae* Infection in Mice", Vaccine, 19:795-8 (2000).

Ohara et al., "Characterization of the Transcriptional Initiation Regions of Genes for the Major Secreted Protein Antigens 85C and MPB51 of *Mycobacerium bovis* BCG", Microbial Pathogenesis, 23:303-10, (1997).

Ohara et al., "Inhibition of Multiplication of *Mycobacterium leprae* in Mouse Foot Pads by Recombinant Bacillus Calmette-Guerin (BCG)", Vaccine, 19:1294-7 (2000).

Stover et al., "New Use of BCG for Recombinant Vaccines", Nature, 351:456-60 (1991).

Stover et al., "Protective Immunity Elicited by rBCG Vaccines", Dev. Biol. Stand., 82:163-70 (1994).

Stover et al., "Protective Immunity Elicited by Recombinant Bacille Calmette-Guerin (BCG) Expressing Outer Surface Protein A (OspA) Lipoprotein: A Candidate Lyme Disease Vaccine", J. Exp. Med., 178:197-209 (1993).

Stover et al., "Use of Recombinant BCG as a Vaccine Delivery Vehicle", Advances in Experimental Medicine and Biology, 327:175-82 (1992).

Yasutomi et al., "Immunization with Recombinant BCG-SIV Elicits SIV-Specific Cytotoxic T. Lymphocytes in Rhesus Monkeys", The Journal of Immunology, 150:3101-7 (1993).

Belisle, JT et al. "Role of the major antigen of *Mycobacterium tuberculosis* in cell wall biogenesis." Science 276:1420-1422, 1997.

Horwitz, MA et al. "Protective immunity against tuberculosis induced by vaccination with major extracellular proteins of *Mycobacterium tuberculosis*." Proc. Natl. Acad. Sci. USA 92:1530-1534, 1995.

Brooks, JV et al. "Boosting vaccine for tuberculosis." Infect. Immun. 69:2714-17, 2001.

Guleria, I et al. "Auxotrophic vaccines for tuberculosis." Nature Medicine 2:334-337, 1996.

Sambandamurthy, VK et al. "A pantothenate auxotroph of *Mycobacterium tuberculosis* is highly attenuated and protects mice against tuberculosis." Nature Medicine 8:1171-1174, 2002.

Horwitz, MA et al. "A new vaccine against tuberculosis affords greater survival after challenge than the current vaccine in the guinea pig model of pulmonary tuberculosis." Infect. Immun. 71:1672-1679, 2003.

Gobin, J. et al. "Characterization of exochelins of the *Mycobacterium bovis* type strain and BCG substrains." Infect. Immun. 67:2035-2039, 1999.

Harth, G et al. "A two-plasmid system for stable, selective-pressure-independent expression of multiple extracellular proteins in mycobacteria." Microbiology 150:2143-2151, 2004.

* cited by examiner

1, COOMASSIE STAINED PROTEINS
2, IMMUNOBLOT WITH ANTI-30 kDA PROTEIN IgG AFTER 4 WEEKS
3, IMMUNOBLOT WITH ANTI-30 kDa PROTEIN IgG AFTER 12 WEEKS

Experiment 1: Skin tests to Protein r30

Experiment 2: Skin tests to Protein r30

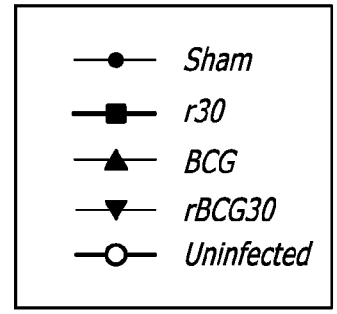
FIG. 3a
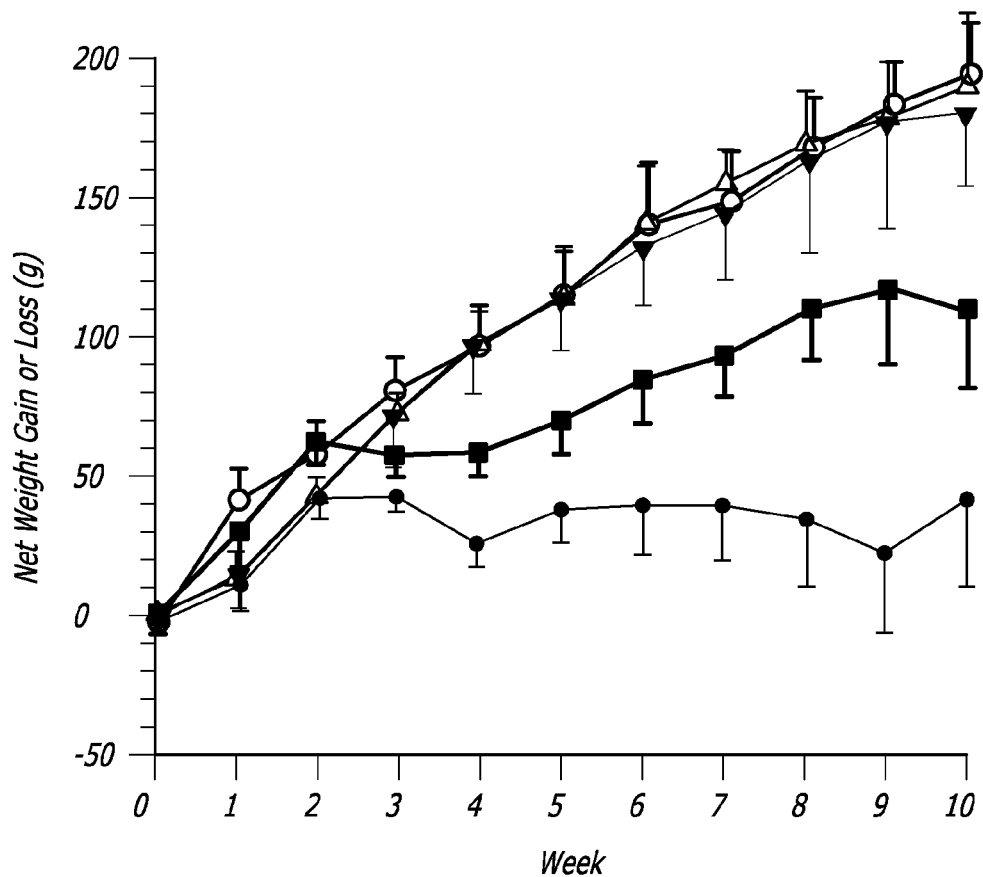

Experiment 2: Weights of Guinea Pigs After Challenge

Two-Plasmid System for the Expression of *M. tuberculosis* 30 kDa Protein in *M. bovis* BCG Tice

| kDa | wild-type | pMTB30 | pGB9.2-30 | pMTB30 + pGB9.2-30 | wild-type | pNBV1-30 | pGB9.2-30 | pNBV1-30 + pGB9.2-30 | 30 kDa Control |
|---|---|---|---|---|---|---|---|---|---|
| 66— | | | | | | | | | |
| 45— | | | | | | | | | |
| 36— | | | | | | | | | |
| 29— | | | | | | | | | |
| 24— | | | | | | | | | |
| 20— | | | | | | | | | |
| 14— | | | | | | | | | |
| | C  I | C  I | C  I | C  I | C  I | C  I | C  I | C  I | I |
| 30 kDa Protein [µg/5x10⁹CFU] | 5 | 28 | 14 | 42 | 5 | 34 | 14 | 48 | |

C = Coomassie-stained SDS-PAGE Gels of Culture Filtrates
I = Immunoblots of Culture Filtrates

*FIG. 11*

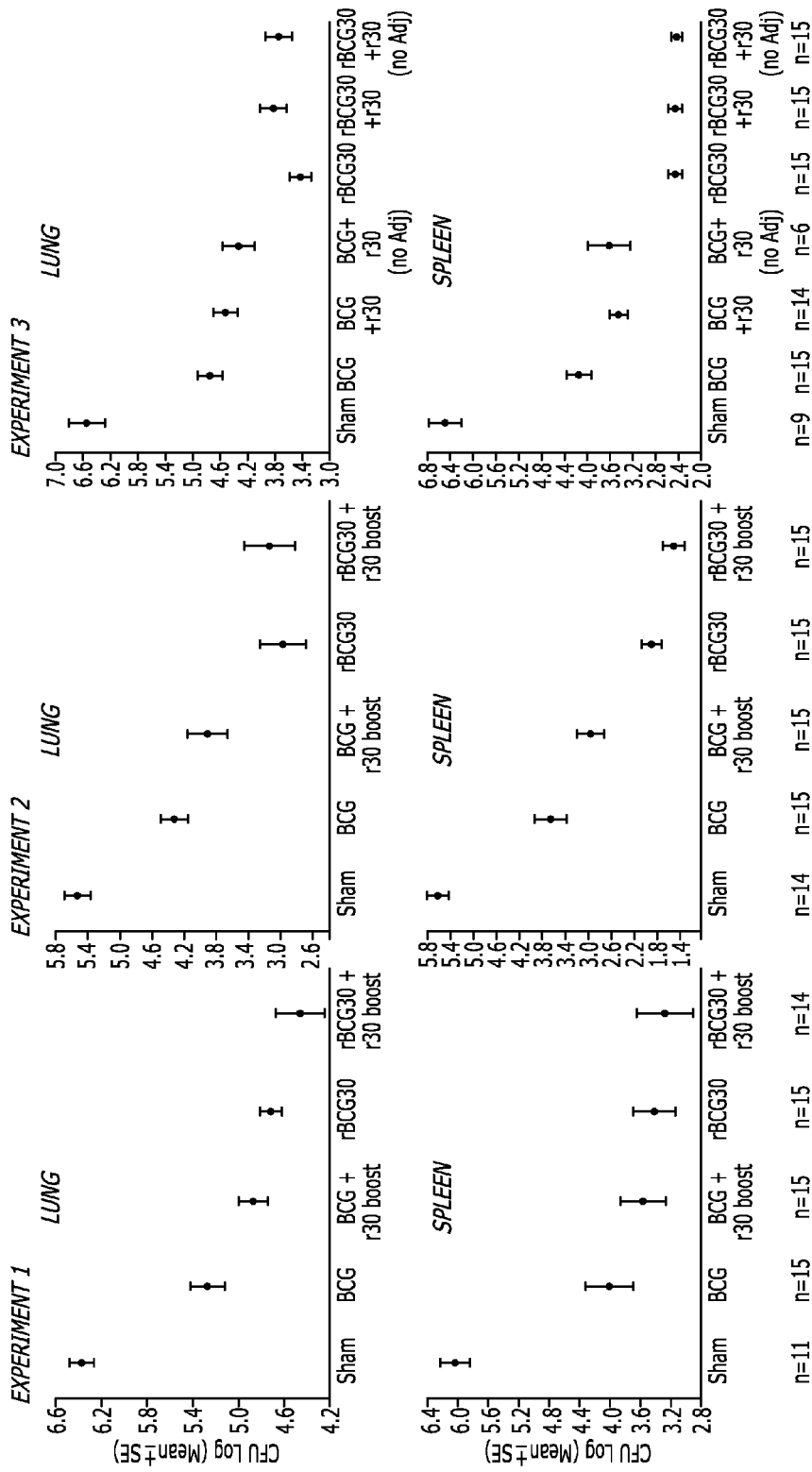

RECOMBINANT INTRACELLULAR PATHOGEN IMMUNOGENIC COMPOSITIONS AND METHODS OF USE

CROSS REFERENCE TO RELATED APPLICATIONS

This application is a divisional of U.S. patent application Ser. No. 10/595,385 filed Apr. 13, 2006, which is an application under section 371 of International patent application number PCT/US04/034206 filed Oct. 15, 2004, which claims priority under 35 U.S.C. §119(e) to U.S. provisional application Ser. No. 60/512,565 filed Oct. 16, 2003, the entire contents of which are hereby incorporated by reference in their entirety.

REFERENCE TO GOVERNMENT

This invention was made with Government support under Grant No. AI31338 awarded by the Department of Health and Human Services. The Government has certain rights in this invention.

FIELD OF THE INVENTION

The present invention generally relates to immunogenic compositions derived from recombinant attenuated intracellular pathogenic bacteria. More specifically, the present invention relates to immunogenic compositions comprising recombinant attenuated Mycobacteria that over express and secrete major extracellular proteins. Moreover, the immunogenic compositions of the present invention also comprise recombinant attenuated Mycobacteria including auxotrophic, prototrophic and metabolically impaired strains. The immunogenic compositions of the present invention are useful in inducing immune responses in hosts.

BACKGROUND OF THE INVENTION

It has long been recognized that parasitic microorganisms possess the ability to infect animals thereby causing disease and often death. Pathogenic agents have been a leading cause of death throughout history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic organisms are evidenced by the resurgence of various diseases such as tuberculosis, as well as the appearance of numerous drug resistant strains of bacteria and viruses.

Among those pathogenic agents of major epidemiological concern, intracellular bacteria have proven to be particularly intractable in the face of therapeutic or prophylactic measures. Intracellular bacteria, including the genus *Mycobacterium*, complete all or part of their lifecycle within the cells of the infected host organism rather than extracellularly. Around the world, intracellular bacteria are responsible for untold suffering and millions of deaths each year. Tuberculosis is the leading cause of death from a single disease agent worldwide, with 8 million new cases and 2 million deaths annually. In addition, intracellular bacteria are responsible for millions of cases of leprosy. Other debilitating diseases transmitted by intracellular agents include cutaneous and visceral leishmaniasis, American trypanosomiasis (Chagas disease), listeriosis, toxoplasmosis, histoplasmosis, trachoma, psittacosis, Q-fever, and legionellosis.

Currently it is believed that approximately one-third of the world's population is infected by *M. tuberculosis* resulting in millions of cases of pulmonary tuberculosis annually. More specifically, human pulmonary tuberculosis primarily caused by *M. tuberculosis* is a major cause of death in developing countries. *Mycobacterium tuberculosis* is capable of surviving inside macrophages and monocytes, and therefore may produce a chronic intracellular infection. *Mycobacterium tuberculosis* is relatively successful in evading the normal defenses of the host organism by concealing itself within the cells primarily responsible for the detection of foreign elements and subsequent activation of the immune system. Moreover, many of the front-line chemotherapeutic agents used to treat tuberculosis have relatively low activity against intracellular organisms as compared to extracellular forms. These same pathogenic characteristics have heretofore limited the effectiveness of immunotherapeutic agents or immunogenic compositions against tubercular infections.

Recently, tuberculosis resistance to one or more drugs was reported in 36 of the 50 United States. In New York City, one-third of all cases tested was resistant to one or more major drugs. Though non-resistant tuberculosis can be cured with a long course of antibiotics, the outlook regarding drug resistant strains is bleak. Patients infected with strains resistant to two or more major antibiotics have a fatality rate of around 50%. Accordingly, safe and effective immunogenic compositions against multi-drug resistant strains of *M. tuberculosis* are sorely needed.

Initial infections of *M. tuberculosis* almost always occur through the inhalation of aerosolized particles as the pathogen can remain viable for weeks or months in moist or dry sputum. Although the primary site of the infection is in the lungs, the organism can also cause infection of nearly any organ including, but not limited to, the bones, spleen, kidney, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic.

When *M. tuberculosis* is not controlled by the infected subject it often results in the extensive degradation of lung tissue. In susceptible individuals lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation (conversion of affected tissues into a soft cheesy substance).

While *M. tuberculosis* is a significant pathogen, other species of the genus *Mycobacterium* also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. Another important pathogenic species of the genus *Mycobacterium* is *M. leprae* that causes millions of cases of the ancient disease leprosy. Other species of this genus which cause disease in animals and man include *M. kansasii, M. avium intracellulare, M. fortuitum, M. marinum, M. chelonei*, and *M. scrofulaceum*. The pathogenic mycobacterial species frequently exhibit a high degree of homology in their respective DNA and corresponding protein sequences and some species, such as *M. tuberculosis* and *M. bovis*, are highly related.

Attempts to eradicate tuberculosis using immunogenic compositions was initiated in 1921 after Calmette and Guérin successfully attenuated a virulent strain of *M. bovis* at the Institut Pasteur in Lille, France. This attenuated *M. bovis* became known as the Bacille Calmette Guérin, or BCG for short. Nearly eighty years later, immunogenic compositions derived from BGC remain the only prophylactic therapy for tuberculosis currently in use. In fact, all BCG immunogenic compositions available today are derived from the original strain of *M. bovis* developed by Calmette and Guérin at the Institut Pasteur.

The World Health Organization considers the BCG immunogenic compositions an essential factor in reducing tuberculosis worldwide, especially in developing nations. In theory, the BCG immunogenic composition confers cell-mediated immunity against an attenuated mycobacterium that is immunologically related to *M. tuberculosis*. The resulting immune response should inhibit primary tuberculosis. Thus, if primary tuberculosis is inhibited, latent infections cannot occur and disease reactivation is avoided.

Current BCG immunogenic compositions are provided as lyphophilized cultures that are re-hydrated with sterile diluent immediately before administration. The BCG immunogenic composition is given at birth, in infancy, or in early childhood in countries that practice BCG vaccination, including developing and developed countries. Adult visitors to endemic regions who may have been exposed to high doses of infectious mycobacteria may receive BCG as a prophylactic providing they are skin test non-reactive. Adverse reactions to the immunogenic composition are rare and are generally limited to skin ulcerations and lymphadenitis near the injection site. However, in spite of these rare adverse reactions, the BCG immunogenic composition has an unparalleled history of safety with over three billion doses having been administered worldwide since 1930.

However, the unparalleled safety of traditional BCG immunogenic compositions is coming under increased scrutiny and has created a paradox for healthcare practitioners. The population segments most susceptible to mycobacterial infections are the immunosuppressed. Persons suffering from early or late-stage HIV infections are particularly susceptible to infection. Unfortunately, many persons in the early-stage of HIV infection are unaware of their immune status. It is likely that these individuals may voluntarily undergo immunization using a live attenuated immunogenic composition such as BCG without being forewarned of their unique risks. Moreover, other mildly immunosuppressed individuals may also unwittingly undergo immunization with BCG hoping to avoid mycobacterial disease. Therefore, safer, more efficacious BCG and BCG-like immunogenic compositions are desirable.

Recently, significant attention has been focused on using transformed BCG strains to produce immunogenic compositions that express various cell-associated antigens. For example, C. K. Stover, et al. have reported a Lyme Disease immunogenic composition using a recombinant BCG (rBCG) that expresses the membrane associated lipoprotein OspA of *Borrelia burgdorferi*. Similarly, the same author has also produced a rBCG immunogenic composition expressing a pneumococcal surface protein (PsPA) of *Streptococcus pneumoniae*. (Stover C K, Bansal G P, Langerman S, and Hanson M S. 1994. Protective immunity elicited by rBCG immunogenic compositions. In: Brown F. (ed): Recombinant Vectors in Immunogenic composition Development. Dev Biol Stand. Dasel, Karger, Vol. 82:163-170)

U.S. Pat. No. 5,504,005 (the "'005" patent") and U.S. Pat. No. 5,854,055 (the "'055 patent") both issued to B. R. Bloom et al., disclose theoretical rBCG vectors expressing a wide range of cell associated fusion proteins from numerous species of microorganisms. The theoretical vectors described in these patents are either directed to cell associated fusion proteins, as opposed to extracellular non-fusion protein antigens, and/or the rBCG is hypothetically expressing fusion proteins from distantly related species. Moreover, the recombinant cell associated fusion proteins expressed in these models are encoded on DNA that is integrated into the host genome and under the control of heat shock promoters. Consequently, the antigens expressed are fusion proteins and expression is limited to levels approximately equal to, or less than, the vector's native proteins.

Furthermore, neither the '005 nor the '055 patent disclose animal model safety testing, immune response development or protective immunity in an animal system that closely emulates human disease. In addition, only theoretical rBCG vectors expressing *M. tuberculosis* fusion proteins are disclosed in the '005 and '055 patents; no actual immunogenic compositions are enabled. Those immunogenic composition models for *M. tuberculosis* that are disclosed are directed to cell associated heat shock fusion proteins, not extracellular non-fusion proteins.

U.S. Pat. No. 5,830,475 (the "'475 patent") also discloses theoretical mycobacterial immunogenic compositions used to express fusion proteins. The DNA encoding these fusion proteins resides in extrachromosomal plasmids under the control of mycobacterial heat shock protein and stress protein promoters. The immunogenic compositions disclosed are intended to elicit immune responses in non-human animals for the purpose of producing antibodies thereto and not shown to prevent intracellular pathogen diseases in mammals. Moreover, the '475 patent does not disclose recombinant immunogenic compositions that use protein specific promoters to express extracellular non-fusion proteins.

U.S. Pat. No. 6,467,967 issued to the present inventor, claims immunogenic compositions comprising a recombinant BCG having an extrachromosomal nucleic acid sequence comprising a gene encoding a *M. tuberculosis* 30 kDa major extracellular protein, wherein said *M. tuberculosis* 30 kDa major extracellular protein is over-expressed and secreted. Moreover, the present inventors have filed continuation-in-part applications (U.S. patent application Ser. Nos. 10/261,981 filed Sep. 30, 2002, now abandoned and 10/439,611 filed May 15, 2003) claiming additional recombinant BCG that over-express other *M. tuberculosis* major extracellular proteins.

Therefore, there remains a need for recombinant intracellular pathogen immunogenic compositions that express major extracellular non-fusion proteins of intracellular pathogens that are closely related to the immunogenic composition.

Furthermore, there is a need for recombinant intracellular pathogen immunogenic compositions that are capable of over-expressing recombinant extracellular non-fusion proteins by virtue of extrachromosomal DNA having non-heat shock gene promoters or non-stress protein gene promoters.

Specifically, there remains an urgent need to produce intracellular pathogen immunogenic compositions that provide recipients protection from diseases that is superior to the protection afforded BCG immunogenic composition recipients. Moreover, there is an urgent need to provide both developed and developing countries with a cost efficient, immunotherapeutic and prophylactic treatment for tuberculosis and other intracellular pathogens.

Additionally, there remains a need for intracellular pathogen immunogenic compositions that can be safely administered to immunosuppressed, or partially immunosuppressed individuals.

Therefore, it is an object of the present invention to provide immunogenic compositions for the diagnosis, treatment, prevention, inhibition or palliation of disease caused by intracellular pathogens.

It is another object of the present invention to provide immunogenic compositions for the diagnosis, treatment, prevention, inhibition or palliation of disease caused by intracellular pathogens using intracellular pathogens that have been transformed to express the major recombinant immunogenic antigens of the same intracellular pathogen, another intracellular pathogen, or both.

It is yet another object of the present invention to provide immunogenic compositions for the diagnosis, treatment, prevention, inhibition or palliation of disease caused by mycobacteria using recombinant BCG that expresses the extracellular protein(s) of a pathogenic mycobacterium.

It is another object of the present invention to provide immunogenic compositions for the diagnosis, treatment, prevention, inhibition or palliation of tuberculosis using recombinant strains of BCG that express and secrete one or more major extracellular proteins of *Mycobacterium tuberculosis*.

It is yet another object of the present invention to provide the aforementioned immunogenic compositions in a form that can be safely administered to immunosuppressed, or partially immunosuppressed individuals.

And finally, it is an object of the present invention to provide superior vaccination strategies using the immunogenic compositions of the present invention.

SUMMARY OF THE INVENTION

The present invention accomplishes the above-described and other objects by providing a new class of immunogenic compositions and immunotherapeutics and methods for the diagnosis, treatment, prevention, inhibition or palliation of intracellular pathogen diseases in mammals. Historically intracellular pathogen immunogenic compositions and immunotherapeutics have been prepared from the intracellular pathogen itself or a closely related species. These old immunogenic composition models were composed of the entire microorganism or subunits thereof. For example, the first, and currently only available immunogenic composition, for *Mycobacterium tuberculosis* (Mtb) is an attenuated live immunogenic composition made from the closely related intracellular pathogen *M. bovis*. Recently, the present inventors have discovered that specific extracellular products of intracellular pathogens that are secreted into growth media can be used to illicit potent immune responses in mammals either as individual subunits, or in subunit combinations.

The present invention discloses multiple related vaccine compositions and corresponding vaccine strategies predicated on the same inventive concept but modified to achieve different immunoprotective objectives. The unifying inventive concept is the use of a transformed, or recombinant, BCG (rBCG) as the primary vaccine. The rBCG expresses one or more antigenic polypeptides derived from an intracellular pathogen other than the un-transformed BCG itself. An exemplary embodiment of this unifying inventive concept is a rBCG that expresses recombinant *M. tuberculosis* major extracellular proteins.

One immunoprotective strategy of the present invention is prime-boost vaccination. Prime-boost involves administering a first immunogenic composition followed by a second, related, but different immunogenic composition (See for example Ramshaw I A, and Ramsay A J. 2000. The prime-boost strategy: exciting prospects for improved vaccination. Immunol Today 21:160-2; Tanghe A, D'Souza S, Rosseels V, Denis O, Ottenhoff T H M, Dalemans W, Wheeler C, and Huygens K. 2001. Improved immunogenicity and protective efficacy of a tuberculosis DNA vaccine encoding Ag 85 by protein boosting. Infect. Immun. 69:3041-7; Feng C G, Palendira U, Demangel C, Spratt J M, Malin A S and Britton W J. 2001. Priming by DNA immunization augments protective efficacy of *Mycobacterium bovis* Bacille Calmette-Guerin against tuberculosis. Infect. Immun. 69:4174-6 and Goonetilleke N P, McShane H, Hannan C M, Anderson R J, Brookes R H and Hill A V S. 2003. Enhanced immunogenicity and protective efficacy against *Mycobacterium tuberculosis* of Bacille Calmette-Guérin vaccine using mucosal administration and boosting with a recombinant modified vaccinia virus Ankara. J. Immunol. 171:1602-9). For example, the present invention describes a prime-boost vaccination strategy by which a recombinant BCG over expressing a *M. tuberculosis* major extracellular protein is administered first, followed at a later time by the administration of the purified *M. tuberculosis* major extracellular protein. The administration of the vaccine in this way induces enhanced protection over that achieved by immunization with BCG alone, by immunization with a recombinant BCG over-expressing the *M. tuberculosis* 30 kDa major secretory protein (also known as Antigen 85B) (rBCG30) alone, or even by immunization with BCG first followed later by immunization with the purified *M. tuberculosis* major extracellular protein. In the non-limiting examples that follow, the first immunization ("prime") uses rBCG30, a rBCG strain over expressing the *M. tuberculosis* 30 kDa major secretory protein, a.k.a. Antigen 85B or r30, and the second immunization ("boost") uses purified *M. tuberculosis* 30 kDa major secretory protein. The purified *M. tuberculosis* 30 kDa major secretory protein may be extracted from whole cells, extracted from culture wherein *M. tuberculosis* has been previously cultivated, or produced using recombinant technologies. In another embodiment the second immunization may be a truncated polypeptide having an immunodominant epitope of the *M. tuberculosis* 30 kDa major secretory protein.

A second related vaccine composition and immunoprotective strategy is useful in treating immunosuppressed individuals using a growth regulatable rBCG. As used herein "growth regulatable" refers to an organism that only divides when provided with a specific nutrient. The specific nutrient is either co-administered with the immunogenic composition, provided to the immunogenic composition recipient subsequently or the rBCG must be "pre-loaded" with the nutrient. The growth regulatable rBCG may be used alone, or as part of a prime-boost strategy. The growth regulatable rBCG may be an auxotroph or possess an altered gene such that a required metabolic function is disabled (metabolically impaired). In the latter case, an exemplary embodiment includes, but is not limited to, a metabolically impaired rBCG having a defective or deleted gene that normally encodes for a siderophore (microbial iron chelator). The siderophore deficient rBCG can be "pre-loaded" with an essential mineral in an amount sufficient to permit a limited number of divisions. Thus, when the stored mineral is depleted the siderophore deficient rBCG ceases multiplying in the host. In one embodiment of the present invention the siderophore is either mycobactins or exochelins and the essential mineral is iron. In another embodiment of the present invention, the growth regulatable rBCG auxotroph is deficient in pantothenic acid.

A third related immunogenic composition includes a rBCG encoding for a plurality of recombinant *M. tuberculosis* major extracellular proteins wherein the genes encoding the major extracellular proteins reside on a plurality of separate plasmids. This embodiment may be used alone, or as part of a prime-boost strategy and the rBCG having a plurality of separate antigen encoding plasmids may be an auxotroph or metabolically impaired rBCG. One such immunogenic composition comprises a rBCG having a first extrachromosomal nucleic acid sequence comprising a genetic construct encoding a first *M. tuberculosis* major extracellular protein and a second extrachromosomal nucleic acid sequence encoding the same or a different major extracellular protein. In one embodiment, the first major extracellular protein is expressed at a higher level than the second major extracellular protein and, as both the first and the second major extracellular protein are over expressed and secreted, an immune response is induced in an animal. In an exemplary embodiment the first major extracellular protein is selected from the group consisting of the 32 kDa, 30 kDa and 23.5 kDa *M. tuberculosis* major extracellular proteins and the second major extracellular protein selected from the group consisting of the 32 kDa, 30 kDa and 23.5 kDa *M. tuberculosis* major extracellular protein wherein the first and second major extracellular proteins are different.

In one embodiment the immunogenic compositions of the present invention are made using recombinant strains of the Bacille Calmette Guérin, or BCG. In this embodiment the recombinant BCG expresses major extracellular proteins of pathogenic mycobacteria including, but not limited to, *M. tuberculosis, M. leprae* and *M. bovis*, to name but a few.

The major extracellular proteins expressed by the rBCG include, but are not limited to, the 12 kDa, 14 kDa, 16 kDa, 23 kDa, 23.5 kDa, 30 kDa, 32A kDa, 32B kDa, 45 kDa, 58 kDa, 71 kDa, 80 kDa, and 110 kDa of *Mycobacterium* sp. and respective analogs, homologs and subunits thereof including recombinant non-fusion proteins, fusion proteins and derivatives thereof. It is apparent to those of ordinary skill in the art that the molecular weights used to identify the major extracellular proteins of Mycobacteria and other intracellular pathogens are only intended to be approximations. Those skilled in the art of recombinant technology and molecular biology will realize that it is possible to co-express (co-translate) these proteins with additional amino acids, polypeptides and proteins, as it is also possible to express these proteins in truncated forms. The resulting modified proteins are still considered to be within the scope of the present invention whether termed native, non-fusion proteins, fusion proteins, hybrid proteins or chimeric proteins.

It is understood that the immunogenic compositions of the present invention may be administered using any approach that will result in the appropriate immune response including, but not limited to, intradermal, subcutaneous, intramuscular, intranasal, intraperitoneal, oral, or inhalation. Following a suitable post inoculation period, the vaccinated mammals were challenged with an infectious *M. tuberculosis* aerosol. Mammals receiving the immunogenic composition of the present invention were remarkably disease free as compared to mammals receiving BCG alone, the major extracellular protein alone, or any combinations thereof.

Other objects and features and advantages of the present invention will be apparent to those skilled in the art from a consideration of the following detailed description of preferred exemplary embodiments thereof taken in conjunction with the Figures which will first be described briefly.

BRIEF DESCRIPTION OF THE DRAWINGS

FIG. 11 depicts Coomassie blue stained gels illustrating the secretion of pGB9.2-30 expressed *M. tuberculosis* 30 kDa protein in various Mycobacteria.

FIG. 14 graphically depicts CFU of infectious *M. tuberculosis* recovered from guinea pigs' lungs and spleens following post immunization challenge with *M. tuberculosis* in animals that were sham-immunized, immunized with BCG or rBCG30 alone, or immunized with BCG or rBCG30 and boosted with purified recombinant *M. tuberculosis* 30 kDa major extracellular protein (r30) (prime-boost).

BRIEF DEFINITION OF TERMS

Figures 1A, 1B:
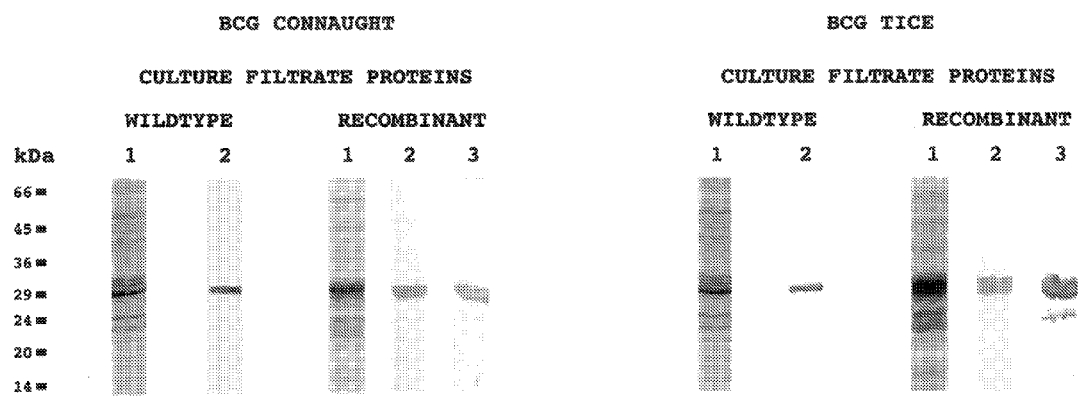
FIG. 1 depicts Coomassie blue stained gels labeled 1*a* and 1*b* illustrating the secretion of *Mycobacterium tuberculosis* recombinant 30 kDa protein by transformed strains of BCG from culture filtrates.

To facilitate an understanding of the following Detailed Description, Examples and appended claims it may be useful to refer to the following definitions. These definitions are non-limiting in nature and are supplied merely as a convenience to the reader.

Auxotroph or auxotrophic: As used herein "auxotroph" refers to a microorganism having a specific nutritional requirement NOT required by the wild-type organism. In the absence of the required nutrient the auxotroph will not grow whereas the wild-type will thrive.

Gene: A "gene" as used herein refers to at least a portion of a genetic construct having a promoter and/or other regulatory sequences required for, or that modify the expression of, the genetic construct.

Genetic Construct: A "genetic construct" as used herein shall mean a nucleic acid sequence encoding for at least one major extracellular protein from at least one intracellular pathogen. In one embodiment of the present invention the genetic construct is extrachromosomal DNA.

Growth Regulatable: As used herein the term "growth regulatable" refers to an auxotrophic or metabolically impaired form of the present invention's immunogenic compositions. Growth is regulated by providing a nutrient essential for the auxotroph's growth at a concentration sufficient to induce growth.

Host: As used herein "host" refers to the recipient of the present immunogenic compositions. Exemplary hosts are mammals including, but not limited to, primates, rodents, cows, horses, dogs, cats, sheep, goats, pigs and elephants. In one embodiment of the present invention the host is a human. For the purposes of this disclosure host is synonymous with "vaccinees."

Immunogen: As used herein the term "immunogen" shall mean any substrate that elicits an immune response in a host. Immunogens of the present invention include, but are not limited to major extracellular proteins, and their recombinant forms, derived from intracellular pathogens, such as, but not limited members of the genus *Mycobacterium*.

Immunogenic Composition: An "immunogenic composition" as used herein comprises a recombinant vector, with or without an adjuvant, such as an intracellular pathogen, that expresses and/or secretes an immunogen in vivo wherein the immunogen elicits an immune response in the host. The immunogenic compositions disclosed herein may be a prototrophic, auxotrophic or metabolically impaired transformant. The immunogenic compositions of the present invention may or may not be immunoprotective or therapeutic. When the immunogenic compositions of the present invention prevent, ameliorate, palliate or eliminate disease from the host then the immunogenic composition may optionally be referred to as a vaccine. However, the term immunogenic composition is not intended to be limited to vaccines.

Major extracellular protein: As used herein, the term "major extracellular protein" is synonymous with "major secretory protein." The present inventors have previously described and characterized the mycobacterial major extracellular proteins of the present invention. The descriptions and characterization of the present major extracellular proteins can be found, without limitation, in U.S. Pat. No. 6,599,510, issued Jul. 29, 2003 to the present inventors, the entire contents of which are hereby incorporated by reference.

Metabolically impaired: As used herein "metabolically impaired" shall mean a recombinant expression vector, specifically a rBCG, that has an altered or deleted gene that is essential for normal metabolism. In the present case, the metabolic alteration results in a rBCG that cannot divide in vivo unless the nutrient is provided to the rBCG (pre-loading) prior to the rBCG being administered in vivo.

Nucleic Acid Sequence: As used herein the term "nucleic acid sequence" shall mean any continuous sequence of nucleic acids.

Prototrophic: As used herein "prototrophic" refers to a rBCG that that does not require any substance in its nutrition additional to those required by the wild-type.

Transformant: As used herein a "transformant" refers to a microorganism that has been transformed with at least one heterologous or homologous nucleic acid encoding for a polypeptide that is expressed and/or secreted. In one embodiment of the present invention the transformant is BCG.

DETAILED DESCRIPTION OF THE INVENTION

The following Detailed Description will include five distinct sections for ease of understanding and to assure enablement of all embodiments of the present invention. The first section provides an introduction to the major inventive concepts of the present invention and a brief background summarizing important technical themes. The second section describes the immunogenic compositions in detail. The immunogenic compositions described therein include rBCG strains that are prototrophic, auxotrophic and metabolically impaired. Each rBCG is transformed to express one or a plurality of immunogens derived from intracellular pathogens; the exemplary embodiment being Mycobacterial major extracellular proteins. The rBCG may have one or a plurality of extrachromosomal plasmids having nucleic acid sequences that encode for one or a plurality of immunogens. The third section details representative methods for preparing the various plasmids used to transform the rBCG of the present invention. Section four presents novel vaccination strategies, specifically a prime boost strategy using the rBCG previously described. Finally, section five provides detailed examples of safety and efficacy testing conducted by the present inventors using the immunogenic compositions and vaccine strategies disclosed in sections II through IV.

I. Introduction

The present invention is directed to generally immunogenic compositions comprising attenuated, or avirulent, recombinant intracellular pathogens that express and/or secrete recombinant immunogenic antigens of the same, or another species. The immunogenic compositions of the present invention can be prototrophic, auxotrophic or metabolically impaired. Moreover, the immunogenic compositions of the present invention may be used alone, or as part of a prime-boost vaccination strategy. For example, in one embodiment of the present invention a vaccination strategy and combined immunogenic compositions are disclosed that comprise a recombinant BCG over expressing at least one *M. tuberculosis* major extracellular protein administered first followed at a later time by the administration of the same *M. tuberculosis* major extracellular protein(s) in pure or partially purified form. The administration of the immunogenic compositions in this way induces enhanced protection over that achieved by immunization with BCG alone, by immunization with rBCG alone, or even by immunization with BCG first followed later by immunization with the purified *M. tuberculosis* major extracellular protein.

The immunogenic compositions of the present invention may express one or a plurality of immunogens. The immunogens may include, but are not limited to major extracellular proteins derived from intracellular pathogens such as, but not limited to Mycobacteria sp. The immunogenic compositions, such as rBCG, may have one, or a plurality of extrachromasomal plasmids encoding for one or more immunogens.

Each immunogenic composition of the present invention can express at least one immunogen of various molecular weights specific for a given intracellular pathogen. For example, the present inventors have previously identified *M. tuberculosis* immunogens that can include, but are not limited to, the major extracellular proteins 12 kDa, 14 kDa, 16 kDa, 23 kDa, 23.5 kDa, 30 kDa, 32A kDa, 32B kDa, 45 kDa, 58 kDa, 71 kDa, 80 kDa, 110 kDa and respective analogs, homologs, subunits and degenerative variants thereof including recombinant non-fusion proteins, fusion proteins and derivatives thereof. (See U.S. Pat. Nos. 6,599,510 and 6,752,993, the entire contents of which are hereby incorporated by reference). It is apparent to those of ordinary skill in the art that the molecular weights used to identify the major extracellular proteins of Mycobacteria and other intracellular pathogens are only intended to be approximations. Those skilled in the art of recombinant technology and molecular biology will realize that it is possible to co-express (co-translate) these proteins with additional amino acids, polypeptides and proteins, as it is also possible to express these proteins in truncated forms. The resulting modified proteins are still considered to be within the scope of the present invention whether termed native, non-fusion proteins, fusion proteins, hybrid proteins or chimeric proteins. For the purposes of the present invention, fusion proteins are defined to include, but not limited to, the products of two or more coding sequences from different genes that have been cloned together and that, after translation, form a single polypeptide sequence.

II. Immunogenic Compositions

One or more of the following bacterial strains were used to prepare the immunogenic compositions described below. These strains are merely representative and not intended as a limitation. Persons having ordinary skill in the art of molecular biology and in conjunction with the cited references may select other strains useful for preparing the immunogenic compositions of the present invention.

Mycobacterial strains of the present invention: BCG Tice and BCG Connaught. Wild-type *M. bovis* BCG Tice was purchased from Organon and wild-type *M. bovis* BCG Connaught was obtained from Connaught Laboratories, Toronto, Canada. *M. smegmatis* 1-2c wild-type was a gift from Peadar O'Gaora [Imperial College, London, UK (Herrmann J L, O'Gaora P, Gallagher A, Thole J E R and Young D B. 1996. Bacterial glycoproteins: a link between glycosylation and proteolytic cleavage of a 19 kDa antigen from *Mycobacterium tuberculosis*. EMBO J 15:3547-54, hereby incorporated by reference in its entirety)]; and *M. tuberculosis* Erdman wild-type was obtained from the American Type Culture Collection (ATCC#35801). *M. tuberculosis* Erdman was used to generate its isogenic mutants *M. tuberculosis* Erdman glnA1::Tn5 aph($Km^r$), designated [glnA1::$Km^r$], and *M. tuberculosis* Erdman [$Hyg^r$; unmapped insertion]. The strains were maintained in 7H9 medium pH 6.7 (Difco) at 37° C. in a 5% $CO_2$-95% air atmosphere as unshaken cultures. Cultures were sonicated once or twice weekly for 5 min in a sonicating water bath to reduce bacterial clumping.

*Escherichia coli* strains used: The following bacterial strains were used (in alphabetical order): *E. coli* strains: DH5a (recA1 endA1 gyrA96 thi-1 hsdR17($rK^-mK^+$) supE44 relA1 lacZ$\alpha^+$) was obtained from Invitrogen; S17($\lambda pir^+$ recA thi pro hsd$R^-M^+$ [pLC28$Cam^rStr^s$]) and SM10 ($\lambda pir^+$ $Cam^sStr^r$) were gifts from Olaf Schneewind [University of Chicago, Chicago, Ill. (Cheng L W, Anderson D M and Schneewind O. 1997. Two independent type III secretion mechanisms for YopE in *Yersinia enterocolitica*. Mol Microbiol 24:757-65, hereby incorporated by reference in its entirety)]; and XL-1 Blue {recA1 endA1 gyrA96 thi1 hsdR17 supE44 relA1 lac[F' proAB $lacI^qZ\Delta M15$ Tn10($Tet^r$)]}, and Y1090 {[D(lac)U169 Δlon araD139 strA supF mcrA trpC22::Tn10($Tet^r$)] [pMC9 $Amp^rTet^r$]} were purchased from Stratagene.

*Escherichia coli* strains were maintained in LB broth or agar medium at 37° C. and mycobacterial strains were maintained in 7H9 broth medium or 7H11 agar medium at 37° C. in a 5% $CO_2$-95% air atmosphere. Relevant antibiotics were used at the following concentrations: Ampicillin at 100 μg/mL for *E. coli* and at 20 μg/mL for mycobacteria; apramycin at 50 μg/mL for *E. coli* and 30 μg/mL for mycobacteria; chloramphenicol at 30 μg/mL for *E. coli*, hygromycin at 250 μg/mL for *E. coli* and 50 μg/mL for mycobacteria; kanamycin at 50 μg/mL for *E. coli* and 20 μg/mL for mycobacteria; pyrazinamide at 50 μg/mL for mycobacteria; streptomycin at 30 $\mu g\ mL^{-1}$ for *E. coli*; and tetracycline at 12.5 μg/mL for *E. coli*. Incubations of *E. coli* strains were for 24 h, of *M. smegmatis* strains for 3-5 days, and of *M. bovis* and *M. tuberculosis* strains for 2 weeks at 37° C. in a 5% $CO_2$-95% air atmosphere.

All powdered media were obtained from Becton-Dickinson. Antibiotics for the selective media were from Sigma except for hygromycin which was purchased from Roche Diagnostics. All other reagents were from Sigma unless otherwise specified and were of the highest grade available. Primers for polymerase chain reactions (PCR) and Sanger-type DNA sequence determinations were purchased from Genosys.

A. Recombinant BCG Suitable for Immunocompetent Vaccinees

1. BCG Containing Construct with Stationary Phase Promoter (PhspX) linked to *M. tuberculosis* 30 kDa Major Secretory Protein Coding Region a. Construct with PhspX promoter i. rBCG-pNBV1-[PhspX-30]

When BCG enters a latent phase in the immunized host, it may cease expressing the 30 kDa major secretory protein as well as other endogenous proteins, as occurs when *M. tuberculosis* enters stationary phase. If the recombinant BCG were able to continue to produce the protein during latency, this might result in an enhanced immune response. To achieve this objective, present inventors have placed the 30 kDa protein gene under the control of a promoter (PhspX) active during latency. This promoter is from the alpha-crystallin protein gene which is known to be expressed during late logarithmic and stationary growth and under hypoxic conditions; such conditions may in part mimic latency in vivo (Yuan Y, Crane D D and Barry III C E. 1996. Stationary phase-associated protein expression in Mycobacteria *tuberculosis*: Function of the mycobacterial α-crystallin homolog. J. Bact. 178:4484-92; Sherman D R, Voskuil M, Schappinger D, Liao R, Harrell M I, and Schoolnik G K. 2001. Regulation of the *Mycobacterium tuberculosis* hypoxic response gene encoding a-crystallin. Proc. Natl. Acad. Sci. USA 98:7534-9; and Haile Y, Bjune G, and Wiker H G. 2002. Expression of the mceA, esat-6 and hspX genes in *Mycobacterium tuberculosis* and their responses to aerobic conditions and to restricted oxygen supply. Microbiology 148:3881-6; hereby incorporated by reference in their entirety)

1.a.i rBCG-pNBV1-[PhspX-30]

This recombinant strain was generated by electroporating the recombinant plasmid pNBV1, consisting of the vector backbone, a fragment of approximately 750 by located directly upstream of the atg codon of the hspX gene (Rv2031c) of *M. tuberculosis* Erdman and considered the promoter region of this gene, and the 975 base pairs (bp) coding region of the 30 kDa protein gene (fbpB, Rv1886c), into BCG Tice bacteria (Stock #3). The strain stably maintained the recombinant plasmid, even in the absence of the selective antibiotic hygromycin for 3 weeks or approximately 20 generations. The recombinant strain was assayed for its capacity to express and secrete the recombinant 30 kDa protein by gel electrophoresis and immunoblotting with 30 kDa protein specific antisera. Analysis of digitized scans showed the secretion of 9.7 μg of 30 kDa protein by $5\times10^9$ CFU, a value about 2-fold higher than for wild-type BCG Tice (5.1 μg per $5\times10^9$ CFU). Stock vials (Stock #1) were established in 10% glycerol at a concentration of $7.7\times10^7$ particles/mL and stored at −80° C.

2. BCG Containing Single and Double Plasmid Constructs Including pGB9.2 that Encode *M. tuberculosis* 30 kDa or 23.5 kDa Major Secretory Proteins
   a. BCG Containing pGB9.2 Constructs Expressing *M. tuberculosis* 30 kDa or 23.5 kDa Major Secretory Proteins alone
      i. rBCG-pGB9.2-30
      ii. rBCG-pGB9.2-23.5
   b. BCG Containing Two Plasmid Constructs—One Expressing the *M. tuberculosis* 30 kDa Major Secretory Protein and One Expressing *M. tuberculosis* 23.5 kDa Major Secretory Protein
      i. rBCG30 I (pMTB30)+pGB9.2-23.5
      ii. rBCG30 III (pNBV1-30)+pGB9.2-23.5

The plasmid pGB9.2 is present in recombinant BCG strains of the present invention at low copy number, allowing low level expression of *M. tuberculosis* extracellular proteins. Particularly when multiple proteins are expressed, low level expression may be desirable for stable maintenance of the strain and, based upon unpublished findings from this laboratory, for inducement of protective immunity. The plasmid pGB9.2 is compatible with the shuttle vectors pSMT3 and pNBV1 so it can be placed in combination with them in one BCG host. Our studies have shown that plasmid pGB9.2 in combination with a compatible high copy number plasmid allows differential expression of different mycobacterial extracellular proteins, a potentially important factor in optimizing vaccine potency (Harth G, Masleša-Galić S and Horwitz M A. 2004. Two-plasmid system for stable, selective pressure-independent expression of multiple extracellular proteins in mycobacteria. Microbiology 150:2143-51, hereby incorporated by reference in its entirety).

2.a.i. rBCG-pGB9.2-30

This recombinant strain was generated by electroporating the recombinant plasmid pGB9.2 (Harth et al., 2004) consisting of the vector backbone and the *M. tuberculosis* 30 kDa protein gene (Rv1886c; fbpB) preceded by approximately 500 by of upstream DNA sequence (promoter region) and inserted into the PacI site of the plasmid's multi-cloning site, into BCG Tice bacteria (Stock #3). The strain stably maintained the recombinant plasmid, even in the absence of the selective antibiotic kanamycin for 4 months or approximately 120 generations. The recombinant strain was assayed for its capacity to express and secrete the recombinant 30 kDa protein by gel electrophoresis and immunoblotting with 30 kDa protein specific antisera. Analysis of digitized scans showed the secretion of 14 μg of 30 kDa protein by $5\times10^9$ CFU, a value about 3-fold higher than for wild-type BCG Tice (5.0 μg per $5\times10^9$ CFU). Stock vials (Stock #1) were established in 10% glycerol at a concentration of $5.0\times10^7$ particles/mL and stored at −80° C.

2.a.ii. rBCG-pGB9.2-23.5

This recombinant strain was generated by electroporating the recombinant plasmid pGB9.2 (Harth et al., 2004), consisting of the vector backbone and the *M. tuberculosis* 23.5 kDa protein gene (Rv1980; mpt64) preceded by approximately 625 by of upstream DNA sequence (promoter region) and inserted into the PacI site of the plasmid's multi-cloning site, into BCG Tice bacteria (Stock #3). The strain stably maintained the recombinant plasmid, even in the absence of the selective antibiotic kanamycin for 4 months or approximately 120 generations. The recombinant strain was assayed for its capacity to express and secrete the recombinant 23.5 kDa protein by gel electrophoresis and immunoblotting with 23.5 kDa protein specific antisera. Analysis of digitized scans showed the secretion of 2 μg of 23.5 kDa protein (wild-type BCG Tice does not contain a 23.5 kDa protein gene because the genomic deletion RD2, which occurred during the generation of BCG strains from wild-type *M. bovis* before 1931, eliminated approximately 11.5 kilobase (kb) *M. bovis* DNA, encompassing the corresponding *M. tuberculosis* genes Rv1978 to Rv1988). Stock vials (Stock #1) were established in 10% glycerol at a concentration of $5.0\times10^7$ particles/mL and stored at −80° C.

2.b.i. rBCG30 I (pMTB30)+pGB9.2-23.5

This recombinant strain was generated by electroporating the recombinant plasmid pGB9.2 (Harth et al., 2004), consisting of the vector backbone and the *M. tuberculosis* 23.5 kDa protein gene (Rv1980; mpt64) preceded by approximately 625 by of upstream DNA sequence (promoter region) and inserted into the PacI site of the plasmid's multi-cloning site, into rBCG30 Tice I bacteria (Stock #3). The strain stably maintained both recombinant plasmids, even in the absence of the selective antibiotics hygromycin and kanamycin for 4 months or approximately 120 generations. The recombinant strain was assayed for its capacity to express and secrete the recombinant 30 and 23.5 kDa proteins by gel electrophoresis and immunoblotting with 30 and 23.5 kDa protein specific antisera. Analysis of digitized scans showed the secretion of 28 μg of 30 kDa protein by $5\times10^9$ CFU, a value 5.6-fold higher than for wild-type BCG Tice (5.0 μg per $5\times10^9$ CFU), and 2 μg of 23.5 kDa protein (wild-type BCG Tice does not contain a 23.5 kDa protein gene because the genomic deletion RD2, which occurred during the generation of BCG strains from wild-type *M. bovis* before 1931, eliminated approximately 11.5 kb *M. bovis* DNA, encompassing the corresponding *M. tuberculosis* genes Rv1978 to Rv1988). Stock vials (Stock #1) were established in 10% glycerol at a concentration of $5.0\times10^7$ particles/mL and stored at −80° C.

2.b.ii. rBCG30 III (pNBV1-30)+pGB9.2-23.5

This recombinant strain was generated by electroporating the recombinant plasmid pGB9.2 consisting of the vector backbone and the *M. tuberculosis* 23.5 kDa protein gene (Rv1980; mpt64) preceded by approximately 625 bp of upstream DNA sequence (promoter region) and inserted into the PacI site of the plasmid's multi-cloning site, into rBCG30 Tice III (Stock #1). The strain stably maintained both recombinant plasmids, even in the absence of the selective antibiotics hygromycin and kanamycin for 4 months or approximately 120 generations. The recombinant strain was assayed for its capacity to express and secrete the recombinant 30 and 23.5 kDa proteins by gel electrophoresis and immunoblotting with 30 and 23.5 kDa protein specific antisera. Analysis of digitized scans showed the secretion of 34 µg of 30 kDa protein by $5 \times 10^9$ CFU, a value 6.8-fold higher than for wild-type BCG Tice (5.0 µg per $5 \times 10^9$ CFU), and 2 µg of 23.5 kDa protein (wild-type BCG Tice does not contain a 23.5 kDa protein gene because the genomic deletion RD2, which occurred during the generation of BCG strains from wild-type *M. bovis* before 1931, eliminated approximately 11.5 kb *M. bovis* DNA, encompassing the corresponding *M. tuberculosis* genes Rv1978 to Rv1988). Stock vials (Stock #1) were established in 10% glycerol at a concentration of $5.0 \times 10^7$ particles/mL and stored at −80° C.

3. Additional BCG Containing Constructs Expressing the *M. tuberculosis* 30/32 kDa Major Secretory Proteins alone and in combination (rBCG30 Tice I and rBCG32A Tice I are described below)
   a. rBCG32B Tice I
   b. rBCG30-32A (pNBV1-[30-32A])
   c. rBCG30-32A-32B (pNBV1-[30-32A-32B])

The 30/32 kDa protein complex (Antigen 85 complex) are major secreted proteins of *M. tuberculosis*. Previously, the present inventors have generated strains secreting the *M. tuberculosis* 30 kDa protein (Horwitz M A, Harth G. Dillon B J, and Malesa-Galic S. 2000. Recombinant BCG vaccines expressing the *Mycobacterium tuberculosis* 30 kDa major secretory protein induce greater protective immunity against tuberculosis than conventional BCG vaccines in a highly susceptible animal model. Proc. Natl. Acad. Sci. USA. 97:13853-8; Horwitz M A. and Harth G. 2003. A new vaccine against tuberculosis affords greater survival after challenge than the current vaccine in the guinea pig model of pulmonary tuberculosis. Infect. Immun. 71:1672-9; hereby incorporated by reference in their entirety). These vaccines secrete the other two members of the complex—the 32A (Antigen 85A) and 32B (Antigen 85C) kDa proteins. An additional strain secretes both the 30 and 32A kDa proteins—the two most abundant *M. tuberculosis* major secretory proteins (Horwitz M A, Lee B-W E, Dillon B J, and Harth G. 1995. Protective immunity against tuberculosis induced by vaccination with major extracellular proteins of *Mycobacterium tuberculosis*. Proc. Natl. Acad. Sci. USA. 92:1530-4, hereby incorporated by reference in its entirety). Another strain expresses all three of the *M. tuberculosis* 30/32 kDa complex proteins. By expanding the repertoire of *M. tuberculosis* major extracellular proteins presented to the host immune system in abundance, these latter strains are anticipated to induce a more potent immune response against *M. tuberculosis*.

3.a. rBCG32B Tice I

This recombinant strain was generated by electroporating the recombinant plasmid pNBV1, consisting of the vector backbone, a fragment of approximately 250 by located directly upstream of the atg codon of the 32B kDa protein gene (fbpC; Rv0129c) of *M. tuberculosis* Erdman and considered the promoter region of this gene, and the 1,020 by coding region of the 32B kDa protein gene, into BCG Tice bacteria.

3.b. rBCG30-32A (pNBV1-[30-32A])

This recombinant strain was generated by electroporating the recombinant plasmid pNBV1, consisting of the vector backbone, a HindIII-PacI fragment of approximately 1,500 bp, containing the *M. tuberculosis* Erdman 30 kDa protein gene promoter and coding regions (fbpB, Rv1886c), and a PacI-BamHI fragment of approximately 1,600 bp, containing the *M. tuberculosis* Erdman 32A kDa protein gene promoter and coding regions (fbpA, Rv3804c). The two genes are present on the recombinant plasmid in divergent orientation with regard to their 5'->3' sense DNA strands to prevent readthrough from one gene into the adjacent gene.

3.c. rBCG30-32A-32B (pNBV1-[30-32A-32B])

This recombinant strain was generated by electroporating the recombinant plasmid pNBV1, consisting of the vector backbone, a HindIII-PacI fragment of approximately 1,500 bp, containing the *M. tuberculosis* Erdman 30 kDa protein gene promoter and coding regions (fbpB, Rv1886c), a PacI-NdeI fragment of approximately 1,600 bp, containing the *M. tuberculosis* Erdman 32A kDa protein gene promoter and coding regions (fbpA, Rv3804c), and a NdeI-BamHI fragment of approximately 1,300 bp, containing the *M. tuberculosis* Erdman 32B kDa protein gene promoter and coding regions (fbpC, Rv0129c). The three genes are present on the recombinant plasmid in divergent orientation with regard to their 5'→3' sense DNA strands to prevent readthrough from one gene into an adjacent gene.

4. BCG Containing Constructs Expressing the 30 kDa Major Secretory Protein in Combination with Immunostimulatory Cytokines
   a. Cytokines Linked to *M. tuberculosis* 30 kDa Protein by Tether (Gly$_6$Ser)
      i. rBCG30-Gly$_6$Ser-GM-CSF(pNBV1-[30-G$_6$S-mGM-CSF])
      ii. rBCG30-Gly$_6$Ser-IFNγ (pNBV1-[30-G$_6$S-mIFNγ])
      iii. rBCG30-Gly$_6$Ser-IL2 (pNBV1-[30-G$_6$S-mIL2])
      iv. rBCG30-Gly$_6$Ser-IL12 (pNBV1-[30-G$_6$S-mIL12p40-G$_6$S-mIL12p35])
   b. Cytokines Fused to *M. tuberculosis* 30 kDa Protein
      i. rBCG30-GM-CSF-F (pNBV1-[30-mGM-CSF])
      ii rBCG30-IFNγ-F (pNBV1-[30-mIFNγ])
      iii. rBCG30-IL2-F (pNBV1-[30-mIL2])
      iv. rBCG30-IL12-F(pNBV1-[30-mIL12p40-G$_6$S-mIL12p35)

Certain host immunostimulatory cytokines have been shown to be important to the generation of a potent cell-mediated immune response to foreign antigens. These include the cytokines Granulocyte-Macrophage Colony Stimulating Factor (GM-CSF), Interferon gamma (IFNγ), Interleukin 2 (IL2), and Interleukin 12 (IL12). To boost the immune response to *M. tuberculosis* major extracellular proteins, in this case the 30 kDa protein, present inventors constructed recombinant BCG strains expressing one of these four human cytokines in combination with the 30 kDa protein. For each cytokine, two different constructs were engineered. In one construct the cytokine was fused directly to the 30 kDa protein. In the other, the cytokine was linked to the 30 kDa protein via a tether.

Strains of BCG secreting murine cytokines have previously been generated (O'Donnel M A, Aldovivi A, Duda R B, Yang H, Szilvasi A, Young R A, and DeWolf, W C. 1994. Recombinant *Mycobacterium bovis* BCG secreting functional interleukin-2 enhances gamma interferon production by splenocytes. Infect. Immun. 62:2508-14, hereby incorporated by reference in its entirety) but in contrast to the strains described here, the strains were not engineered to secrete human cytokines, and the strains were not designed to secrete the cytokines in association with *M. tuberculosis* extracellular proteins.

a. Cytokines Linked to *M. tuberculosis* 30 kDa Protein by Tether (Gly$_6$Ser)

4.a.i.  rBCG30-Gly$_6$Ser-GM-CSF  (pNBV1-[30-G$_6$S-mGM-CSF])

This recombinant strain was generated by electroporating the recombinant plasmid pNBV1, consisting of the vector backbone and a HindIII-BamHI fragment of approximately 1,900 by containing the *M. tuberculosis* Erdman 30 kDa protein gene promoter and coding regions without the gene's stop codon (fbpB, Rv1886c), a 21 by linker with six glycine and one serine specifying codons, and approximately 400 by containing the coding region of the mature human granulocyte-macrophage colony stimulating factor (GM-CSF) including this gene's stop codon, into BCG Tice bacteria (Stock #3). The fragment containing the DNA sequence of the mature GM-CSF was inserted into the recombinant plasmid as an amplification product using the recombinant ATCC construct #39754.

4.a.ii. rBCG30-Gly$_6$Ser-IFNγ (pN BV1-[30-G$_6$S-mIFNγ])

This recombinant strain was generated by electroporating the recombinant plasmid pNBV1, consisting of the vector backbone and a HindIII-BamHI fragment of approximately 1,950 by containing the *M. tuberculosis* Erdman 30 kDa protein gene promoter and coding regions without the gene's stop codon (fbpB, Rv1886c), a 21 by linker with six glycine and one serine specifying codons, and approximately 450 by containing the coding region of the mature human gamma interferon (IFNγ) including this gene's stop codon, into BCG Tice bacteria (Stock #3). The fragment containing the DNA sequence of the mature IFNγ was inserted into the recombinant plasmid as an amplification product using the recombinant ATCC construct #39046.

4.a.iii. rBCG30-Gly$_6$Ser-IL2 (pNBV1-[30-G$_6$S-mIL2])

This recombinant strain was generated by electroporating the recombinant plasmid pNBV1, consisting of the vector backbone and a HindIII-BamHI fragment of approximately 1,900 by containing the *M. tuberculosis* Erdman 30 kDa protein gene promoter and coding regions without the gene's stop codon (fbpB, Rv1886c), a 21 by linker with six glycine and one serine specifying codons, and approximately 400 by containing the coding region of the mature human interleukin 2 (IL2) including this gene's stop codon, into BCG Tice bacteria (Stock #3). The fragment containing the DNA sequence of the mature IL2 was inserted into the recombinant plasmid as an amplification product using the recombinant construct 9402pAHanti-HER2 (obtained from S. Morrison, UCLA).

iv. rBCG30-Gly$_6$Ser-IL12 (pNBV1-[30-G$_6$S-mIL12p40-G$_6$S-mIL12p35])

b. Cytokines Directly Fused to *M. tuberculosis* 30 kDa Protein i. rBCG30-GM-CSF-F (pNBV1-[30-mGM-CSF])
ii. rBCG30-IFNγ-F (pNBV1-[30-mIFNγ])
iii. rBCG30-IL2-F (pNBV1-[30-mIL2])
iv.  rBCG30-IL12-F  (pNBV1-[30-mIL12p40-G$_6$S-mIL12p35)

Strains 4. b. i, ii, iii, and iv parallel strains 4. a. i, ii, iii, and iv exactly with the exception that they do not contain the Gly$_6$Ser linker between the 30 kDa protein gene coding region and the mGM-CSF, mIFNγ, mIL2, and mIL12p40 coding regions.

5. BCG Containing Construct with Fusion of *M. tuberculosis* 30 kDa Major Secretory Protein and *M. tuberculosis* 23.5 kDa Major Secretory Protein
   a. rBCG30-23.5-F (pNBV1-[30-23.5-F])

Recombinant BCG expressing both the 30 and 23.5 kDa major secretory proteins on a single plasmid (see U.S. Pat. No. 6,599,510) or, as above, on separate compatible plasmids have been generated. In those constructs, the proteins were expressed individually. In this vaccine strain, the recombinant BCG expresses the two proteins as a fusion protein.

5.a. rBCG30-23.5-F (pNBV1-[30-23.5-F])

This recombinant strain was generated by electroporating the recombinant plasmid pNBV1, consisting of the vector backbone and a HindIII-BamHI fragment of approximately 2,200 by containing the *M. tuberculosis* Erdman 30 kDa protein gene promoter and coding regions without the gene's stop codon (fbpB, Rv1886c) and approximately 700 by containing the coding region of the mature *M. tuberculosis* 23.5 kDa protein (Rv1980; mpt64) including this gene's stop codon, into BCG Tice bacteria (Stock #3). The strain stably maintained the recombinant plasmid for approximately 9 months (approximately 270 generations) even in the absence of the selective antibiotic hygromycin. The recombinant strain was assayed for its capacity to express and secrete a recombinant 30-23.5 i.e. a 53 kDa fusion protein by gel electrophoresis and immunoblotting with 30 and 23.5 kDa protein specific antisera.

Analysis of digitized scans showed the secretion of 4.8 μg of 30 kDa protein by $1\times10^9$ CFU, a value approximately 5-fold higher than for wild-type BCG Tice (1.0 μg per $1\times10^9$ CFU), and 2.5 μg of 23.5 kDa protein (wild-type BCG Tice does not contain a 23.5 kDa protein gene because the genomic deletion RD2, which occurred during the generation of BCG strains from wild-type *M. bovis* before 1931, eliminated approximately 11.5 kb *M. bovis* DNA, encompassing the corresponding *M. tuberculosis* genes Rv1978 to Rv1988). Of the total amount of fusion protein synthesized, only approximately 1-2% are secreted as intact fusion molecules, because the junction of the two proteins restores an almost perfect signal peptide processing site. This combination leads to the interesting phenomenon that the 30 kDa protein portion is regarded by the secretion machinery of the bacteria as the leader peptide of the 23.5 kDa protein portion. Stock vials (Stock #1) were established in 10% glycerol at a concentration of $5.0\times10^7$ particles/mL and stored at −80° C.

6. BCG Containing Constructs Expressing *M. tuberculosis* or *M. smegmatis* Glutamine Synthetase (GS)
   a. rBCG-GS(MTB) (pNBV1-MtbGS)
   b. rBCG-GS(MS) (pNBV1-MsGS)

The present inventors have previously shown that major extracellular proteins of *M. tuberculosis* are potent immunoprotective antigens (Horwitz et al., 2000; Horwitz and Harth, 2003 and Horwitz et al., 1995). These vaccine strains over express the *M. tuberculosis* and *M. smegmatis* glutamine synthetase (GS), a protein that present inventors have shown is a major extracellular protein and an essential virulence factor of *M. tuberculosis* (Harth G, Clemens DL and Horwitz M A. 1994. Glutamine synthetase of *Mycobacterium tuberculosis*: extracellular release and characterization of its enzymatic activity. Proc. Natl. Acad. Sci. USA 91:9342-6; Harth G and Horwitz M A. 2003. Inhibition of *Mycobacterium tuberculosis* glutamine synthetase as a novel antibiotic strategy against *tuberculosis*: Demonstration of efficacy in vivo. Infect. Immun. 71:456-64; and Tullius M V, Harth G, and Horwitz M A. 2003. Glutamine synthetase GlnA1 is essential for growth of *Mycobacterium tuberculosis* in human THP-1 macrophages and guinea pigs. Infect. Immun. 71:3927-36; hereby incorporated by reference in their entirety).

6.a. rBCG-GS(MTB) (pNBV1-MtbGS)

The plasmid pNBV1-MtbGS (Tullius M V, Harth G and Horwitz M A. 2001. High extracellular levels of *Mycobacterium tuberculosis* glutamine synthetase and superoxide dismutase in actively growing cultures are due to high expression and extracellular stability rather than to a protein-specific export mechanism. Infect Immun. 69:6348-63, hereby incorporated by reference in its entirety) was electroporated into BCG Tice and transformants were selected on 7H11 agar containing 50 µg/mL hygromycin. Two individual hygromycin resistant clones were randomly selected and cultured in 7H9, 10% OADC, 0.05% Tween-80 (7H9-OADC-TW) medium containing 50 µg/mL hygromycin. Both clones were determined to be expressing large amounts of recombinant *M. tuberculosis* GS. To ensure a pure culture, one of the cultures was plated at low density and a single colony was reisolated. Initial freezer stocks of the strain were prepared from the reisolated clone. The expression of recombinant *M. tuberculosis* GS was verified by polyacrylamide gel electrophoresis and immunoblotting with polyvalent, highly specific rabbit anti-GS immunoglobulin. rBCG-GS(MTB) was found to produce approximately 9 times more GS per mL of culture than BCG Tice strains lacking the pNBV1-MtbGS plasmid.

6.b. rBCG-GS(MS) (pNBV1-MsGS)

The plasmid pNBV1-MsGS (Tullius et al., 2001) was electroporated into BCG Tice and transformants were selected on 7H11 agar containing 50 µg/mL hygromycin. Two individual hygromycin resistant clones were randomly selected and cultured in 7H9-OADC-TW medium containing 50 µg/mL hygromycin. One of the two clones was determined to be expressing large amounts of recombinant *M. smegmatis* GS. To ensure a pure culture, this culture was plated at low density and a single colony was reisolated. Initial freezer stocks of the strain were prepared from the reisolated clone.

The expression of recombinant *M. smegmatis* GS was verified by polyacrylamide gel electrophoresis and immunoblotting with polyvalent, highly specific rabbit anti-GS immunoglobulin. rBCG-GS(MS) was found to produce approximately 7 times more GS per mL of culture than BCG Tice strains lacking the pNBV1-MsGS plasmid.

7. Constructs Involving Over Expression of *M. tuberculosis* or *M. smegmatis* Superoxide Dismutase
   a. rBCG-SOD(MTB) (pNBV1-MtbSOD)
   b. rBCG-SOD(MS) (pNBV1-MsSOD)

As noted, present inventors have previously shown that major extracellular proteins of *M. tuberculosis* are potent immunoprotective antigens. These vaccine strains over express the *M. tuberculosis* and *M. smegmatis* superoxide dismutase (SOD), a protein that present inventors have shown is a major extracellular protein (Harth G and Horwitz M A. 1999. An inhibitor of exported *Mycobacterium tuberculosis* glutamine synthetase selectively blocks the growth of pathogenic mycobacteria in axenic culture and in human monocytes: Extracellular proteins as potential novel drug targets. J. Exp. Med. 189:1425-35, hereby incorporated by reference in its entirety).

7.a. rBCG-SOD(MTB) (pNBV1-MtbSOD)

The plasmid pNBV1-MtbSOD (Harth and Horwitz, 1999) was electroporated into BCG Tice and transformants were selected on 7H11 agar containing 50 µg/mL hygromycin. Two individual hygromycin resistant clones were randomly selected and cultured in 7H9-OADC-TW medium containing 50 µg/mL hygromycin. Both clones were determined to be expressing large amounts of recombinant *M. tuberculosis* SOD. To ensure a pure culture, one of the cultures was plated at low density and a single colony was reisolated. Initial freezer stocks of the strain were prepared from the reisolated clone.

The expression of recombinant *M. tuberculosis* SOD was verified by polyacrylamide gel electrophoresis and immunoblotting with polyvalent, highly specific rabbit anti-SOD immunoglobulin. rBCG-SOD was found to produce approximately 5 times more SOD per mL of culture than BCG Tice strains lacking the pNBV1-MtbSOD plasmid.

7.b. rBCG-SOD(MS) (pNBV1-MsSOD)

The plasmid pNBV1-MsSOD (Harth and Horwitz, 1999) was electroporated into BCG Tice and transformants were selected on 7H11 agar containing 50 µg/mL hygromycin. Two individual hygromycin resistant clones were randomly selected and cultured in 7H9-OADC-TW medium containing 50 µg/mL hygromycin. One of the two clones was determined to be expressing large amounts of recombinant *M. smegmatis* SOD. To ensure a pure culture, this culture was plated at low density and a single colony was reisolated. Initial freezer stocks of the strain were prepared from the reisolated clone.

The expression of recombinant *M. smegmatis* SOD was verified by polyacrylamide gel electrophoresis. rBCG-SOD (MS) was found to produce approximately 4 times more SOD per mL of culture than BCG Tice strains lacking the pNBV1-MsSOD plasmid.

8. Recombinant BCG30 TICE (rBCG30 Tice I)

Recombinant BCG TICE (rBCG30 Tice I) expressing the *M. tuberculosis* 30 kDa major extracellular non-fusion protein was prepared as follows. The plasmid pMTB30, a recombinant construct of the *E. coli*/mycobacteria shuttle plasmid pSMT3, was prepared as previously described by the present inventors in Harth et al. (Harth G, Lee B-Y and Horwitz M A. 1997. High-level heterologous expression and secretion in rapidly growing nonpathogenic mycobacteria of four major *Mycobacterium tuberculosis* extracellular proteins considered to be leading vaccine candidates and drug targets. Infect Immun 65:2321-8), the entire contents of which are hereby incorporated by reference.

9. Recombinant BCG30 Tice II (pNBV1-PglnA-MTB30)

Recombinant BCG30 Tice II (pNBV1-PglnA-MTB30), which over expresses the *M. tuberculosis* 30 kDa extracellular non-fusion protein, was prepared as follows. Plasmid pNBV1-PglnA1-MTB30 was constructed by amplifying the coding region of the *M. tuberculosis* 30 kDa gene (including an NdeI restriction site at the start codon and a HindIII restriction site immediately downstream of the stop codon) and cloning this PCR product downstream of the *M. tuberculosis* glnA1 promoter in the NdeI→HindIII sites of pNBV1-BFRB (Tullius et al., 2001). After confirming by restriction analysis that the plasmid was correct, the plasmid was electroporated into *M. bovis* BCG Tice and transformants were selected on 7H11 agar with 50 µg/mL hygromycin. Several individual hygromycin resistant clones were randomly selected and cultured in 7H9 medium containing 50 µg/mL hygromycin. The expression and export of recombinant *M. tuberculosis* 30 kDa protein were verified by polyacrylamide gel electrophoresis and immunoblotting with polyvalent, highly specific rabbit anti-30 kDa protein immunoglobulins. rBCG30 Tice II was found to produce 24 times more 30 kDa antigen per mL of culture than BCG Tice harboring just the vector (pNBV1).

10. Recombinant BCG23.5 Tice I (pNBV1-PglnA-MTB23.5)

Recombinant BCG23.5 Tice I (pNBV1-PglnA-MTB23.5), which over expresses the *M. tuberculosis* 23.5 kDa extracellular non-fusion protein, was prepared as follows. Plasmid pNBV1-PglnA1-MTB23.5 was constructed by amplifying the coding region of the *M. tuberculosis* 23.5 kDa gene (including an NdeI restriction site at the start codon and BamHI and HindIII restriction sites immediately downstream of the stop codon) and cloning this PCR product downstream of the *M. tuberculosis* glnA1 promoter in the NdeI→HindIII sites of pNBV1-BFRB (Tullius et al., 2001). After confirming by restriction analysis that the plasmid was correct, the plasmid was electroporated into *M. bovis* BCG Tice and transformants were selected on 7H11 agar with 50 μg/mL hygromycin. Several individual hygromycin resistant clones were randomly selected and cultured in 7H9 medium containing 50 μg/mL hygromycin. The expression and export of recombinant *M. tuberculosis* 23.5 kDa protein were verified by polyacrylamide gel electrophoresis and immunoblotting with polyvalent, highly specific rabbit anti-23.5 kDa protein immunoglobulins. rBCG23.5 Tice I produced the 23.5 kDa protein at a high level that was equivalent to or slightly greater than the amount of recombinant 30 kDa protein produced by rBCG30 Tice II. Because BCG does not have a gene encoding the 23.5 kDa protein, no comparison could be made to the parental strain as was done for the 30 kDa protein. (BCG Tice does not express a 23.5 kDa protein because of the RD2 genomic deletion of approximately 11.5 kb, which encompasses the corresponding *M. tuberculosis* genes Rv1978 to Rv1988 [23.5 kDa protein gene=Rv 1980]; the deletion occurred during the generation of BCG strains from wild-type *M. bovis* before 1931).

11. Recombinant BCG30/23.5 Tice I (pNBV1-PglnA-MTB30/23.5)

Recombinant BCG30/23.5 Tice I (pNBV1-PglnA-MTB30/23.5), which over expresses the *M. tuberculosis* 30 kDa and 23.5 kDa extracellular non-fusion protein, was prepared as follows. Plasmid pNBV1-PglnA1-MTB30/23.5 was constructed by cloning a 1 kb BamHI fragment from pNBV1-PglnA1-MTB23.5 (which includes the *M. tuberculosis* glnA1 promoter and the 23.5 kDa coding region in their entirety) into the unique BamHI site of pNBV1-PglnA1-MTB30. The genes encoding the two proteins are oriented in the same direction on the plasmid with the gene encoding the 23.5 kDa protein upstream of the gene encoding the 30 kDa protein. After confirming by restriction analysis that the plasmid was correct, the plasmid was electroporated into *M. bovis* BCG Tice and transformants were selected on 7H11 agar with 50 μg/mL hygromycin. Several individual hygromycin resistant clones were randomly selected and cultured in 7H9 medium containing 50 μg/mL hygromycin. The expression and export of recombinant *M. tuberculosis* 30 kDa and 23.5 kDa proteins were verified by polyacrylamide gel electrophoresis and immunoblotting with polyvalent, highly specific rabbit anti-30 kDa protein and anti-23.5 kDa protein immunoglobulins. rBCG30/23.5 Tice I was found to produce 24 times more 30 kDa antigen per mL of culture than BCG Tice harboring just the vector (pNBV1). This strain also produced the 23.5 kDa protein at a high level that was slightly greater than the amount of recombinant 30 kDa protein. Because BCG does not have a gene encoding the 23.5 kDa protein, no comparison could be made with the parental strain as was done for the 30 kDa protein.

12. Recombinant BCG30 Tice III (pNBV1-MTB30)

Recombinant BCG30 Tice III (pNBV1-MTB30), which over expresses the *M. tuberculosis* 30 kDa major extracellular protein, was prepared as follows. This recombinant strain was generated by electroporating the recombinant plasmid pNBV1, consisting of the vector backbone and an approximately 1.5 kb *M. tuberculosis* Erdman DNA flanked by ClaI and BamHI restriction sites and containing the coding region of the 30 kDa major extracellular protein and the promoter region immediately upstream of the coding region, into BCG Tice bacteria (Stock #2). The strain stably maintained the recombinant plasmid, and the level of recombinant 30 kDa protein expression remained almost constant over a 12 month period in the absence of antibiotics, as confirmed by immunoblotting with 30 kDa protein specific antisera (14.4-fold over the BCG Tice wild-type background level at the beginning of the analysis and 11.5-fold at the end of the analysis). A stock (Stock #1) was established in 10% glycerol at a concentration of $2.5\times10^8$ particles/mL and stored at −80° C.

13. Recombinant BCG23.5 Tice II (pNBV1-MTB23.5)

Recombinant BCG23.5 Tice II (pNBV1-MTB23.5), which over expresses the *M. tuberculosis* 30 kDa major extracellular protein, was prepared as follows. This recombinant strain was generated by electroporating the recombinant plasmid pNBV1, consisting of the vector backbone and a approximately 1.4 kb *M. tuberculosis* Erdman DNA flanked by PstI and BamHI restriction sites and containing the coding region of the 23.5 kDa major extracellular protein and the promoter region immediately upstream of the coding region, into BCG Tice bacteria (Stock #2). The strain stably maintained the recombinant plasmid, and the level of recombinant 23.5 kDa protein expression remained almost constant over a 12 month period in the absence of antibiotics, as confirmed by immunoblotting with 23.5 kDa protein specific antisera (16.2 mg/L at the beginning of the analysis and 15.1 mg/L at the end of the analysis. Because BCG does not have a gene encoding the 23.5 kDa protein, no comparison could be made with the parental strain as was done for the 30 kDa protein. A stock (Stock #1) was established on 08-24-2001 in 10% glycerol at a concentration of $3\times10^8$ particles/mL and stored at −80° C.

14. Recombinant BCG30/23.5 Tice IIA (pNBV1-MTB30/23.5↑↑)

Recombinant BCG30/23.5 Tice IIA (pNBV1-MTB30/23.5↑↑) (as used hereinafter "↑↑" refers to a genetic construct encoding for multiple major extracellular proteins where in the nucleic acid sequences encoding for each protein [genes] are orientated in the same direction relative to the 5' end of the genetic construct) over expresses both the *M. tuberculosis* 30 kDa and 23.5 kDa major extracellular proteins. The genes encoding the two proteins are oriented in the same direction. This recombinant strain was generated by electroporating the recombinant plasmid pNBV1, consisting of the vector backbone and two pieces of *M. tuberculosis* Erdman DNA of approximately 1.5 and approximately 1.4 kb, flanked by ClaI and NdeI (30 kDa protein gene and promoter) and NdeI and NdeI-BamHI (23.5 kDa protein gene and promoter) restriction sites and containing the coding and promoter regions immediately upstream of each of the two coding regions of the 30 and 23.5 kDa major extracellular proteins, into BCG Tice bacteria (Stock #2). The strain stably maintained the recombinant plasmid, and the level of recombinant 30 and 23.5 kDa protein expression remained almost constant over a 12 month period in the absence of antibiotics, as confirmed by immunoblotting with 30 and 23.5 kDa protein specific antisera (for the 30 kDa protein, expression was 23.3-fold over the BCG Tice wild-type background level at the beginning of the analysis and 16.5-fold over the BCG Tice wild-type background level at the end of the analysis; for the 23.5 kDa protein, expression was 18.7 mg/L at the beginning of the analysis and 12.2 mg/L at the end of the analysis). As mentioned above, expression of the recombinant 23.5 kDa protein is measured in absolute terms because BCG Tice does not express a 23.5 kDa protein. A stock (Stock #1) was established in 10% glycerol at a concentration of $3\times10^8$ particles/mL and stored at −80° C.

15. Recombinant BCG30/23.5 Tice IIB (pNBV1-MTB30/23.5↑↓)

Recombinant BCG30/23.5 Tice IIB (pNBV1-MTB30/23.5↑↓) (as used hereinafter "↑↓" refers to a genetic construct encoding for multiple major extracellular proteins where in the nucleic acid sequences encoding for each protein [genes] are orientated in the opposite direction relative to the 5' end of the genetic construct) over expresses both the *M. tuberculosis* 30 kDa and 23.5 kDa major extracellular proteins. The genes encoding the two proteins are oriented in opposite directions on the plasmid. This recombinant strain was generated by electroporating the recombinant plasmid pNBV1, consisting of the vector backbone and two pieces of *M. tuberculosis* Erdman DNA of approximately 1.5 and approximately 1.4 kb, flanked by ClaI and NdeI (30 kDa protein gene and promoter) and NdeI and NdeI-BamHI (23.5 kDa protein gene and promoter) restriction sites and containing the coding and promoter regions immediately upstream of the coding regions of the 30 and 23.5 kDa major extracellular proteins, into BCG Tice bacteria (Stock #2). In contrast to the strain described just above (rBCG30/23.5 Tice IIA), the orientation of the NdeI restriction fragment carrying the coding and promoter region of the 23.5 kDa protein was inverted. The strain stably maintained the recombinant plasmid, and the level of recombinant 30 and 23.5 kDa protein expression remained almost constant over a 12 month period in the absence of antibiotics, as confirmed by immunoblotting with 30 and 23.5 kDa protein specific antisera. (For the 30 kDa protein, expression was 25.7-fold over the BCG Tice wild-type background level at the beginning of the analysis and 21.1-fold over the BCG Tice wild-type background level at the end of the analysis; for the 23.5 kDa protein, expression was 16.6 mg/L at the beginning of the analysis and 12.8 mg/L at the end of the analysis). As mentioned above, expression of the recombinant 23.5 kDa protein is measured in absolute terms because BCG Tice does not express a 23.5 kDa protein. A stock (Stock #1) was established in 10% glycerol at a concentration of $3 \times 10^8$ particles/mL and stored at $-80°$ C.

16. Recombinant BCG32A Tice I (pNBV1-MTB32A)

Recombinant BCG32A Tice I (pNBV1-MTB32A), which over expresses the *M. tuberculosis* 32A kDa major extracellular protein (a.k.a. Antigen 85A), was prepared as follows. This recombinant strain was generated by electroporating the recombinant plasmid pNBV1, consisting of the vector backbone and a approximately 1.5 kb piece of *M. tuberculosis* Erdman DNA flanked by ClaI and BamHI restriction sites and containing the coding region of the 32A kDa major extracellular protein and the promoter region immediately upstream of the coding region, into BCG Tice bacteria (Stock #2). The strain stably maintained the recombinant plasmid, and the level of recombinant 32A kDa protein expression remained almost constant over a 12 month period in the absence of antibiotics, as confirmed by immunoblotting with 32A kDa protein specific antisera (10.5-fold over the BCG Tice wild-type background level at the beginning of the analysis and 8.1-fold at the end of the analysis). A stock (Stock #1) was established in 10% glycerol at a concentration of $3 \times 10^8$ particles/mL and stored at $-80°$ C.

17. Recombinant BCG(MB)30 Tice (pNBV1-MB30)

Recombinant BCG(MB)30 Tice (pNBV1-MB30), which over expresses the *M. bovis* 30 kDa major extracellular protein, was prepared as follows. This recombinant strain was generated by electroporating the recombinant plasmid pNBV1, consisting of the vector backbone and a approximately 1.5 kb piece of *M. bovis* wild-type (ATCC#19210) DNA flanked by ClaI and BamHI restriction sites and containing the coding region of the 30 kDa major extracellular protein and the promoter region immediately upstream of the coding region, into BCG Tice bacteria (Stock #2). The strain stably maintained the recombinant plasmid, and the level of recombinant 30 kDa protein expression remained almost constant over a 12 month period in the absence of antibiotics, as confirmed by immunoblotting with 30 kDa protein specific antisera (9.7-fold over the BCG Tice wild-type background level at the beginning of the analysis and 7.8-fold at the end of the analysis). A stock (Stock #2) was established in 10% glycerol at a concentration of $2.5 \times 10^8$ particles/mL and stored at $-80°$ C.

18. Recombinant BCG(ML)30 Tice (pNBV1-ML30)

Recombinant BCG(ML)30 Tice (pNBV1-ML30), which expresses the *M. leprae* 30 kDa major extracellular protein, was prepared as follows. This recombinant strain was generated by electroporating the recombinant plasmid pNBV1, consisting of the vector backbone and a approximately 1.3 kb piece of *M. leprae* DNA flanked by ClaI and BamHI restriction sites and containing the coding region of the 30 kDa major extracellular protein and the promoter region immediately upstream of the coding region, into BCG Tice bacteria (Stock #2). The strain stably maintained the recombinant plasmid, and the level of recombinant 30 kDa protein expression remained almost constant over a 12 month period in the absence of antibiotics, as confirmed by immunoblotting with 30 kDa protein specific antisera (9.7-fold over the BCG Tice wild-type background level at the beginning of the analysis and 9.3-fold at the end of the analysis). A stock (Stock #1) was established in 10% glycerol at a concentration of $3 \times 10^8$ particles/mL and stored at $-80°$ C.

B. Immunogenic Compositions Suitable for use in Immunocompromised Vaccinees: Growth Regulatable rBCG In another embodiment of the present invention the attenuated intracellular pathogen is a growth regulatable auxotroph or metabolically impaired organism hereinafter referred to collectively as growth regulatable immunogenic compositions. Exemplary embodiments of the present invention are based on attenuated or avirulent recombinant BCG. However, the present invention is not limited to recombinant BCG.

When a growth regulatable immunogenic composition is an auxotroph it remains essentially immunologically inert until a sufficient quantity of the appropriate nutrient is provided to the host. Once the essential nutrient is provided, the auxotrophic immunogenic composition begins expressing and secreting the immunogen. Later, if desired, withholding the essential nutrient can halt the auxotroph's growth and antigen expression in situ.

When the immunogenic compositions of the present invention utilize an auxotrophic transformant expressing an immunogen, the essential nutrient required to initiate the auxotroph's growth within the host can be administered either immediately before, concurrent with or immediately after the immunogenic composition is administered. It is also within the scope of the present invention to delay administration of the essential nutrient days or even weeks following administration of the immunogenic composition. Furthermore, the essential nutrient can be withheld from the host at any time following administration of the immunogenic composition to stop proliferation of the auxotrophic transformant.

In another embodiment of the present invention the growth regulatable immunogenic composition is metabolically impaired such that the immunogenic composition is only able to multiply for a finite number of generations. For example, in one embodiment, the growth regulatable immunogenic composition is a siderophore mutant that does not express the gene required for mycobactin or exochelin production. Consequently, the siderophore mutant cannot transport essential minerals such as iron into the cell. When the siderophore mutant is cultivated with an exogenous source of siderophore and iron the growth regulatable immunogenic composition becomes "pre-loaded" with the required mineral. After it has been introduced into the vaccinee the siderophore mutant will multiply through a finite number of divisions until the stored iron is depleted at which time multiplication ceases. However, during multiplication the siderophore mutant will continue to express genes encoding for selected immunogens located on extrachromosomal plasmids.

B.1. Mutant BCG Defective in Iron Acquisition (Siderophore Mutant)

a. rBCG-mbtB

B.2. Mutant BCG Defective in Iron Acquisition Over Expressing the *M. tuberculosis* 30 kDa Major Secretory Protein a. rBCG-mbtB-30 (pMTB30)

BCG sometimes can cause serious and even fatal disease in immunocompromised persons such as AIDS patients. Yet these patients are in great need of a tuberculosis vaccine because they are approximately 100-fold more susceptible to tuberculosis than immunocompetent persons. To circumvent the problem of BCG disseminating and causing disease in such patients, the present inventors previously engineered auxotrophs that require a nutritional supplement to grow in the vaccinated host. Therefore, if the vaccine begins to disseminate and cause disease, the vaccinated person need only stop taking the nutritional supplement to stop the vaccine from multiplying.

Another approach to this problem is to engineer a vaccine capable of undergoing only a limited number of multiplications—a number sufficient to induce a strong immune response but not harm the host. The vaccines described here are such constructs. These BCG vaccines have a defect in siderophore production and hence in iron acquisition. However, if cultured in the presence of iron and a mycobacterial siderophore, the bacteria can be iron-loaded with a sufficient amount of iron so that they subsequently are able to multiply for several generations in the absence of a siderophore. Thus, when the iron-loaded bacteria are administered to the host, the bacteria have a sufficient amount of stored iron to multiply for several generations and induce an immune response. However, lacking a siderophore, the organism can not acquire iron from the host to replenish the iron utilized in multiplication (Gobin, J., Moore, C. H., Reeve, Jr., J. R., Wong, D. K., Gibson, B. W., and Horwitz M. A. 1995. Iron acquisition by *Mycobacterium tuberculosis*: Isolation and characterization of a family of iron-binding exochelins. Proc. Natl. Acad. Sci. (USA) 92:5189-93). Eventually, the iron stores of the bacteria are depleted, and the bacteria are no longer able to multiply. Thus the bacteria are unable to cause serious disease in the immunocompromised host.

Present inventors have generated two different strains of BCG defective in iron acquisition. One is a BCG vaccine with a defect in siderophore production only. The other is a recombinant BCG vaccine with the same defect but containing a plasmid that allows it to over express the *M. tuberculosis* 30 kDa major secretory protein.

B.1.a. rBCG-mbtB

The BCG Tice mbtB gene was disrupted via allelic exchange. The allelic exchange substrate was generated using a PCR strategy in which a BCG Tice mbtB locus with a 3.9 kb deletion was created and a $Km^r$ cassette was inserted at the site of the deletion. This mutated allele was cloned into the allelic exchange vector pEX2 (a derivative of pEX1 [Tullius et al., 2003] in which the gfpuv gene, encoding green fluorescent protein, is replaced by the *E. coli* codBA operon, encoding cytosine deaminase) to generate pEX2 ΔmbtB::$Km^r$. The codBA operon incorporated into the pEX2 plasmid allows for the positive selection of clones that have lost the plasmid using 5-fluorocytosine (5-FC), that CodA converts to the highly toxic 5-fluorouracil.

pEX2 ΔmbtB::$Km^r$ was electroporated into BCG Tice and transformants were selected on 7H11 containing 50 μg/mL hygromycin and 50 μg/mL kanamycin at the permissive temperature (32° C.). Pooled transformants were grown in 7H9-OADC-TW broth containing 50 μg/mL hygromycin and 50 μg/mL kanamycin at the permissive temperature for approximately 10 generations. After 10-40 generations of further growth at the permissive temperature in 7H9-OADC-TW containing 10 μg/mL kanamycin, the culture was plated on 7H10 containing 10 or 50 μg/mL kanamycin and 2% (w/v) sucrose or 2% (w/v) sucrose plus 1-10 μM 5-FC at the restrictive temperature (39° C.) to select for clones that had undergone a homologous recombination event. Twenty-nine out of the 76 clones analyzed were found to be hygromycin sensitive indicating that the plasmid had been eliminated. Of these 29, only one appeared to have the correct genotype, as determined by Southern blotting, for an mbtB mutant. However, further growth of the clone indicated that the culture was likely a mixture of the mbtB mutant and wild-type cells that had become spontaneously resistant to kanamycin (not uncommon in mycobacteria) as the culture seemed to revert to a wild-type genotype. The present inventors then hypothesized that the mbtB mutant is actually a mycobactin auxotroph that can grow for a limited amount of time in the absence of mycobactin, but eventually stops growing, thus allowing the wild-type cells in the population to dominate the culture. This was not expected as a previously characterized *M. tuberculosis* H37Rv mbtB mutant was reported to grow in broth medium without mycobactin (De Voss, J. J., Rutter, K., B. G. Schroeder, Su, H., Zhu, Y., and Barry, III, C. E. 2000, The salicylate-derived mycobactin siderophores of *Mycobacterium tuberculosis* are essential for growth in macrophages. Proc. Natl. Acad. Sci. (USA) 97:1252-1257). Therefore, the present inventors cultured the strain in the presence of mycobactin J and performed three rounds of colony purification in order to isolate a pure, and stable, clone. This was successful, and initial freezer stocks of the strain were prepared from this reisolated clone. The correct genotype of the mutant was confirmed by Southern blot analysis.

As discussed above, the rBCG-mbtB strain is indeed a mycobactin auxotroph. Growth of the strain is normal in 7H9-OADC-TW when supplemented with more than 20 ng/mL mycobactin J and growth is reduced at 2 ng/mL. At less than 0.2 ng/mL mycobactin J there is no visible growth. Although rBCG-mbtB is a mycobactin auxotroph, the strain can multiply for several or many generations after removal of mycobactin J. The number of generations of growth is dependent on the level of mycobactin J in the medium in which the strain was initially grown. So, when the strain is grown in 7H9-OADC-TW supplemented with a high concentration of mycobactin J (10 or 20 μg/mL) and the cells washed to remove extracellular mycobactin J, the strain is capable of approximately 8 or 9 generations of growth in medium lacking mycobactin J. When the strain is grown in the presence of 2 μg/mL mycobactin J, there is essentially no growth upon subculture of washed cells into medium lacking mycobactin J. Finally, if the strain is grown in the presence of less than 0.5 μg/mL mycobactin J and subcultured into medium lacking mycobactin J, there is a drop in viability of approximately 3 logs in 2 weeks. Complementation analysis was also performed by transforming rBCG-mbtB with a plasmid containing the BCG Tice mbtB gene (pNBV1-mbtB). This plasmid restored a wild-type growth phenotype to the mutant.

B.2.a. rBCG-mbtB-30 (pMTB30)

The plasmid pMTB30 (pSMT3-30) was electroporated into rBCG-mbtB and transformants were selected on 7H11 agar with 50 µg/mL hygromycin, 10 µg/mL kanamycin, and 2 µg/mL mycobactin J. Four individual hygromycin and kanamycin resistant clones were randomly selected and cultured in 7H9 medium containing 50 μg/mL hygromycin and 2 μg/mL mycobactin J. rBCG-mbtB-30, like its parent strain rBCG-mbtB, is a mycobactin auxotroph.

B. 3. Auxotrophic rBCG a. rBCG Tice glnA1

The BCG Tice glnA1 gene was disrupted via allelic exchange using the plasmid pEX1-Mtb-glnA1::$Km^r$ which present inventors previously used to generate a *M. tuberculosis* glnA1 mutant (Tullius et al., 2003). pEX1-Mtb-glnA1::$Km^r$ was derived from the temperature sensitive-sacB vector, pPR27, and contains a $hyg^r$ gene and a 1.8 kb fragment containing the *M. tuberculosis* glnA1 locus with a $Km^r$ cassette inserted into a unique site located near the middle of the glnA1 coding region. (Pelicic, V., M. Jackson, J. M. Reyrat, W. R. Jacobs, Jr., B. Gicquel, and C. Guilhot. 1997. Efficient allelic exchange and transposon mutagenesis in *Mycobacterium tuberculosis*. Proc. Natl. Acad. Sci. USA 94:10955-10960.) pEX1-Mtb-glnA1::$Km^r$ was electroporated into BCG Tice and transformants were selected on 7H11 containing 50 μg/mL hygromycin. The plates were initially kept at the permissive temperature (32° C.) for 6 days and then incubated at the restrictive temperature (39° C.) for 46 days. A single transformant was grown in 7H9-10% OADC-0.05% Tween-80 broth culture with 50 μg/mL kanamycin and 20 mM L-glutamine at the restrictive temperature for approximately 25 generations and then plated on 7H11 containing 2% (w/v) sucrose, 20 mM L-glutamine, and 50 μg/mL kanamycin to select for clones that had undergone a second homologous recombination event. Twelve of 35 randomly selected $Km^r$ clones were found to have the correct phenotype (i.e. $Hyg^s$ and glutamine auxotroph). To ensure a pure culture, present inventors plated one of the twelve clones at low density and a single colony was reisolated. Initial freezer stocks of the strain were prepared from the reisolated clone. The correct genotype of the mutant was confirmed by Southern blot analysis.

The BCG Tice glnA1 strain is a glutamine auxotroph. No growth was observed on 7H11 plates without the addition of L-glutamine. Furthermore, the glnA1 mutant displayed little or no intracellular growth in human macrophages when macrophages were cultured in tissue culture medium containing 0.2 mM L-glutamine (conditions under which the wild-type strain grows normally). However, intracellular growth similar to the wild-type strain was achieved by adding a large excess of L-glutamine (10 mM) to the tissue culture medium. Complementation analysis was performed by transforming BCG Tice glnA1 with plasmids containing the *M. tuberculosis* glnA1 gene (pNBV1-MtbGS) or the *S. typhimurium* glnA gene (pNBV1-StGS). Both plasmids restored a wild-type growth phenotype to the mutant. The L-glutamine requirement of this BCG glnA1 auxotroph is expected to be very similar to that of a *M. tuberculosis* glnA1 strain that the present inventors have previously characterized in greater detail (Tullius et al., 2003). In the case of the *M. tuberculosis* glnA1 strain, high levels of L-glutamine (10-20 mM) were required in solid medium for the mutant to grow normally. In liquid medium, the *M. tuberculosis* glnA1 mutant grew at a normal growth rate at more than 1 mM L-glutamine. Although initially growth was normal at 1-2 mM L-glutamine, these cultures did not reach as high a density as cultures containing 5 mM and 20 mM L-glutamine, and they exhibited a sharp drop in viability shortly after log-phase. The *M. tuberculosis* glnA1 strain lost viability rapidly when diluted into medium lacking L-glutamine. No growth of the *M. tuberculosis* glnA1 mutant occurred in human macrophages when the macrophages were cultured in the presence of 0.2 mM L-glutamine, a condition under which the wild-type strain grows normally. Growth of the *M. tuberculosis* glnA1 mutant in human macrophages was poor when macrophages were cultured in standard tissue culture medium containing 2 mM L-glutamine. However, intracellular growth similar to the wild-type strain was achieved when macrophages were cultured in a large excess of L-glutamine (10 mM). The *M. tuberculosis* glnA1 mutant is highly attenuated in the guinea pig model of pulmonary tuberculosis.

B.3.b. BCG Tice trpD

The BCG Tice trpD gene was disrupted via allelic exchange. The allelic exchange substrate was generated using a PCR strategy in which a BCG Tice trpD locus with a 588 by deletion was created and a $Km^r$ cassette was inserted at the site of the deletion. This mutated allele was cloned into the allelic exchange vector pEX2 (a derivative of pEX1 in which the gfpuv gene, encoding green fluorescent protein, is replaced by the *E. coli* codBA operon, encoding cytosine deaminase) to generate pEX2 ΔtrpD::$Km^r$ (Tullius et al., 2003).

pEX2 ΔtrpD::$Km^r$ was electroporated into BCG Tice and transformants were selected on 7H11 containing 50 μg/mL hygromycin at the permissive temperature (32° C.). Pooled transformants were grown in 7H9-10% OADC-0.05% Tween-80 broth culture with 10 μg/mL kanamycin and 50 μg/mL L-tryptophan at the permissive temperature for approximately 10 generations and then plated on 7H10 containing 2% (w/v) sucrose, 50 μg/mL kanamycin, and 50 μg/mL L-tryptophan at the restrictive temperature (39° C.) to select for clones that had undergone a homologous recombination event. Four of 10 selected $Km^r$ clones were found to have the correct phenotype (i.e. $Hyg^s$ and tryptophan auxotroph). To ensure a pure culture, one of the four clones was plated at low density and a single colony was reisolated. Initial freezer stocks of the strain were prepared from the reisolated clone. The correct genotype of the mutant was confirmed by Southern blot analysis.

The BCG Tice trpD strain is a tryptophan auxotroph. No growth was observed on 7H11 plates without the addition of L-tryptophan. In broth culture, the BCG Tice trpD strain grew at a rate similar to the wild-type strain in the presence of more than 10 μg/mL L-tryptophan. Growth was nearly twice as slow at 3 μg/mL L-tryptophan and the strain lost viability when diluted into medium lacking L-tryptophan. The trpD mutant displayed little or no intracellular growth in human macrophages when macrophages were cultured in standard tissue culture medium which contains 5 μg/mL L-tryptophan (conditions under which the wild-type strain grows normally). However, intracellular growth similar to the wild-type strain was achieved by adding an additional 100 μg/mL L-tryptophan to the tissue culture medium. Complementation analysis was performed by transforming BCG Tice trpD with a plasmid containing the BCG Tice trpD gene (pNBV1-trpD). This plasmid restored a wild-type growth phenotype to the mutant.

B.3c. BCG Tice glnA1 pSMT3-MTB30

The plasmid pMTB30 (pSMT3-30) was electroporated into BCG Tice glnA1 and transformants were selected on 7H11 agar with 50 μg/mL hygromycin, 50 μg/mL kanamycin, and 20 mM L-glutamine. Two individual hygromycin and kanamycin resistant clones were randomly selected and cultured in 7H9 medium containing 50 μg/mL hygromycin, 50 μg/mL kanamycin, and 20 mM L-glutamine. The expression and export of recombinant *M. tuberculosis* 30 kDa protein were verified by polyacrylamide gel electrophoresis and immunoblotting with polyvalent, highly specific rabbit anti-30 kDa protein immunoglobulins. BCG Tice glnA1 pMTB30 was found to produce approximately 10-20 times more 30 kDa antigen per mL of culture than BCG Tice glnA1. BCG Tice glnA1 pMTB30, like its parent strain BCG Tice glnA1, is a glutamine auxotroph.

B.3.d. BCG Tice trpD pSMT3-MTB30

The plasmid pMTB30 (pSMT3-30) was electroporated into BCG Tice trpD and transformants were selected on 7H11 agar with 50 μg/mL hygromycin, 50 μg/mL kanamycin, and 50 μg/mL L-tryptophan. Ten individual hygromycin and kanamycin resistant clones were randomly selected and cultured in 7H9-10% OADC-0.05% Tween-80 broth containing 50 μg/mL hygromycin, 50 μg/mL kanamycin, and 50 μg/mL L-tryptophan. The expression of recombinant *M. tuberculosis* 30 kDa protein was verified by polyacrylamide gel electrophoresis and immunoblotting with polyvalent, highly specific rabbit anti-30 kDa protein immunoglobulin. BCG Tice trpD pMTB30 was found to produce approximately 10-20 times more 30 kDa antigen per mL of culture than a control BCG Tice strain.

B.4. Attenuated BCG (Prototroph)

a. BCG Tice narG

The BCG Tice narG gene (encoding nitrate reductase alpha subunit) was disrupted via allelic exchange. The allelic exchange substrate was generated using a polymerase chain reaction (PCR) strategy in which a BCG Tice narG locus with a 2952 by deletion was created and a $Km^r$ cassette was inserted at the site of the deletion. This mutated allele was cloned into the allelic exchange vector pEX2 (a derivative of pEX1 in which the gfpuv gene is replaced by the *E. coli* codBA operon) to generate pEX2 ΔnarG::$Km^r$ (Tullius et al., 2003).

pEX2 ΔnarG::$Km^r$ was electroporated into BCG Tice and transformants were selected on 7H11 agar containing 50 μg/mL hygromycin and 50 μg μg/mL kanamycin at the permissive temperature (32° C.). Pooled transformants were grown in 7H9-10% OADC-0.05% Tween-80 broth culture with 10 μg/mL kanamycin at the permissive temperature for approximately 30 generations and then plated on 7H10 agar containing 2% (w/v) sucrose and 10 μg/mL kanamycin at the restrictive temperature (39° C.) to select for clones that had undergone a homologous recombination event. Eight of 8 selected $Km^r$ clones were found to have the correct phenotype (i.e. $Hyg^s$). To ensure a pure culture, one of the eight clones was plated at low density and a single colony was reisolated. Initial freezer stocks of the strain were prepared from the reisolated clone. The correct genotype of the mutant was confirmed by Southern blot analysis, demonstrating that the mutant lacked a full length narG gene. The narG mutant grows normally on plates, in broth culture, and intracellularly in macrophages. However, a BCG narG mutant generated elsewhere has been reported to be highly attenuated, compared with the parent BCG strain, in an immunodeficient SCID mouse model (Weber I, Fritz C, Ruttkowski S, Kreft A, and Bang F C. 2000. Anaerobic nitrate reductase (narGHJI) activity of *Mycobacterium bovis* BCG in vitro and its contribution to virulence in immunodeficient mice. Mol. Microbiol. 35:1017-25). Hence, it is anticipated that the narG mutant strain will similarly be attenuated in SCID mice and, in addition, be attenuated in immunocompromised persons.

B.4.b. BCG Tice narG pSMT3-MTB30

The plasmid pMTB30 (pSMT3-30) was electroporated into BCG Tice narG and transformants were selected on 7H11 agar with 50 μg/mL hygromycin and 10 μg/mL kanamycin. Five individual hygromycin and kanamycin resistant clones were randomly selected and cultured in 7H9-10% OADC-0.05% Tween-80 broth containing 50 μg/mL hygromycin. The expression of recombinant *M. tuberculosis* 30 kDa protein was verified by polyacrylamide gel electrophoresis and immunoblotting with polyvalent, highly specific rabbit anti-30 kDa protein immunoglobulins. BCG Tice narG pMTB30 was found to produce approximately 10-20 times more 30 kDa antigen per mL of culture than a control BCG Tice strain.

B.5. Mutant BcG Deficient in Pantothenate Biosynthesis a. rBCG-panCD

The BCG Tice panCD genes were disrupted via allelic exchange. The allelic exchange substrate was generated using a cloning strategy in which a panCD locus with a 1.3 kb deletion was created with an apramycin resistance ($apr^r$) gene inserted at the site of the deletion. This mutated allele was cloned into the allelic exchange vector phEX1 (a derivative of phAE87 [Bardarov S, Bardarov S Jr, Pavelka M S Jr, Sambandamurthy V, Larsen M, Tufariello J, Chan J, Hatfull G, Jacobs W R Jr. 2002. Specialized transduction: an efficient method for generating marked and unmarked targeted gene disruptions in *Mycobacterium tuberculosis*, *M. bovis* BCG and *M. smegmatis*. Microbiology. 148:3007-17]) to generate phEX1 ΔpanCD::$apr^r$. This plasmid was electroporated into *Mycobacterium smegmatis* to generate the specialized transducing phage as described in Bardorov et al., 2002. BCG Tice was infected with this purified phage and then plated on 7H10 containing 50 μg/mL apramycin and 50 50 μg/mL calcium D-pantothenate to select for clones that had undergone a homologous recombination event. Four apramycin resistant clones were obtained of which two were shown to be pantothenate auxotrophs. No growth was observed for the auxotrophs on plates or in broth without the addition of calcium D-pantothenate. In broth culture, the mutant strain grows at a rate similar to the wild-type strain in the presence of more than 10-50 μg/mL calcium D-pantothenate. To ensure a pure culture, one of the pantothenate auxotrophic clones was plated at low density and a single colony was reisolated. Initial freezer stocks of the strain were prepared from this reisolated clone.

III. Representative Methods for Plasmid and Transformant Preparation

Briefly, plasmid pMTB30 was engineered to express the *M. tuberculosis* Erdman 30 kDa major extracellular non-fusion protein from its own promoter (or any non-heat shock and non-stress protein gene promoter) by inserting a large genomic DNA restriction fragment containing the 30 kDa non-fusion protein gene plus extensive flanking DNA sequences into the plasmid's multi-cloning site using methods known to those skilled in the art of recombinant DNA technology. The plasmid was first introduced into *E. coli* DH5a to obtain large quantities of the recombinant plasmid. The recombinant *E. coli* strain, which was unable to express the *M. tuberculosis* 30 kDa non-fusion protein, was grown in the presence of 250 μg/ml hygromycin and the plasmid insert's DNA sequence was determined in its entirety. The plasmid was introduced into *M. smegmatis* by electroporation using 6.25 kV/cm, 25 μF, and 1000Ω as the conditions yielding the largest number of positive transformants. The present inventors verified the presence of the recombinant plasmid by growth in the presence of 50 μg/ml hygromycin and the constitutive expression and export of recombinant 30 kDa non-fusion protein by polyacrylamide gel electrophoresis and immunoblotting with polyvalent, highly specific rabbit anti-30 kDa non-fusion protein immunoglobulins using methods known to those skilled in the art of recombinant DNA technology. Additionally, the inventors verified the correct expression and processing of the recombinant *M. tuberculosis* 30 kDa non-fusion protein, which was indistinguishable from its native counterpart by N-terminal amino acid sequencing.

The recombinant pSMT3 plasmid pMTB30 was subsequently introduced into *M. bovis* BCG Tice using 6.25 kV/cm, 25 μF, and 200Ω as the optimal electroporation conditions. Transformants were incubated in 7H9 medium supplemented with 2% glucose for 4 h at 37° C. in an environmental shaker and subsequently plated on 7H11 agar with 20 μg/ml hygromycin. The concentration of hygromycin was gradually increased to 50 μg/ml as the transformants were subcultured to a new growth medium. Recombinant BCG Tice cultures were maintained under the same conditions as the wild-type except that the 7H9 medium contained 50 μg/ml hygromycin.

The expression and export of recombinant *M. tuberculosis* 30 kDa non-fusion protein were verified by polyacrylamide gel electrophoresis and immunoblotting with polyvalent, highly specific rabbit anti-30 kDa non-fusion protein immunoglobulins. Typically, one in ten transformants expressed and exported significantly larger quantities of recombinant non-fusion protein than the other transformants; two such transformants were chosen and a large stock of these transformants was prepared and frozen at −70° C. in 7H9 medium containing 10% glycerol. These transformants were used for immunogenic composition efficacy studies in guinea pigs. FIG. 1*a* shows the expression of the *M. tuberculosis* 30 kDa major extracellular non-fusion protein by recombinant BCG Tice on SDS-PAGE gels and immunoblots. The recombinant strain expressed much more of the *M. tuberculosis* 30 kDa major extracellular non-fusion protein than the wild-type both on Coomassie blue stained gels and immunoblots.

Next a recombinant *M. bovis* BCG Connaught strain (rBCG30 Conn) expressing the *M. tuberculosis* 30 kDa major extracellular non-fusion protein was prepared similarly to that described above for recombinant BCG Tice (rBCG30 Tice) using the aforementioned pMTB30 plasmid. It was maintained in medium containing hygromycin at a concentration of 50 μg/ml under the same conditions as described for the recombinant BCG Tice strain. FIG. 1*b* shows the expression of the *M. tuberculosis* 30 kDa major extracellular non-fusion protein by recombinant BCG Connaught on SDS-PAGE gels and immunoblots. The recombinant strain expressed much more of the *M. tuberculosis* 30 kDa major extracellular non-fusion protein than the wild-type both on Coomassie blue stained gels and immunoblots.

Additionally, the relative expression of major extracellular proteins in rBCG strains utilizing plasmid pNBV1 and a promoter from the upstream region immediately adjacent to the glutamine synthetase gene glnA1 or the gene encoding the extracellular protein was compared to the parental BCG strain. Immunoblots of each of the recombinant protein from each of the recombinant strains were digitized using a CreoScitex EverSmart Jazz scanner and protein bands were densitometrically analyzed by area measurement using the NIH image 1.62 software program. The expression levels of these recombinant proteins are given in Table 1.

TABLE 1

Expression of recombinant proteins by recombinant strains of BCG Tice

| Strain | Expression of 30 kDa Protein (Relative Units) | Expression of 23.5 kDa Protein (mg/L) | Expression of 32A kDa Protein (Relative Units) |
|---|---|---|---|
| BCG Tice | 1.0 | 0 | 1.0 |
| rBCG30 Tice I | 5.4x | | |
| rBCG30 Tice II (pNBV1-PglnA1-MTB30) | 24x | | |
| rBCG23.5 Tice I (pNBV1-PglnA1-MTB23.5) | | Approximately 10-15 mg/L | |
| rBCG30/23.5 Tice II (pNBV1-PglnA1-MTB30/23.5) | 24x | Approximately 10-15 mg/L | |
| rBCG30 Tice III (pNBV1-MTB30) | 14.4x | | |
| rBCG23.5 Tice II (PNBV1-MTB23.5) | | 16.2 mg/L | |
| rBCG30/23.5 Tice IIA (pNBV1-MTB30/23.5↑↑) | 23.3x | 18.7 mg/L | |
| rBCG30/23.5 Tice IIB (PNBV1-MTB30/23.5↑↓) | 25.7x | 16.6 mg/L | |
| rBCG32A Tice I (pNBV1-MTB32A) | | | 10.5x |
| rBCG(MB)30 Tice (pNBV1-MB30) | 9.7x | | |
| rBCG(ML)30 Tice I (pNBV1-ML30) | 9.7x | | |

Plasmid stability of recombinant strains of BCG was assessed biochemically. This biochemical analysis demonstrated that in the presence of hygromycin, broth cultures of the recombinant BCG strains maintain a steady level of recombinant non-fusion protein expression over a three month growth period. In the absence of hygromycin, the same cultures show only a slight decrease of non-fusion protein expression (on a per cell basis), indicating that the recombinant plasmid is stably maintained and only very gradually lost in bacteria growing without selective pressure (FIG. 1*a* and FIG. 1*b*, lane 3).

The stability of the various recombinant BCG strains of the present invention expressing *M. tuberculosis* major extracellular proteins utilizing plasmid pNBV1 and a promoter from the upstream region immediately adjacent to the glutamine synthetase gene glnA1 was examined. Expression of the 30 kDa and/or 23.5 kDa proteins by rBCG30 Tice II, rBCG23.5 Tice I, and rBCG30/23.5 Tice I was stable for at least three months of continuous culture (approximately 30 generations) in medium that contained hygromycin for the positive selection of the plasmids. In addition, culture of the strains for one month (approximately. 10 generations) in medium lacking hygromycin resulted in no decrease in expression levels. However, after 6 months of continuous culture in the absence of hygromycin (approximately. 60 generations), expression of the 30 kDa protein by rBCG30 Tice II was greatly reduced and the expression of the 30 kDa and 23.5 kDa proteins by rBCG30/23.5 Tice I was reduced to undetectable levels. Only expression of the 23.5 kDa protein by rBCG23.5 Tice I remained high. It was confirmed that the drop in expression for the two strains was due to loss of the plasmid from a large percentage of cells in the culture (measured by plating the strains on 7H11 plates with and without hygromycin). rBCG23.5 Tice I exhibited no loss of the plasmid (approx. 100% of cells were hygromycin resistant) consistent with the high expression still maintained after 6 months of culture in the absence of hygromycin.

Additionally, the stability of new recombinant BCG strains expressing *M. tuberculosis, M. bovis*, and *M. leprae* major extracellular proteins utilizing plasmid pNBV1 and a promoter from the upstream region immediately adjacent to the gene encoding the extracellular protein was also examined. Expression of the recombinant proteins, i.e. the 30, 23.5, and 32A kDa major extracellular proteins of *M. tuberculosis* and the 30 kDa major extracellular protein of *M. bovis* and *M. leprae*, was stable for at least 12 months of continuous culture (approximately 120 generations) in medium containing or lacking hygromycin, the positive selection marker for the plasmid pNBV1. No loss of plasmid was detected.

These experiments show that the various recombinant strains exhibited a wide spectrum of stability regarding the levels of expression of recombinant proteins. In general, plasmids containing the coding DNA sequences for the recombinant proteins fused to their endogenous promoter regions quite stably expressed the recombinant proteins for at least 12 months, although the levels typically dropped slightly over time, most likely to balance expression and secretion of recombinant proteins with the metabolic state of the bacterial cell and the expression of the corresponding endogenous proteins. In contrast, strains that contained plasmids where the heterologous glnA1 promoter drove expression of recombinant proteins exhibited great variability in stability of expression over time. It should be noted that the recombinant proteins were identical to those expressed from the above mentioned strains. Variability in expression, therefore, is apparently a function of the promoter sequence.

Additionally, for stable two-plasmid, selective pressure-independent expression of multiple proteins of Mycobacteria the following plasmids were used (in alphabetical order): pGB9, a derivative of the cryptic *M. fortuitum* plasmid pMF1 was obtained from K. G. Papavinasasundaram, National Institute for Medical Research, London, UK (Bachrach G, Colston M J, Bercovier H, Bar-Nir D, Anderson C. & Papavinasasundaram K G. 2000. A new single-copy mycobacterial plasmid, pMF1, from *Mycobacterium fortuitum* which is compatible with the pAL5000 replicon. Microbiol 146:297-303); pLC28 (used to assay transmissibility of pGB9.2), a genetic feature of *E. coli* S17, a conjugative R6K derivative containing the mob region of plasmid RP4 and a mutant on R6K which requires a functional π protein in trans for replication as provided by S17's λpir lysogen, was a gift from Olaf Schneewind, University of Chicago, Chicago, Ill. (Cheng et. Al. 1997); R6K, a naturally occurring, self-transmissible *E. coli* plasmid, was obtained from ATCC; pMTB30 (pSMT3-30), a recombinant version of the *E. coli*/mycobacteria shuttle plasmid pSMT3[(Hyg$^r$; ori pAL5000 plasmid for mycobacteria); (Herrmann et al., 1996)], into which was inserted a 4.75 kb *M. tuberculosis* Erdman genomic DNA fragment containing the 30 kDa protein gene [fbpB; Rv1886c; (Cole S T, Brosch R, Parkhill J, Garnier T, Churcher C, Harris D, Gordon S V, Eiglmeier K, Gas S, Barry III C E, Tekaia F, Badcock K, Basham D, Brown D, Chillingworth T, Connor R, Davies R, Devlin K, Feltwell T, Gentles S, Hamlin N, Holroyd S, Hornsby T, Jagels K, Barrell B G. et al. 1998. Deciphering the biology of *Mycobacterium tuberculosis* from the complete genome sequence. Nature 393:537-44)] plus flanking regions, was generated in this laboratory (Harth et al., 1997); pNBV1, another *E. coli*/mycobacteria shuttle plasmid conferring resistance to hygromycin and carrying the replication origin of plasmid pAL5000 was obtained from William Bishai [Johns Hopkins University, Baltimore, Md. (Howard N, Gomez J E, Ko C and Bishai W R. 1995. Color selection with a hygromycin-resistance-based *Escherichia coli*-mycobacterial shuttle vector. Gene 166:181-2)]; and pVK173T (used to assay transmissibility of pGB9.2), an *E. coli*/mycobacteria shuttle plasmid conferring resistance to ampicillin, apramycin, and hygromycin, was a gift from Julian Davies, University of British Columbia, Vancouver, Canada (Paget E and Davies J. 1996. Apramycin resistance as a selective marker for gene transfer in mycobacteria. J Bacteriol 178:6357-60).

The shuttle plasmid pGB9 was modified in its *E. coli* portion by eliminating non-essential regions; the altered version of pGB9 was designated pGB9.2. The original plasmid was digested with Bsu36I and BstZ17I, the restriction sites were filled in and re-ligated, eliminating the cam$^r$ gene, a partial tet$^r$ gene and part of the intergenic region of pACYC184 between the tet$^r$ gene and the on p15A. This step eliminated approximately 2.8 kb of DNA from pGB9 and left only the Tn5 derived kanamycin resistance gene as a selective marker. Another deletion eliminated the two PlacZ and lacZα carrying Asel-Asel fragments, which were replaced by a multi-cloning site representing the end of the *E. coli* portion and the start (HindIII restriction site) of the mycobacterial portion (pMF1). All modifications and cloning steps were confirmed by restriction enzyme mapping and DNA sequencing across each of the newly joined fragments.

The modified pGB9 plasmid pGB9.2 was assayed for its capacity to express recombinant proteins by inserting the *M. tuberculosis* 30 kDa protein gene (fbpBRv1886c; mycolic acid transferase) into the plasmid's multi-cloning site and driving expression of the protein by its endogenous promoter. The plasmid pMTB30 (Horwitz et al., 2000) served as a template to generate a PCR product which encompassed the 30 kDa protein coding region preceded by approximately 500 by of upstream DNA sequence (promoter region) and was flanked at the 5' end by ClaI, MluI, NdeI, PacI, and HindIII restriction sites and at the 3' end by PacI, NdeI, MluI, and BamHI restriction sites. The 30 kDa protein gene cassette was lifted from the PCR product with PacI and inserted into the PacI site of pGB9.2 (FIG. 12). All constructs were first established in *E. coli* DH5a and then electroporated into *M. bovis* BCG Tice, *M. smegmatis* 1-2c wild-type, and *M. tuberculosis* Erdman wild-type using a gene pulser II unit (Bio-Rad) at settings of 12.5 kV $cm^{-1}$, 25 pF, and 1000 ohms. Coomassie-stained gels of the secretion of pGB9.2-30 expressed *M. tuberculosis* 30 kDa protein in various Mycobacteria are depicted in FIG. 10.

The mycobacterial shuttle vector pNBV1(Hyg$^r$) was modified by inserting a gene coding for apramycin resistance which allowed us to distinguish between strains carrying pNBV1(Apr$^r$Hyg$^r$) and pSMT3(Hyg$^r$). The apramycin resistance gene [aac(3)-IVa], which encodes a type IV aminoglycoside 3-N-acetyl-transferase (261 aa), was inserted into pNBV1 such that it replaced the short segment between the two DraI sites located in the region between the hyg$^r$ gene and the ColE1 on element; apramycin is mainly employed as an antibiotic in animal husbandry (Paget and Davies, 1996). The mycobacterial shuttle vector pVK173T served as a template for the amplification product which encompassed the apramycin coding region preceded by approximately 200 by of upstream (promoter) region and was flanked by DraI sites. Both insert orientations were obtained and verified by DNA sequencing across the insert junctions. Coomassie-stained gels of this two-plasmid system for the expression of *M. tuberculosis* 30 kDa protein in *M. bovis* BCG Tice are depicted in FIG. 11.

It is understood that using the methods described above in conjunction with methods known to those skilled in the art of recombinant DNA technology, recombinant BCG strains (prototrophs, auxotrophs and metabolically impaired strains) expressing the *M. tuberculosis* major extracellular non-fusion proteins can be prepared. Furthermore, similar methodologies can be used to prepare recombinant BCG strains expressing *M. leprae* major extracellular non-fusion proteins including, but not limited to the *M. leprae* 30 kDa major extracellular non-fusion protein homolog of the *M. tuberculosis* 30 kDa major extracellular non-fusion protein (a.k.a. Antigen 85B), the *M. leprae* 32A kDa major extracellular non-fusion protein homolog of the *M. tuberculosis* 32A kDa major extracellular non-fusion protein (a.k.a. Antigen 85A), and other *M. leprae* major extracellular non-fusion proteins. Additionally, similar methodologies also can be used to prepare recombinant *M. bovis* BCG expressing the *M. bovis* 30 kDa major extracellular non-fusion protein homolog of the *M. tuberculosis* 30 kDa major extracellular non-fusion protein (a.k.a. Antigen 85B), the *M. bovis* 32A kDa major extracellular non-fusion protein homolog of the *M. tuberculosis* 32A kDa major extracellular non-fusion protein (a.k.a. Antigen 85A), and other *M. bovis* major extracellular proteins.

The present invention is useful for preparing immunogenic compositions against a variety of intracellular pathogens, such compositions including, but not limited to BCG strains over expressing the major extracellular non-fusion proteins of *M. tuberculosis*, *M. bovis* or *M. leprae*. Immunogenic compositions made in accordance with the teachings of the present invention are useful in eliciting immune responses in hosts. The induced immune responses can be either humoral (antibody-based) or cellular and are useful in diagnostic, protective, or palliative applications.

The present invention provides recombinant attenuated intracellular pathogen immunogenic compositions such as rBCG that express their own endogenous extracellular proteins in addition to recombinant extracellular non-fusion proteins of closely related and/or other intracellular pathogens. However, it has been demonstrated through 80 years of studies that BCG's endogenous extracellular proteins alone do not provide complete protection in all recipients. Furthermore the present inventors have also demonstrated that merely co-injecting *M. tuberculosis* extracellular proteins along with traditional BCG does not result in immunogenic compositions superior to BCG alone.

In one embodiment of the present invention the immunogenic composition includes a recombinant BCG immunogenic composition expressing only one immunogen, for example, but not limited to, the 23.5 kDa, 30 kDa, or 32 kDa major extracellular proteins of *M. tuberculosis*.

In another embodiment of the present invention the recombinant BCG may express two or more immunogens, for example the 23.5 kDa and the 30 kDa major extracellular proteins of *M. tuberculosis*. This latter embodiment may be particularly effective as a immunogenic composition for preventing diseases in mammals. The present inventors have proposed the non-limiting theory that the simultaneous over expression of the 23.5 kDa and the 30 kDa major extracellular proteins of *M. tuberculosis* by a recombinant BCG may act synergistically to heighten the mammalian immune response against the intracellular pathogens of the present invention. This theory is partially based on the observation that wild-type and recombinant BCG are deletion mutants of *M. bovis* that do not naturally express their own 23.5 kDa major extracellular protein. In this embodiment, the recombinant BCG of the present invention is transformed to express one or more recombinant major extracellular proteins simultaneously. However, the polynucleotide sequences encoding the amino acid sequences of the recombinant major extracellular proteins may be on the same or different plasmids and may be expressed in the same or different amounts relative to each other.

However, immunogenic compositions utilizing BCG as the transformant can cause disseminated disease in immunocompromised persons such as those with AIDS. In rare cases the disseminated disease can be fatal. Therefore, in another embodiment of the present invention recombinant BCG strains, using BCG Tice as the wild-type parent, that are anticipated to be safe for use in eliciting an immune response in immunocompromised hosts have been developed. Four of these strains are auxotrophs and hence they multiply only in the presence of excess amounts of the amino acid for which they are auxotrophic. In one embodiment of the present invention, non-limiting exemplary examples include BCG tryptophan or glutamine. For this reason, their growth is regulatable by the host as will be discussed further below. Two additional BCG strains suitable for use in immunosuppressed, or partially immunosupresed mammals are not auxotrophs and hence not growth-regulatable. These prototrophic BCG strains are allelic exchange mutants and are anticipated to be attenuated in immunocompromised hosts.

However, as previously stated, the present invention is not limited to auxotrophic strains of the transformant. The present inventors anticipate that auxotrophs may not be suitable for all applications where the present immunogenic compositions are desirable. For example, while auxotrophs are useful in regulating the transformant's growth in vivo, it requires that a second composition be administered timely and consistently to assure that the host develops the desired immune response. This requires vigilance on the part of the administering personnel, the host and the host's caregiver. Therefore, in order to minimize the requirement for a co-administered second composition, the present inventors have developed metabolically impaired immunogenic compositions that have a limited life span in the vaccine thus minimizing the possibility of disseminated disease. In one embodiment of the present invention the metabolically impaired immunogenic compositions are siderophore mutants that do not require the co-administration of an additional cofactor. For example, and not intended as a limitation, in one embodiment of the present invention a siderophore auxotroph is "pre-loaded" with an essential mineral. Pre-loading as used herein refers to a process whereby the siderophore auxotroph is cultivated in a mineral rich environment in the presence of an exogenously supplied siderophore. Under these growth conditions the siderophore mutant acquires sufficient reserves of the essential mineral to permit several multiplications over several generations. Once the "preloaded" reserves of mineral are depleted, the siderophore auxotroph ceases dividing and is harmlessly cleared from the vaccine recipient. In one embodiment of the present invention the siderophore is a mycobactin or exochelin (or both) and the essential mineral is iron.

In another embodiment of the present invention, a BCG auxotroph was developed that is defective in pantothenate (vitamin B5). The vaccinated host would take pantothenate supplements to allow the BCG to induce an immune response but if the BCG vaccine beings to disseminate and cause disease, the vaccinated host can stop taking the pantothenate supplement to stop the vaccine from multiplying.

IV. Vaccination Strategies

The immunogenic compositions of the present invention can be used as both immunoprophylactic and immunotherapeutic compositions. The composition of the immunoprophylactic embodiment of the present invention and the associated vaccination strategy will vary depending on the immune status of the host and the level of immune response desired. Auxotrophic and metabolically impaired forms of the present invention are generally used when the vaccinee is immunocompromised and prototrophs are generally used in immunocompetent vaccinees.

Traditionally, vaccines, including those made in accordance with the present invention, are administered to the immunologically naïve vaccinee using a route of administration most appropriate for the vaccine type. Routes of administration generally include oral, intradermal, intramuscular, subcutaneous, intranasal, intranodal or aerosolized and inhaled. However, regardless of the route of administration, traditional vaccination protocols call for an initial immunization followed by one or more booster vaccines using the same immunogenic composition as initially administered.

Previous studies of vaccines directed against a variety of pathogens have shown that delivering more than one dose of a vaccine or sequentially administering two different types of vaccines against the same pathogen, sometimes using what is referred to as a "prime-boost" strategy in which the first vaccine primes the immune system such that there is a greater or qualitatively more efficacious immune response to the second vaccine, can sometimes result in enhanced protective immunity. With respect to experimental vaccines directed against tuberculosis, Tanghe et al. (2001) found that immunizing first with a DNA vaccine encoding Antigen 85A and subsequently with purified Antigen 85A protein induced greater protective immunity than immunizing with either the DNA or protein vaccine alone. Feng et al. (2001) showed that immunizing first with a DNA vaccine encoding Antigen 85B and subsequently with BCG vaccine yielded greater protection than immunization with BCG alone. Brooks et al. (Brooks J V, Frank A A, Keen M A, Belisle J T and Orme I A. 2001. Boosting vaccine for tuberculosis. Infect Immun 69:3714-17) reported that immunization first with BCG and subsequently with Antigen 85A plus IL-2 gave better protection than immunization first with BCG and subsequently with saline; whether the enhanced effect was due to the Antigen 85A protein or the IL-2 or both was not reported. Goonetilleke et al. (2003) reported that immunization first with intranasal BCG and subsequently with intranasal BCG or intranasal recombinant modified vaccinia virus Ankara induced greater protective immunity than a single immunization with intranasal BCG.

However, traditional prime-boost or multiple immunization strategies do not necessarily result in enhanced protective immunity against tuberculosis. In previous unpublished studies in our laboratory, the present inventors attempted to improve the protective immunity of the rBCG30 vaccine by immunizing animals with this vaccine twice 10 weeks apart. However, the present inventors found that two vaccinations with this vaccine were not better than one. Similarly, the present inventors found that two vaccinations with BCG wild-type were not better than one. Skinner et al. (Skinner M A, Ramsay A J, Buchan G S, Keen D L, Ranasinghe C, Slobbe L, Collins D M, De Lisle G W, and Buddle B M. 2003. A DNA prime-live vaccine boost strategy in mice can augment IFN-γ responses to mycobacterial antigens but does not increase the protective efficacy of two attenuated strains of *Mycobacterium bovis* against bovine tuberculosis. Immunology 108: 548-55) found that a prime-boost strategy involving a DNA prime followed by a live BCG boost did not increase protection against an *M. bovis* challenge. Mollenkopf (Mollenkopf H-J, Groine-Triebkorn D, Andersen P, Hess J and Kaufmann S. 2001. Protective efficacy against tuberculosis of ESAT-6 secreted by a live *Salmonella typhimurium* vaccine carrier strain and expressed by naked DNA. Vaccine 19: 4028-35) did not find significantly improved protection against challenge with *M. tuberculosis* either by using a prime-boost strategy in which a recombinant *Salmonella typhimurium* vaccine carrier strain was administered first followed by a DNA vaccine or by using a prime-boost strategy in which the DNA vaccine was administered first followed by the *Salmonella typhimurium* vaccine carrier strain. In studies of BCG and DNA vaccines in immunotherapeutic models, others have found that multiple vaccinations were not only ineffective but harmful, leading to an increase rather than a decrease in pulmonary pathology.

Therefore, the present inventors have developed a novel prime-boost strategy for *M. tuberculosis* which includes first immunizing with a recombinant BCG over expressing a *M. tuberculosis* major extracellular protein and subsequently immunizing with the purified protein. The administration of the vaccine in this way induces enhanced protection over that achieved by immunization with BCG alone, by immunization with rBCG30 alone, or even by immunization with BCG first followed later by immunization with the purified *M. tuberculosis* major extracellular protein. In the non-limiting exemplary embodiment that follows, the first immunization was with rBCG30, a recombinant BCG strain over expressing the *M. tuberculosis* 30 kDa major secretory protein, a.k.a. Antigen 85B or r30, and the second immunization was with the purified *M. tuberculosis* 30 kDa major secretory protein. It should be understood that the prime-boost strategy of the present invention can be practiced using any of the immunogenic compositions and or immunogens disclosed herein and should not be limited to exemplary embodiments. The immunogenic compositions useful in practicing the prime-boost strategy of the present invention include prototrophs, auxotrophs and metabolically impaired strains of rBCG.

The vaccination strategy of the present invention includes a vaccination strategy by which a live recombinant BCG vaccine over expressing a *M. tuberculosis* major extracellular protein, such as rBCG30, is administered first, and after a period of time, the purified *M. tuberculosis* major extracellular protein, such as r30, is administered one or more times. The initial vaccination may be with any recombinant strain of BCG over expressing and secreting one or more *M. tuberculosis* major extracellular proteins, including but not limited to the 30 kDa major secretory protein (Antigen 85B), 32A major secretory protein (Antigen 85A), 32B major secretory protein (Antigen 85C), the 23.5 kDa major secretory protein (a.k.a. MPT64), the 16 kDa major secretory protein, the 23 kDa subunit mass superoxide dismutase, the 58 kDa subunit mass glutamine synthetase, the 71 kDa subunit mass heat shock protein, the 12 kDa subunit mass exported fragment of the 16 kDa alpha-crystallin protein, the 14 kDa secreted protein, etc. Such extracellular proteins were previously shown to be immunoprotective against *M. tuberculosis* (Horwitz et al., 1995).

Each vaccine is administered intradermally or by another route, e.g. subcutaneously, percutaneously, intramuscularly, or even orally to a mammalian host. The vaccine induces a cell-mediated immune response to the recombinant major extracellular protein. The vaccine subsequently protects against infection with *M. tuberculosis* or other mycobacterial disease.

In summary, the present invention provides a comprehensive vaccination strategy and related immunogenic compositions suitable for treating, preventing and palliating intracellular pathogen diseases, specifically those associated with the genus *Mycobacterium*. The present invention provides recombinant BCG strains that over express one or more major extracellular proteins of the genus *Mycobacterium*. The rBCG of the present invention are transformed with one or a plurality of extrachromosomal plasmids that express one or more major extracellular proteins. Additionally, the rBCG (immunogenic compositions) of the present invention may be prototrophs, auxotrophs or metabolically impaired mutants. The immunogenic compositions of the present invention may be used in immunocompetent and immunocompromised vaccinees and may be used alone or as part of a novel prime-boost strategy. The following section details experiments that prove the safety and efficacy of the present invention. The animal model selected (the guinea pig) by the present inventors is a well established experimental model that is considered predictive of results seen in other animals, including humans.

V. Representative Methods for Testing Safety and Efficacy of the Immunogenic Compositions of the Present Invention Following the successful immunogenic composition production, the immunogenic compositions of the present invention are tested for safety and efficacy using an animal model. The studies utilize guinea pigs because the guinea pig model is especially relevant to human tuberculosis clinically, immunologically, and pathologically. In contrast to the mouse and rat, but like the human, the guinea pig a) is susceptible to low doses of aerosolized *M. tuberculosis*; b) exhibits strong cutaneous DTH to tuberculin; and c) displays Langhans giant cells and caseation in pulmonary lesions. However, whereas only about 10% of immunocompetent humans who are infected with *M. tuberculosis* develop active disease over their lifetime (half early after exposure and half after a period of latency), infected guinea pigs always develop early active disease. While guinea pigs differ from humans in this respect, the consistency with which they develop active disease after infection with *M. tuberculosis* is an advantage in trials of immunogenic composition efficacy.

The following Examples serve to illustrate the novel aspect of the present invention. Each example illustrates representative methods for testing safety and efficacy of the immunogenic compositions of the present invention and means of delivering the immunogens of the present invention using techniques closely related to, but different from the immunogenic composition of the present invention. Therefore, the following Examples serve to highlight the completely surprising and remarkable advance that the intracellular pathogen immunogenic compositions of the present invention represent to the field of infectious disease immunology. These Examples are for illustrative purposes only and are not to be deemed limiting.

EXAMPLE 1

The immunization inocula made in accordance with the teachings of the present invention were prepared from aliquots removed from logarithmically growing wild-type or recombinant BCG cultures (the "bacteria"). Each aliquot of bacteria was pelleted by centrifugation at 3,500×g for 15 min and then washed with 1× phosphate buffered saline (1×PBS, 50 mM sodium phosphate pH 7, 150 mM sodium chloride). The immunization inoculums were then resuspended to a final concentration of $1 \times 10^4$ colony forming units (CFU) per mL in 1×PBS and contained 1,000 viable bacteria per 100 μL.

Specific-pathogen free 250-300 g outbred male Hartley strain guinea pigs from Charles River Breeding Laboratories, in groups of 9, were immunized intradermally with one of the following: 1) BCG Connaught ($10^3$ CFU) one time only (time 0 weeks); 2) rBCG30 Connaught ($10^3$ CFU) one time only (time 0 weeks); 3) purified recombinant *M. tuberculosis* 30 kDa major extracellular non-fusion protein (r30), 100 μg in 100 μL Syntex adjuvant formulation (SAF), three times three weeks apart (time 0, 3, and 6 weeks); SAF consisted of Pluronic L121, squalane, and Tween-80, and in the first immunization, alanyl muramyl dipeptide; and 4) SAF only (100 μL) (sham-immunized), three times three weeks apart (time 0, 3, and 6 weeks). An additional group of 3 animals was sham-immunized with SAF only (100 μL) and used as a skin test control. These and three to six other sham-immunized animals served as uninfected controls in the challenge experiments.

Nine weeks after the only immunization (BCG and rBCG30 groups) or first immunization (r30 group and sham-immunized skin-test group), guinea pigs were shaved over the back and injected intradermally with 10 μg of purified recombinant *M. tuberculosis* 30 kDa major extracellular non-fusion protein (r30) in 100 μL phosphate buffered saline. After 24 hours, the diameter of erythema and induration was measured. (A separate group of sham-immunized animals from the ones used in the challenge studies was used for skin-testing. Sham-immunized animals used in challenge studies were not skin-tested to eliminate the possibility that the skin-test itself might influence the outcome).

Nine weeks after the first or only immunization and immediately after skin-testing, animals were challenged with an aerosol generated from a 10 mL single-cell suspension containing $1 \times 10^5$ CFU of *M. tuberculosis*. *Mycobacterium tuberculosis* Erdman strain (ATCC 35801) was passaged through outbred guinea pigs to maintain virulence, cultured on 7H11 agar, subjected to gentle sonication to obtain a single cell suspension, and frozen at −70° C. for use in animal challenge experiments. The challenge aerosol dose delivered approximately 40 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal were removed and cultured for CFU of *M. tuberculosis*.

Figure 2A:
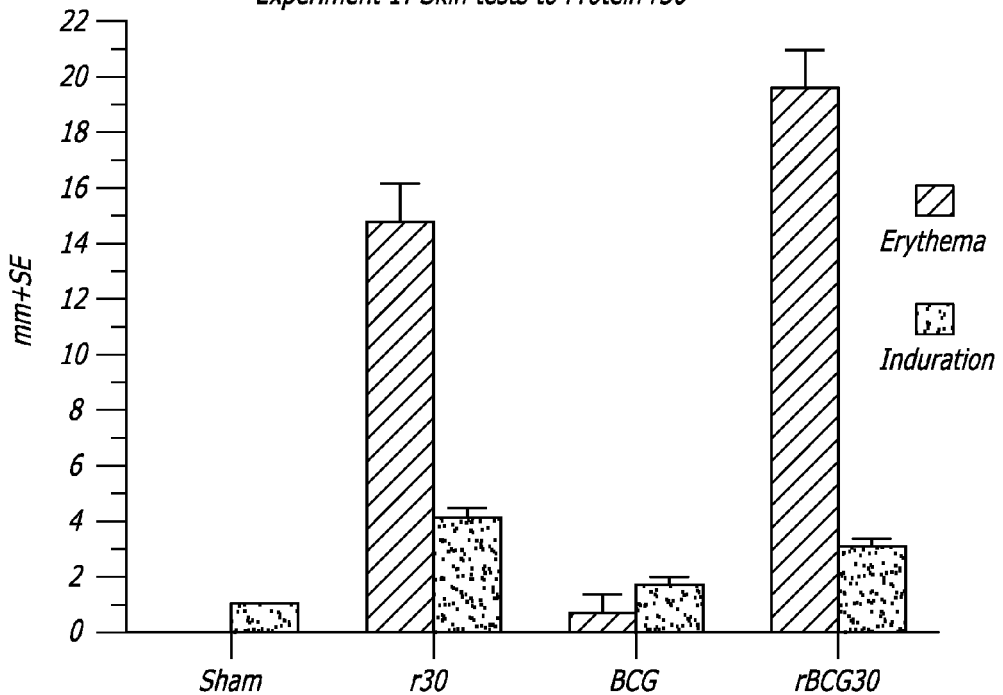
FIG. 2 graphically depicts the results from two experiments labeled 2*a* and 2*b* designed to compare skin test results of guinea pigs inoculated with the recombinant BCG immunogenic composition expressing the 30 kDa major extracellular protein of *M. tuberculosis*, with BCG alone, with the recombinant 30 kDa protein alone, or with a sham immunogenic composition.
Figure 2B:
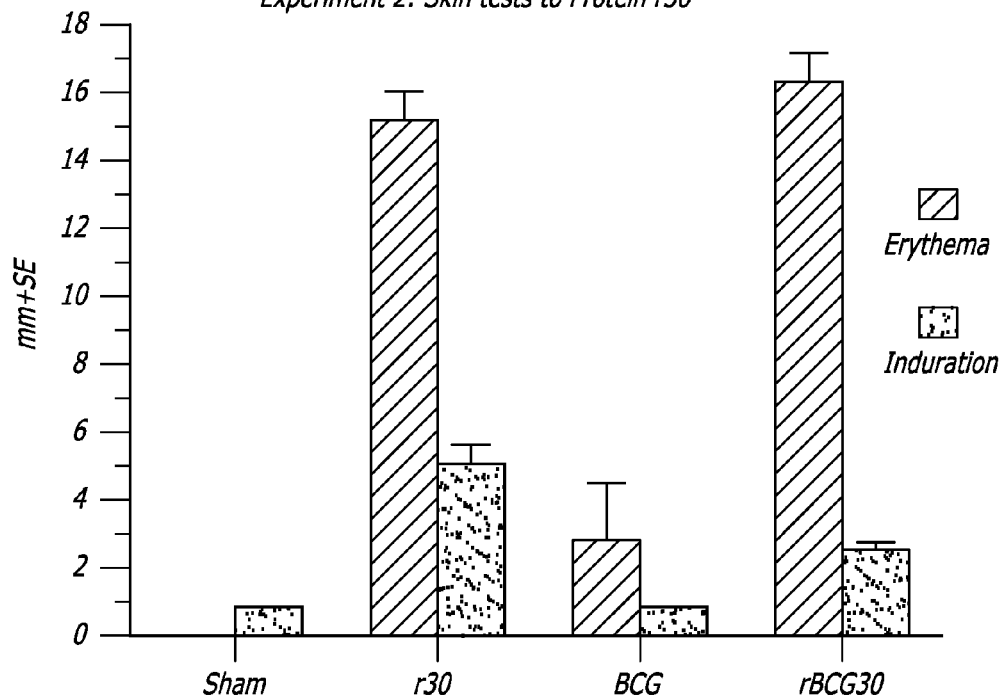

In each of the two experiments, the sham-immunized animals and animals immunized with wild-type BCG exhibited little or no erythema and induration upon testing with recombinant 30 kDa *M. tuberculosis* major extracellular non-fusion protein (r30). In contrast, animals immunized with r30 or rBCG30 exhibited marked erythema and induration that was significantly higher than in the sham-immunized or wild-type BCG immunized animals (Table 2 and FIG. 2).

TABLE 2

Cutaneous Delayed Type Hypersensitivity to the
*M. tuberculosis* 30 kDa Major Extracellular Protein

| | Erythema (Mean Diameter ± SE) (mm) | Induration (Mean Diameter ± SE) (mm) |
|---|---|---|
| Experiment 1 | | |
| Sham-immunized | 0.0 ± 0.0 | 1.0 ± 0.0 |
| r30 | 15.0 ± 1.2 | 4.2 ± 0.3 |
| BCG | 0.8 ± 0.8 | 1.7 ± 0.2 |
| rBCG30 | 19.8 ± 2.2 | 3.1 ± 0.2 |
| Experiment 2 | | |
| Sham-immunized | 0.0 ± 0.0 | 1.0 ± 0.0 |
| r30 | 15.3 ± 0.9 | 5.2 ± 0.7 |
| BCG | 3.0 ± 1.5 | 1.0 ± 0.0 |
| rBCG30 | 16.5 ± 0.9 | 2.7 ± 0.4 |

Figure 3B:
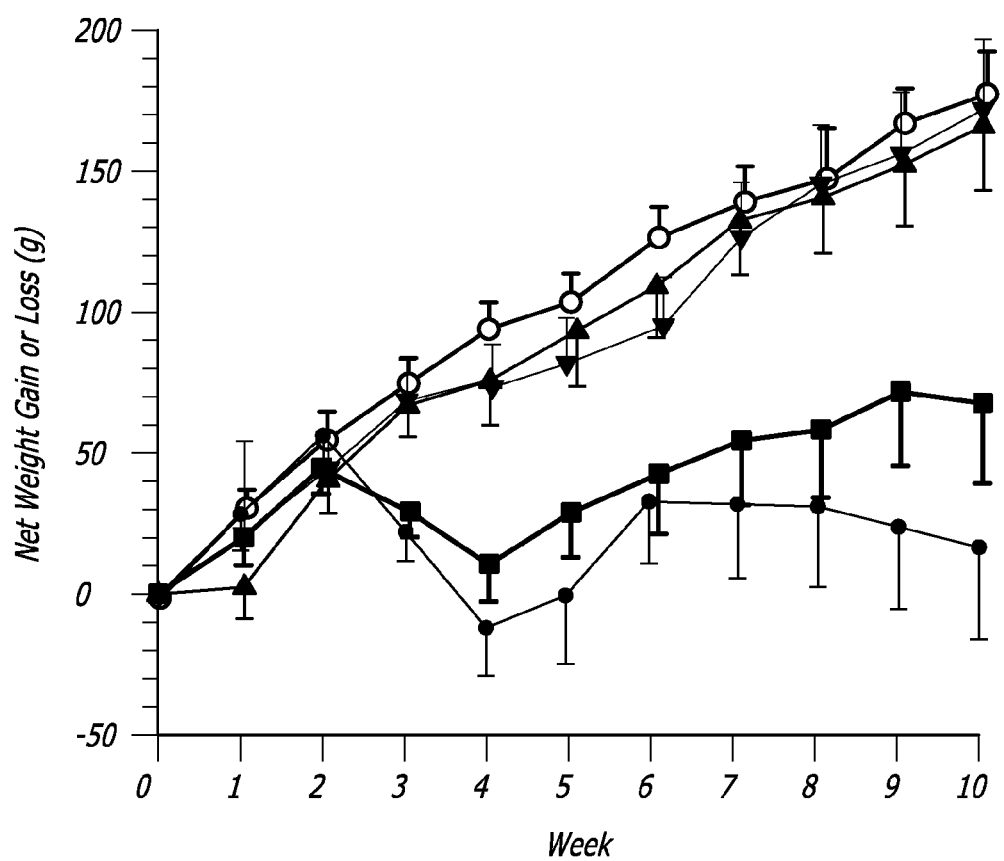
FIG. 3 graphically depicts the weight change in guinea pigs labeled 3*a* and 3*b* following post immunization challenge with *M. tuberculosis*.

In each of the two experiments, uninfected controls gained weight normally after challenge as did animals immunized with either rBCG30 or wild-type BCG (FIG. 3). Indeed there were no significant differences in weight gain among these three groups. In contrast, sham-immunized animals and to a lesser extent r30 immunized animals, exhibited diminished weight gain over the course of the experiment (Table 3 and FIG. 3). Hence, after challenge with *M. tuberculosis*, both BCG and rBCG30 protected animals completely from weight loss, a major physical sign of tuberculosis in humans, and a hallmark of tuberculosis in the guinea pig model of this chronic infectious disease.

TABLE 3

Net Weight Gain After Aerosol Challenge with
Virulent *M. tuberculosis* Erdman Strain

| | Week 0 (Mean Weight ± SE) (g) | Week 10 (Mean Weight ± SE) (g) | Net Weight Gain (g) Week 0-10 (Mean ± SE) |
|---|---|---|---|
| Experiment 1 | | | |
| Sham-immunized | 763.1 ± 17.1 | 805.4 ± 27.8 | 42.3 ± 28.2 |
| r30 | 793.8 ± 21.6 | 906.3 ± 44.6 | 112.6 ± 32.0 |
| BCG | 763.8 ± 28.7 | 956.3 ± 45.4 | 192.5 ± 23.7 |
| rBCG30 | 767.8 ± 17.6 | 947.7 ± 31.3 | 179.9 ± 25.1 |
| Experiment 2 | | | |
| Sham-immunized | 839.1 ± 21.7 | 857.6 ± 32.4 | 18.5 ± 30.9 |
| r30 | 801.9 ± 36.3 | 888.6 ± 39.7 | 86.7 ± 28.3 |
| BCG | 796.6 ± 29.8 | 963.6 ± 19.8 | 167.0 ± 23.3 |
| rBCG30 | 785.7 ± 17.7 | 958.7 ± 27.7 | 173.0 ± 24.9 |

Figure 4A:
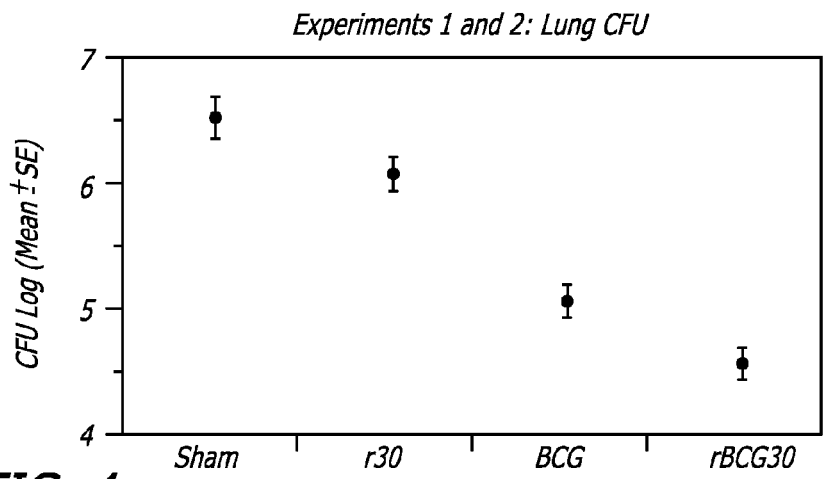
FIG. 4 graphically depicts Colony Forming Units (CFU) of infectious *M. tuberculosis* recovered from guinea pigs' lungs (FIG. 4*a*) and spleens (FIG. 4*b*) following post immunization challenge with *M. tuberculosis*.
Figure 4B:
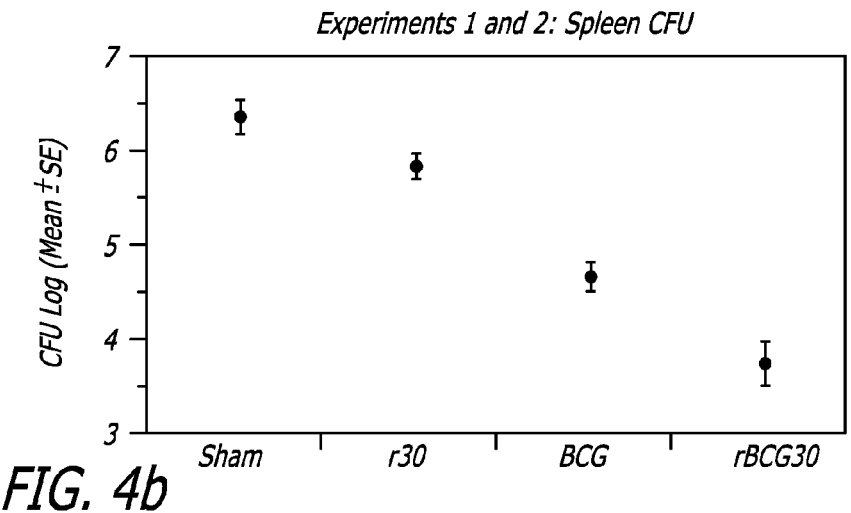

In each of the two experiments, at the end of the 10 week observation period, guinea pigs were euthanized and the right lung and spleen of each animal was removed aseptically and assayed for CFU of *M. tuberculosis*. Sham-immunized animals had the highest bacterial load in the lungs and spleen (Table 4 and FIG. 4a and FIG. 4b). Animals immunized with r30 had fewer organisms in the lungs and spleen than the sham-immunized animals; BCG-immunized animals had fewer organisms than r30-immunized animals; and remarkably, rBCG30-immunized animals had fewer organisms than BCG-immunized animals. Statistical tests employing two way factorial analysis of variance methods to compare means demonstrated that the means of the four "treatment" groups (Sham, r30, BCG, and rBCG30) in Experiment 1 were not significantly different from the means of the four treatment groups in Experiment 2 and that it was therefore appropriate to combine the data in the two experiments. The combined data is shown in Table 4 and FIG. 4. Of greatest interest and importance, the rBCG30-immunized animals had 0.5 log fewer organisms in the lungs and nearly 1 log fewer organisms in the spleen than BCG-immunized animals. On statistical analysis, employing analysis of variance methods to compare means and the Tukey-Fisher least significant difference (LSD) criterion to assess statistical significance, the mean of each of the four groups in both the lungs and spleens was significantly different from the mean of each of the others (Table 5). Differences between the rBCG30 and BCG immunized animals in the lungs were significant at $p=0.02$ and in the spleens at $p=0.001$. Paralleling the differences in CFU in the lungs, on gross inspection, lungs of rBCG30-immunized animals had less lung destruction than BCG-immunized animals (20±4% versus 35±5%, mean±SE).

TABLE 4

Colony Forming Units (CFU) of *M. tuberculosis* in Lungs and Spleens
of Animals Challenged by Aerosol with *M. tuberculosis* Erdman Strain
Combined Experiments 1 and 2

| | n | Lung CFU $Log_{10}$ (Mean ± SE) | Spleen CFU $Log_{10}$ (Mean ± SE) |
|---|---|---|---|
| Sham-immunized | 18 | 6.47 ± 0.17 | 6.27 ± 0.19 |
| r30 | 18 | 6.02 ± 0.14 | 5.73 ± 0.14 |
| BCG | 17 | 5.00 ± 0.13 | 4.57 ± 0.17 |
| rBCG30 | 18 | 4.53 ± 0.14 | 3.65 ± 0.25 |

TABLE 5

Summary of Statistical Analysis (ANOVA) of CFU in Lungs and Spleen
Combined Experiments 1 and 2

| Lung | Sham vs. r30 | $p = 0.03$ |
|---|---|---|
| | r30 vs. BCG | $p = 0.0001$ |
| | BCG vs. rBCG30 | $p = 0.02$ |
| Spleen | Sham vs. r30 | $p = 0.05$ |
| | r30 vs. BCG | $p = 0.0001$ |
| | BCG vs. rBCG30 | $p = 0.001$ |

Thus, administration of recombinant BCG expressing the *M. tuberculosis* 30 kDa major extracellular non-fusion protein induced high level protection against aerosol challenge with *M. tuberculosis* in the highly susceptible guinea pig model of pulmonary tuberculosis. In contrast, as described in the examples below, administration of the same mycobacterial extracellular non-fusion protein (the *M. tuberculosis* recombinant 30 kDa major extracellular non-fusion protein) in adjuvant in combination with BCG does not induce high level protection against aerosol challenge with *M. tuberculosis*; nor does administration of recombinant *M. smegmatis* expressing the *M. tuberculosis* 30 kDa major extracellular non-fusion protein; nor does administration of the *M. tuberculosis* 30 kDa major extracellular non-fusion protein in microspheres that are of the same approximate size as BCG and like BCG slowly release the proteins over 60-90 days; nor does administration of the *M. tuberculosis* 30 kDa major extracellular non-fusion protein encapsulated in liposomes.

A very surprising aspect of this invention is that the rBCG30 strain induced protection superior to wild-type BCG even though the wild-type expresses and secretes an endogenous highly homologous 30 kDa major extracellular protein that differs from the *M. tuberculosis* protein by only two amino acids (see FIG. 1). Hence, the improved protection of the recombinant strain is unlikely to be due to the small amino acid difference between the recombinant and endogenous proteins. More likely, it is due to the enhanced expression of the recombinant non-fusion protein compared with the endogenous protein. If so, then the abundant expression obtained by using a high copy number plasmid was likely an important factor in the success of the recombinant immunogenic composition.

EXAMPLE 2

In this experiment, specific-pathogen free 250-300 g outbred male Hartley strain guinea pigs from Charles River Breeding Laboratories, in groups of 9, were immunized intradermally with $10^3$ CFU of one of the following strains:

Group A: BCG Tice Parental Control
Group B: rBCG30 Tice I (pMTB30)
Group C: rBCG30 Tice II (pNBV1-PglnA1-MTB30)
Group D: rBCG23.5 Tice I (pNBV1-PglnA1-MTB23.5)
Group E: rBCG30/23.5 Tice I (pNBV1-PglnA1-MTB30/23.5)
Group F: rBCG30 Tice II (pNBV1-PglnA1-MTB30) and rBCG23.5 Tice I (pNBV1-PglnA1-MTB23.5) ($5\times10^2$ of each strain).

In addition, 18 animals were sham immunized with buffer only as follows: Group G: 12 sham animals (for subsequent challenge only) and Group H: 6 sham animals (for skin testing only).

Nine weeks after immunization, 9 guinea pigs in each Group A-F above and the 6 animals in the sham Group H were shaved over the back and injected intradermally with 10 μg of purified recombinant *M. tuberculosis* 30 kDa major extracellular protein (r30) in 100 μL phosphate buffered saline. Animals immunized with a strain expressing r23.5 (Groups A, D, E, F) and the 6 sham animals in Group H were additionally skin-tested with 10 μg of purified recombinant *M. tuberculosis* 23.5 kDa major extracellular protein in 100 μL phosphate buffered saline. After 24 h, the diameter of erythema and induration was measured. (A separate group of sham-immunized animals from the one used in the challenge studies was used for skin-testing. Sham-immunized animals used in challenge studies were not skin-tested to eliminate the possibility that the skin-test itself might influence the outcome).

The results, as summarized in Table 6, show that the animals immunized with the parental BCG Tice strain (Group A) and the sham-immunized animals (Group H) had little or no erythema and induration upon testing with r30 or r23.5. In contrast, animals immunized with a recombinant BCG strain expressing r30 had marked erythema and induration in response to r30 that was significantly higher than in the BCG Tice or sham immunized animals. Similarly, animals immunized with the recombinant BCG strain expressing r23.5 had marked erythema and induration in response to r23.5 that was significantly higher than in the BCG Tice or sham immunized animals. Moreover, animals immunized with the recombinant BCG strain expressing both r30 and r23.5 had marked erythema and induration in response to both of these proteins that was significantly higher than in the BCG Tice or sham immunized animals. Finally, animals immunized with two different strains of recombinant BCG at the same time, one expressing r30 and the other expressing r23.5, had marked erythema and induration in response to both of these proteins that was significantly higher than in the BCG Tice or sham immunized animals.

TABLE 6

Cutaneous Delayed-type Hypersensitivity (DTH) to Purified Recombinant *M. tuberculosis* 30 kDa Major Extracellular Protein (r30) and 23.5 kDa Major Extracellular Protein (r23.5).

| Group | Strain | Test Antigen | Erythema (mm ± SE) | Induration (mm ± SE) |
|---|---|---|---|---|
| A | BCG Tice | r30 | 0 ± 0 | 0 ± 0 |
|   |   | r23.5 | 0 ± 0 | 0 ± 0 |
| B | rBCG30 Tice I | r30 | 16.0 ± 2.3 | 9.0 ± 1.9 |
| C | rBCG30 Tice II | r30 | 15.2 ± 1.2 | 11.2 ± 1.0 |
| D | rBCG23.5 Tice I | r23.5 | 11.3 ± 2.3 | 8.7 ± 1.7 |
| E | rBCG30/23.5 Tice I | r30 | 13.6 ± 2.1 | 12.4 ± 1.8 |
|   |   | r23.5 | 10.3 ± 2.9 | 7.3 ± 2.8 |
| F | rBCG30 Tice II + rBCG23.5 Tice I | r30 | 9.9 ± 2.6 | 8.5 ± 2.6 |
|   |   | r23.5 | 7.6 ± 2.2 | 5.6 ± 2.2 |
| H | Sham | r30 | 0 ± 0 | 0 ± 0 |
|   |   | r23.5 | 0 ± 0 | 0 ± 0 |

Interestingly, animals immunized with the new recombinant BCG strains (Groups C, D, E, and F), all of which express the recombinant proteins utilizing a promoter derived from the upstream region of the *M. tuberculosis* glnA1 gene, did not have greater erythema and induration to r30 than animals immunized with the rBCG30 Tice I strain, that expresses r30 utilizing a promoter derived from the upstream region of the *M. tuberculosis* gene encoding the kDa major extracellular protein.

Nine weeks after immunization and immediately after skin-testing, all animals in Groups A-G were challenged with an aerosol generated from a 10 mL single-cell suspension containing $5\times10^4$ CFU of *M. tuberculosis*. (Prior to challenge, the challenge strain, *M. tuberculosis* Erdman strain [ATCC 35801], had been passaged through outbred guinea pigs to maintain virulence, cultured on 7H11 agar, subjected to gentle sonication to obtain a single cell suspension, and frozen at −70° C.). This aerosol dose delivered approximately 20 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 wk and then euthanized. The right lung and spleen of each animal was removed and cultured for CFU of *M. tuberculosis* on Middlebrook 7H11 agar for two weeks at 37° C., 5% $CO_2$-95% air atmosphere.

The results of the assay for CFU in the lungs and spleens are shown in Table 7. These results showed that animals immunized with BCG or any recombinant BCG strain had much lower CFU in the lungs and spleens than the sham immunized animals. Of importance, animals immunized with any of the recombinant BCG strains had lower CFU in the lungs and spleens than animals immunized with the parental BCG Tice strain. However, none of the recombinant strains tested in this experiment were superior to rBCG30 Tice I.

TABLE 7

Protective Immunity to Aerosol Challenge: CFU in Lungs and Spleens

| Group | Strain | Lung (Mean Log CFU ± SE) | Spleen (Mean Log CFU ± SE) |
|---|---|---|---|
| A | BCG Tice | 4.89 ± 0.14 | 3.92 ± 0.24 |
| B | rBCG30 Tice I | 4.33 ± 0.18 | 2.99 ± 0.25 |
| C | rBCG30 Tice II | 4.61 ± 0.12 | 3.14 ± 0.19 |
| D | rBCG23.5 Tice I | 4.70 ± 0.15 | 3.40 ± 0.20 |
| E | rBCG30/23.5 Tice I | 4.86 ± 0.17 | 3.60 ± 0.26 |
| F | rBCG30 Tice II + rBCG23.5 Tice I | 4.65 ± 0.20 | 3.80 ± 0.25 |
| G | Sham | 6.20 ± 0.33 | 6.10 ± 0.33 |

EXAMPLE 3

In this experiment, specific-pathogen free 250-300 g outbred male Hartley strain guinea pigs from Charles River Breeding Laboratories, in groups of 6, were immunized intradermally with $10^3$ CFU of one of the following strains:

Group I: BCG Tice Parental Control
Group J: rBCG30 Tice I (pMTB30)
Group K: rBCG30 Tice III (pNBV1-MTB30)
Group L: rBCG23.5 Tice II (pNBV1-pMTB23.5)
Group M: rBCG30/23.5 Tice IIA (pNBV1-MTB30/23.5↑↑)
Group N: rBCG30/23.5 Tice IIB (pNBV1-MTB30/23.5↑↓)
Group O: rBCG32A Tice I (pNBV1-MTB32A).
Group P: Sham immunized with buffer only (six animals).

Nine weeks after immunization, guinea pigs in Groups I-P above were shaved over the back. Animals immunized with a strain expressing r30 (Groups I, J, K, M, and N) and the 6 sham immunized animals in Group P were injected intradermally with 10 μg of purified recombinant *M. tuberculosis* 30 kDa major extracellular protein (r30) in 100 μL phosphate buffered saline. Animals immunized with a strain expressing r23.5 (Groups L, M, N) and the 6 sham animals in Group P were skin-tested with 10 μg of purified recombinant *M. tuberculosis* 23.5 kDa major extracellular protein in 100 μL phosphate buffered saline. Animals injected with a strain expressing r32A (Group O) and the 6 sham animals in Group P were skin-tested with 10 μg of purified recombinant *M. tuberculosis* 32A kDa major extracellular protein in 100 μL phosphate buffered saline. After 24 h, the diameter of erythema and induration was measured.

The results, as summarized in Table 8, show that the animals immunized with the parental BCG Tice strain (Group A) had no erythema and induration upon testing with r30, whereas animals (Groups J, K, M, N) immunized with strains expressing the recombinant 30 kDa protein had marked erythema and induration. Moreover, animals (Groups K, M, and N) immunized with strains expressing r30 in greater abundance than rBCG30 Tice I and utilizing a promoter derived from the upstream region of the 30 kDa protein gene had greater induration, a more reliable indicator of cutaneous delayed-type hypersensitivity than erythema, than animals immunized with rBCG30 Tice I. Animals (Groups L, M, and N) immunized with a recombinant BCG strain expressing r23.5, a protein absent in the parental BCG strain, had marked erythema and induration in response to r23.5, whereas sham immunized animals had little erythema and no induration in response to r23.5. The animals (Group O) immunized with a recombinant BCG strain over expressing r32A had much greater erythema and induration in response to the 32A kDa protein than sham-immunized animals.

TABLE 8

Cutaneous Delayed-type Hypersensitivity (DTH) to Purified Recombinant *M. tuberculosis* 30 kDa Major Extracellular Protein (r30) and 23.5 kDa Major Extracellular Protein (r23.5)

| Group | Strain | Test Antigen | Erythema (mm ± SE) | Induration (mm ± SE) |
|---|---|---|---|---|
| I | BCG Tice | r30 | 0 ± 0 | 0 ± 0 |
| J | rBCG30 Tice I | r30 | 25.1 ± 2.8 | 10.7 ± 3.0 |
| K | rBCG30 Tice III | r30 | 24.6 ± 2.5 | 22.3 ± 2.3 |
| L | rBCG23.5 Tice II | r23.5 | 10.9 ± 3.5 | 10.8 ± 3.4 |
| M | rBCG30/23.5 Tice IIA | r30 | 18.0 ± 3.9 | 16.4 ± 3.8 |
|   |   | r23.5 | 9.3 ± 1.9 | 8.6 ± 1.9 |
| N | rBCG30/23.5 Tice IIB | r30 | 16.5 ± 3.7 | 14.4 ± 3.3 |
|   |   | r23.5 | 9.0 ± 2.3 | 9.0 ± 2.3 |
| O | rBCG32A I | r32A | 7.8 ± 1.1 | 5.3 ± 1.8 |
| P | Sham | r30 | 5.6 ± 3.7 | 4.4 ± 3.4 |
|   |   | r23.5 | 2.8 ± 1.3 | 0 ± 0 |
|   |   | 32A | 0.8 ± 0.5 | 0 ± 0 |

Figure 6:
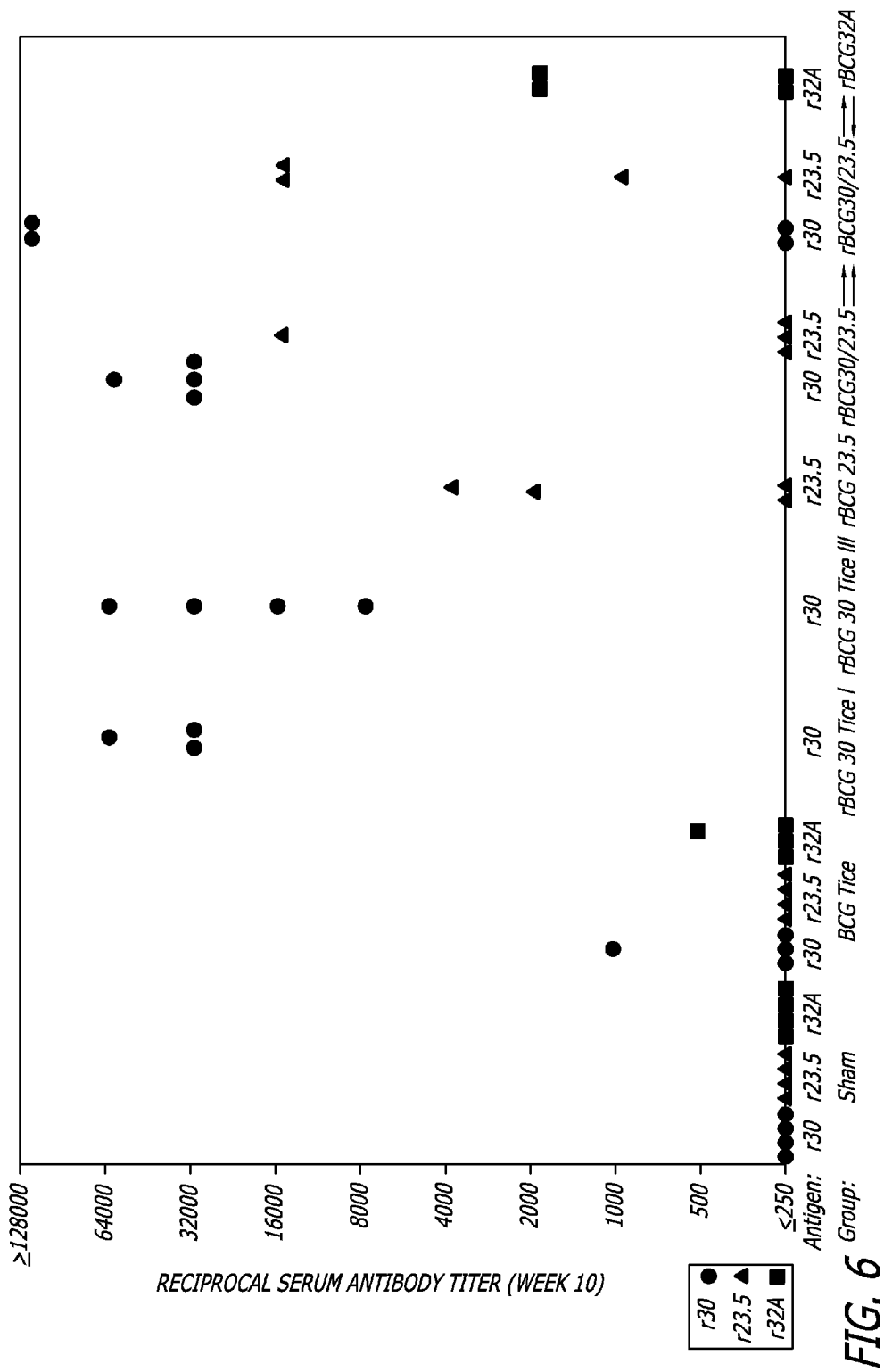
FIG. 6 graphically depicts antibody titers to purified recombinant *M. tuberculosis* 30 kDa major extracellular protein (r30), 32A kDa major extracellular protein (r32A) and 23.5 kDa major extracellular protein (r23.5) in animals sham-immunized or immunized with BCG Tice, rBCG30 Tice I, rBCG30 Tice III, rBCG23.5, rBCG30 +23.5 with the genes oriented in the same direction, rBCG30 +23.5 with the genes oriented in the opposite direction, or rBCG32A.

Additionally, ten weeks after immunization, blood was obtained from several guinea pigs in Groups I-P and serum antibody titers were determined to purified recombinant *M. tuberculosis* 30 kDa major extracellular protein (r30), 32A kDa major extracellular protein (r32A) and 23.5 kDa major extracellular protein (r23.5). Antibody titers were assayed by ELISA and the reciprocal antibody titers for each animal determined. FIG. 6 graphically depicts these results.

EXAMPLE 4

In this experiment designed to demonstrate protection from infection in immunized mammals specific-pathogen free 250-300 g outbred male Hartley strain guinea pigs from Charles River Breeding Laboratories, in groups of 18, were immunized intradermally with $10^3$ CFU of one of the following strains:

Group A: BCG Tice Parental Control
Group B: rBCG30 Tice I (pMTB30)
Group C: rBCG30 Tice III (pNBV1-MTB30)
Group D: rBCG23.5 Tice II (pNBV1-pMTB23.5)
Group E: rBCG30/23.5 Tice IIA (pNBV1-MTB30/23.5↑↑)
Group F: rBCG30/23.5 Tice IIB (pNBV1-MTB30/23.5↑↓)
Group G: rBCG32A Tice I (pNBV1-MTB32A)

In addition, 12 animals were sham-immunized with antigen-free buffer as follows:

Group H: sham animals

Nine weeks after immunization and immediately after skin-testing, all animals in Groups A-H were challenged with an aerosol generated from a 10 mL single-cell suspension containing $5 \times 10^4$ CFU of *M. tuberculosis*. (Prior to challenge, the challenge strain, *M. tuberculosis* Erdman strain (ATCC 35801), had been passaged through outbred guinea pigs to maintain virulence, cultured on 7H11 agar, subjected to gentle sonication to obtain a single cell suspension, and frozen at −70° C.). This aerosol dose delivered approximately 20 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 wk and then euthanized. The right lung and spleen of each animal was removed and cultured for CFU of *M. tuberculosis*. The results are shown in Table 9 below.

TABLE 9

Protective Immunity to Aerosol Challenge: CFU in Lungs and Spleens

| Group | Strain | Lung (Mean Log CFU ± SE) | Spleen (Mean Log CFU ± SE) |
|---|---|---|---|
| A | BCG Tice | 4.80 ± 0.12 | 3.60 ± 0.18 |
| B | rBCG30 Tice I | 4.15 ± 0.13 | 2.36 ± 0.22 |
| C | rBCG30 Tice III | 3.80 ± 0.35 | 2.74 ± 0.31 |
| D | rBCG23.5 Tice II | 4.49 ± 0.23 | 3.08 ± 0.24 |
| E | rBCG30/23.5 Tice IIA | 4.88 ± 0.12 | 3.12 ± 0.27 |
| F | rBCG30/23.5 Tice IIB | 5.01 ± 0.10 | 3.25 ± 0.29 |
| G | rBCG32A Tice I | 4.93 ± 0.09 | 3.28 ± 0.10 |
| H | Sham | 6.09 ± 0.12 | 5.91 ± 0.11 |

EXAMPLE 5

Figure 7:
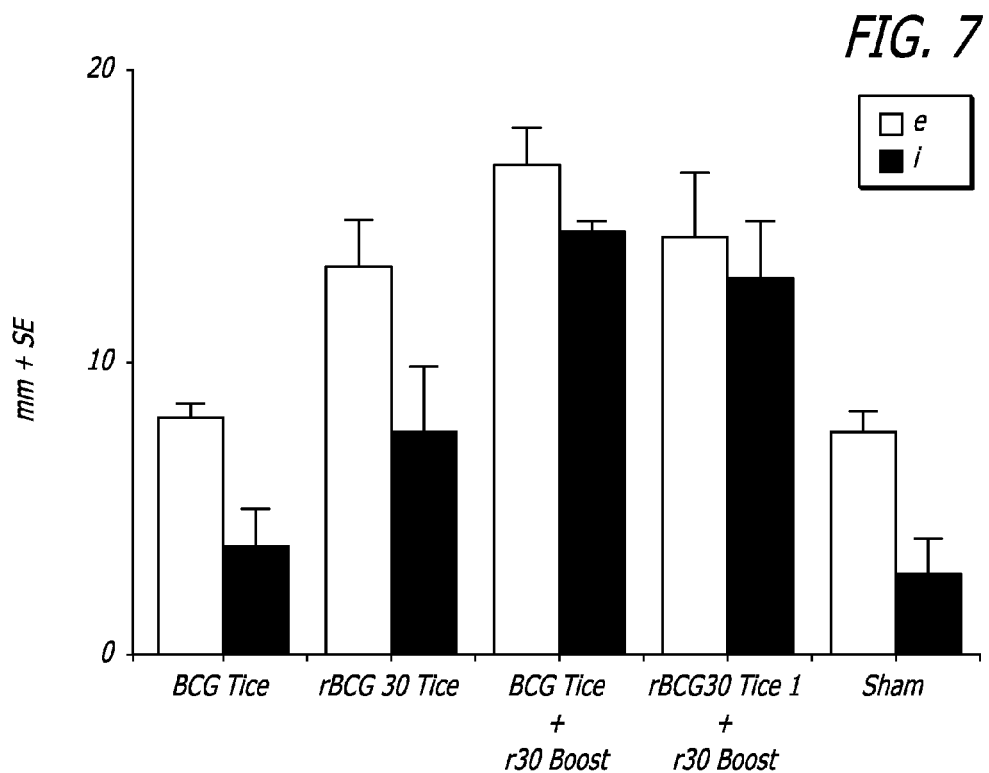
FIG. 7 graphically depicts cutaneous delayed-type hypersensitivity (DTH) of guinea pigs sham-immunized, immunized with BCG or rBCG30 Tice I alone, or immunized with BCG or rBCG30 Tice I as the prime and immunized with purified recombinant *M. tuberculosis* 30 kDa major extracellular protein (r30) as the boost (prime-boost).

In this experiment designed to demonstrate the efficacy of the prime-boost strategy of the present invention, specific-pathogen free 250-300 g outbred male Hartley strain guinea pigs from Charles River Breeding Laboratories, in groups of 15, were immunized intradermally as follows:
Group A: BCG Tice Parental Control ($10^3$ CFU) at Week 0
Group B: rBCG30 Tice I (pMTB30) ($10^3$ CFU) at Week 0
Group C: BCG Tice Parental Control ($10^3$ CFU) at Week 0 and 100 µg of r30 at Week 7
Group D: rBCG30 Tice I (pMTB30) ($10^3$ CFU) at Week 0 and 100 mg of r30 at Week 7
In addition, 11 animals were sham-immunized with buffer only as follows:
Group E: Buffer only
For tests of cutaneous delayed-type hypersensitivity (c-DTH) only, animals in groups of 6 were immunized as follows:
Group F: BCG Tice Parental Control ($10^3$ CFU) at Week 0
Group G: rBCG30 Tice I (pMTB30) ($10^3$ CFU) at Week 0
Group H: BCG Tice Parental Control ($10^3$ CFU) at Week 0 and 100 µg of r30 at Week 7
Group I: rBCG30 Tice I (pMTB30) ($10^3$ CFU) at Week 0 and 100 µg of r30 at Week 7
In addition, 5 of the 11 animals in Group E were skin-tested that were sham-immunized as follows:
Group J: Buffer only
Nine weeks after immunization, guinea pigs in each Group F-J above were shaved over the back and injected intradermally with 10 µg of purified recombinant *M. tuberculosis* 30 kDa major extracellular protein (r30) in 100 µL phosphate buffered saline. After 24 h, the diameter of erythema and induration was measured. The results are summarized in Table 10 and FIG. 7. These results showed that the animals immunized with the parental BCG Tice strain (Group F) and the sham-immunized animals (Group J) had relatively little erythema and induration upon testing with r30. In contrast, animals immunized with a recombinant BCG strain expressing r30 (Group G) had marked erythema and induration in response to r30 that was significantly higher than in the BCG or sham-immunized animals. Most importantly, animals immunized first with BCG or rBCG30, and then 7 weeks later with r30 had even greater erythema and induration. The animals immunized with BCG plus r30 (Group H) had twice as much erythema and four times as much induration as animals immunized with only BCG. The animals immunized with rBCG30 plus r30 (Group I) had only slightly greater erythema than animals immunized with only rBCG30 but nearly twice the amount of induration.

TABLE 10

Cutaneous DTH (Combined Results of Experiment 6)

| Group | Vaccination | Test Antigen | Erythema (mm ± SE) | Induration (mm ± SE) |
|---|---|---|---|---|
| F | BCG | r30 | 8.2 ± 0.5 | 3.7 ± 1.3 |
| G | rBCG30 | r30 | 13.3 ± 1.7 | 7.7 ± 2.2 |
| H | BCG + r30 | r30 | 16.8 ± 1.2 | 14.5 ± 0.3 |
| I | rBCG30 + r30 | r30 | 14.2 ± 2.2 | 12.8 ± 1.9 |
| J | Sham | r30 | 7.6 ± 0.7 | 2.8 ± 1.2 |

Figure 8:
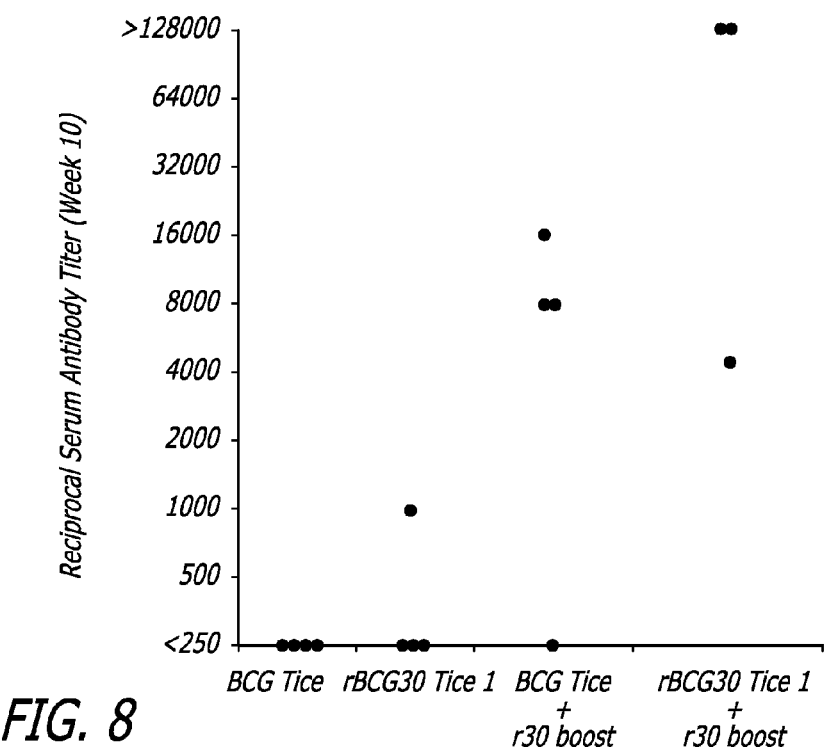
FIG. 8 graphically depicts serum antibody titers to r30 in guinea pigs sham-immunized, immunized with BCG or rBCG30 Tice I alone, or immunized with BCG or rBCG30 Tice I as the prime and immunized with purified recombinant *M. tuberculosis* 30 kDa major extracellular protein (r30) as the boost (prime-boost).

Immediately after skin-testing, 3 or 4 animals in each of Groups F-I were euthanized and their serum obtained. The serum was tested for antibody to r30 using an ELISA assay. The results are shown in Table 11 and FIG. 8. The results showed that animals immunized only with BCG or rBCG30 had relatively low antibody titers. In contrast, animals immunized first with BCG or rBCG30 and later with r30 had on average higher antibody titers. The highest titers were in animals immunized first with rBCG30 and then r30.

TABLE 11 r30 Antibody Titers using an ELISA assay.

| Group | | Guinea Pig | Reciprocal Antibody Titer |
|---|---|---|---|
| F | BCG | 1 | 250 |
| | | 2 | 250 |
| | | 3 | 250 |
| | | 4 | 250 |
| G | rBCG30 | 1 | 1,000 |
| | | 2 | 250 |
| | | 3 | 250 |
| | | 4 | 250 |
| H | BCG + r30 | 1 | 16,000 |
| | | 2 | 8,000 |
| | | 3 | 8,000 |
| | | 4 | 250 |
| I | rBCG30 + r30 | 1 | 128,000 |
| | | 2 | 128,000 |
| | | 3 | 4,000 |

Ten weeks after immunization, all animals in Groups A-E were challenged with an aerosol generated from a 10 mL single-cell suspension containing $5\times10^4$ CFU of *M. tuberculosis*. (Prior to challenge, the challenge strain, *M. tuberculosis* Erdman strain [ATCC 35801], had been passaged through outbred guinea pigs to maintain virulence, cultured on 7H11 agar, subjected to gentle sonication to obtain a single cell suspension, and frozen at −70° C.). This aerosol dose delivered approximately 20 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 wk and then euthanized. The right lung and spleen of each animal was removed and cultured for CFU of *M. tuberculosis* on Middlebrook 7H11 agar for two weeks at 37° C., 5% $CO_2$-95% air atmosphere.

Figure 9:
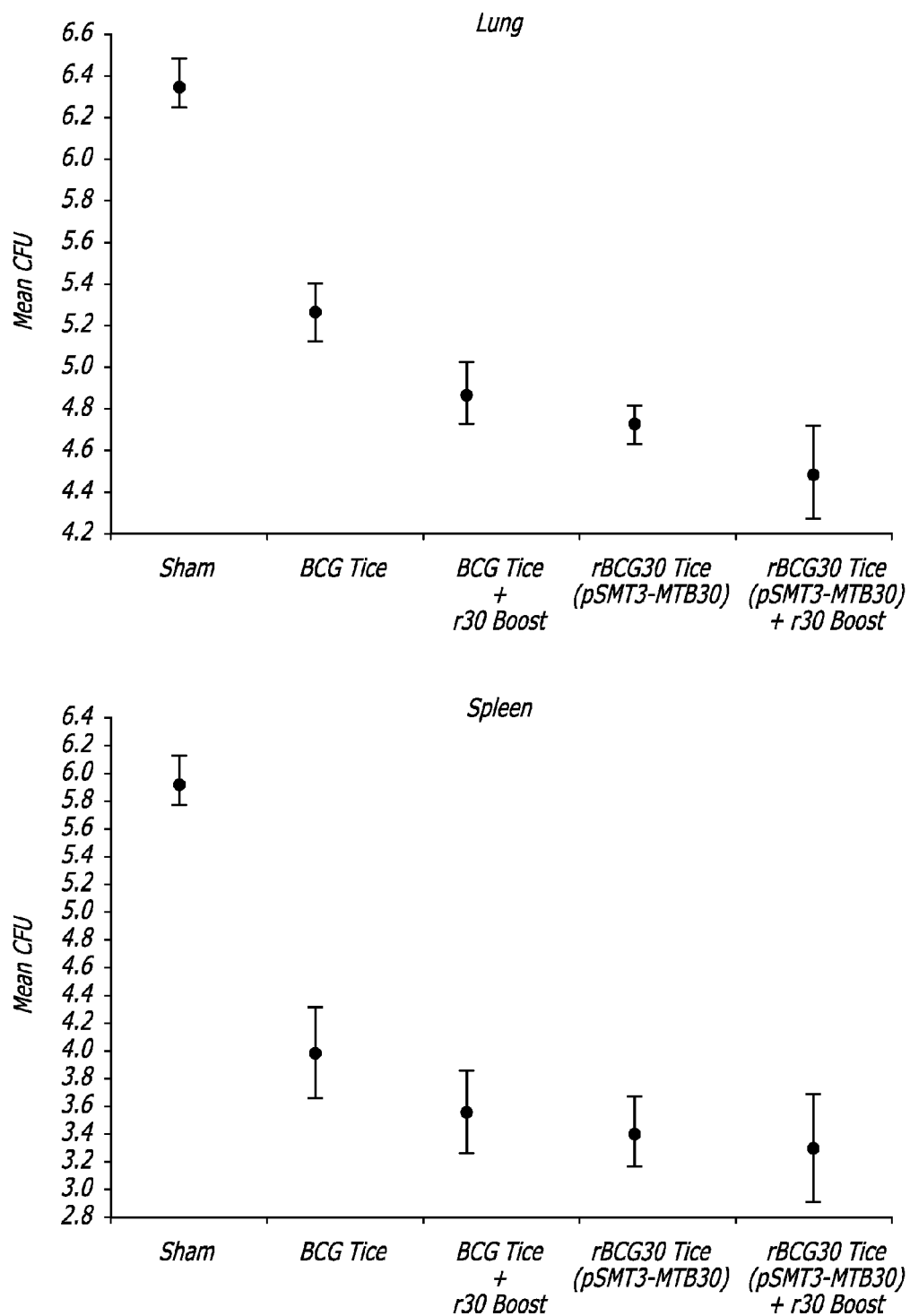
FIG. 9 graphically depicts CFU of infectious *M. tuberculosis* recovered from guinea pigs' lungs and spleens following post immunization challenge with *M. tuberculosis* in animals that were sham-immunized, immunized with BCG or rBCG30 alone, or immunized with BCG or rBCG30 as a prime and immunized with purified recombinant *M. tuberculosis* 30 kDa major extracellular protein (r30) as the boost (prime-boost).
Figure 10:
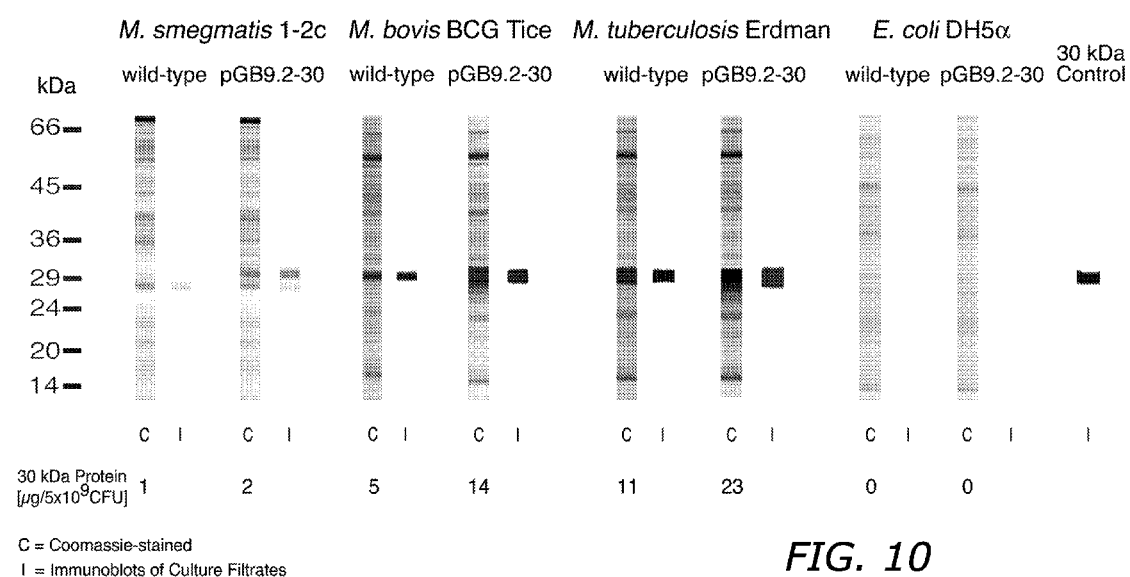
FIG. 10 depicts Coomassie blue stained gels illustrating the two-plasmid system for the expression of *M. tuberculosis* 30 kDa protein in *M. bovis* Tice.
Figure 12:
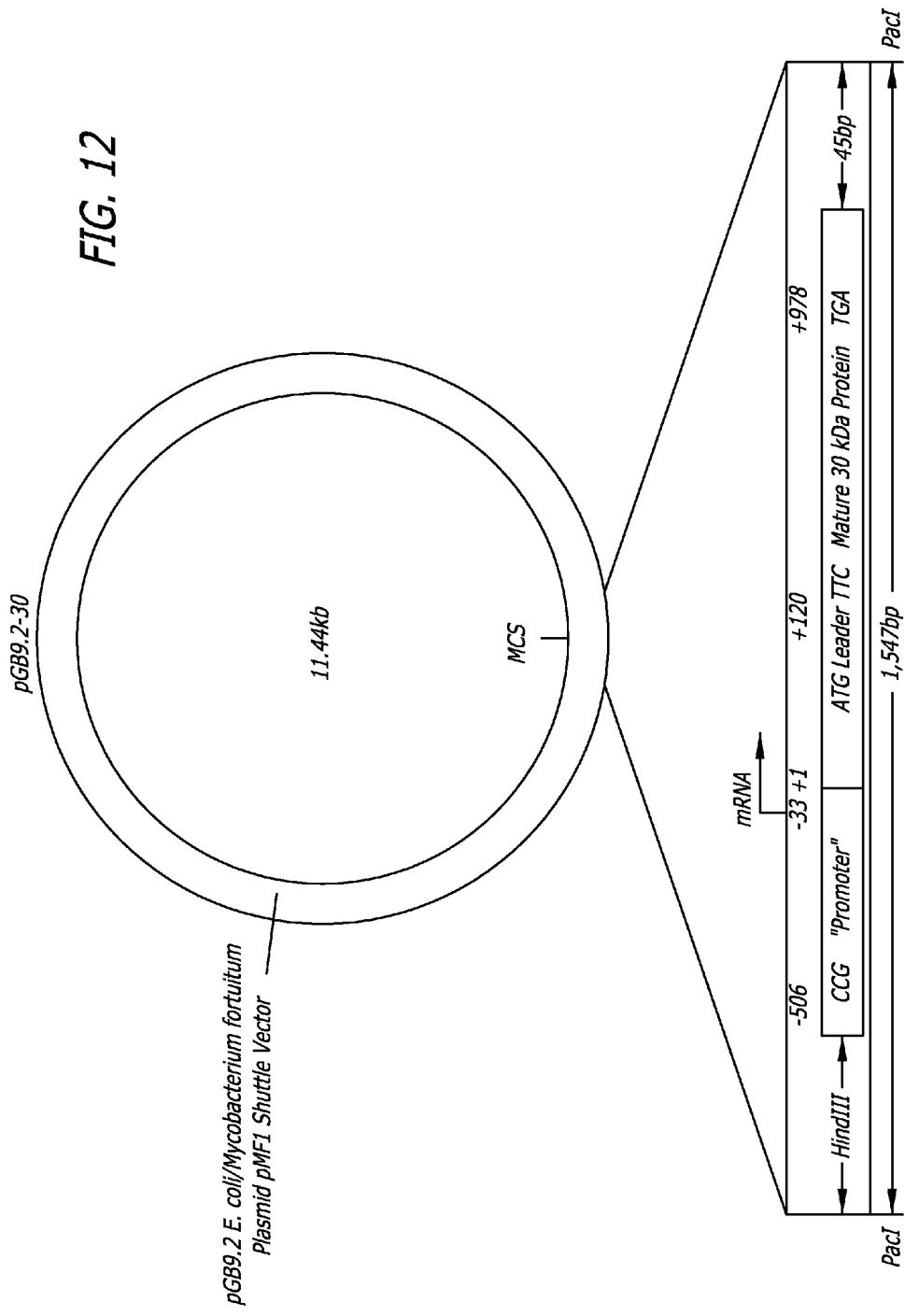
FIG. 12 depicts the pGB9.2-30 plasmid as used in accordance with the teaching of the present invention.
Figure 13:
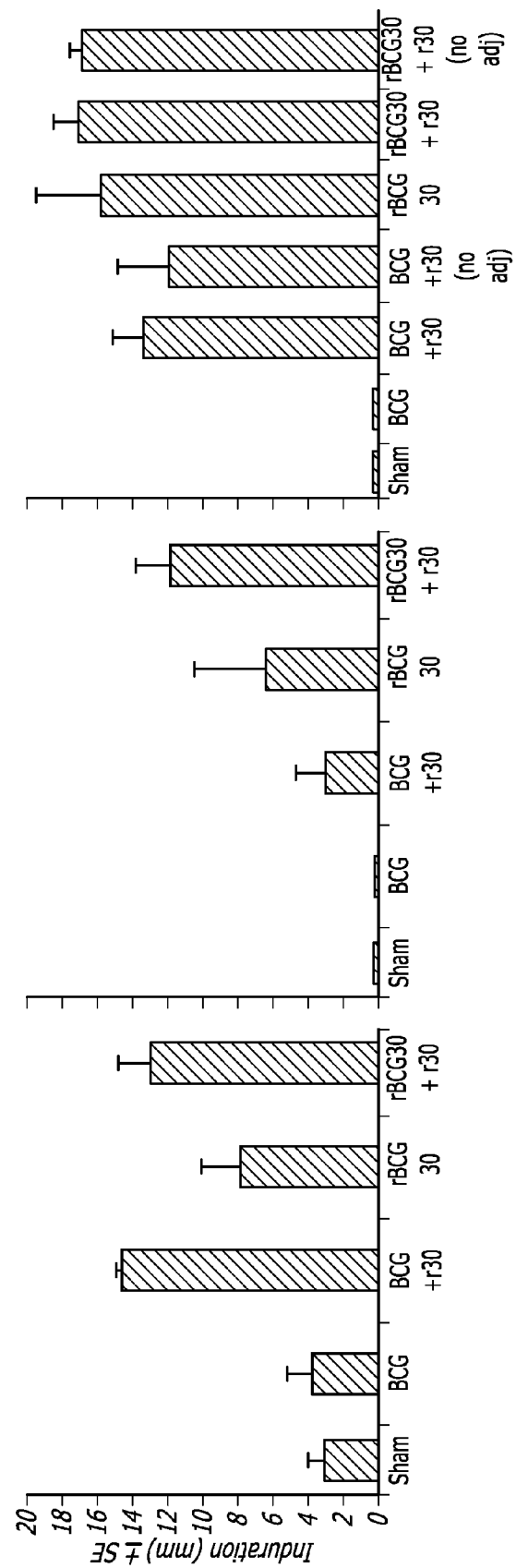
FIG. 13 graphically depicts cutaneous delayed-type hypersensitivity (DTH) of guinea pigs sham-immunized, immunized with BCG or rBCG30 alone, or immunized with BCG or rBCG30 and boosted with purified recombinant *M. tuberculosis* 30 kDa major extracellular protein (r30) as the boost (prime-boost).

The results of the assay for CFU in the lungs and spleens are shown in Table 12 and FIG. 9. These results showed that animals immunized with BCG or the recombinant BCG strain (rBCG30) with or without a protein boost had much lower CFU in the lungs and spleens than the sham immunized animals. Animals immunized with rBCG30 had fewer CFU than animals immunized with BCG as previously observed. Most importantly, animals immunized first with BCG and then with r30 had 0.41 log fewer CFU in the lungs and 0.45 log fewer CFU in the spleens than animals immunized with only BCG. Similarly, animals immunized with rBCG30+r30 had 0.25 log fewer CFU in the lungs and 0.13 log fewer CFU in the spleens than the animals immunized with only rBCG30. The most efficacious vaccine was the combination of rBCG30 and r30. These animals had 0.4 log fewer CFU in the lungs and 0.28 log fewer CFU in the spleens than animals immunized with the combination of BCG and r30, the second most efficacious vaccine.

TABLE 12

CFU in Lungs and Spleens

| Group | Strain | Lung (Mean Log CFU ± SE) | Spleen (Mean Log CFU ± SE) |
| --- | --- | --- | --- |
| A | BCG Tice | 5.26 ± 0.15 | 3.97 ± 0.32 |
| B | rBCG30 Tice I | 4.70 ± 0.09 | 3.37 ± 0.28 |
| C | BCG Tice + r30 | 4.85 ± 0.13 | 3.52 ± 0.29 |
| D | rBCG30 + r30 | 4.45 ± 0.21 | 3.24 ± 0.37 |
| E | Sham | 6.36 ± 0.10 | 5.98 ± 0.20 |

EXAMPLE 6

Specifically, Example 6 demonstrates that when the immunogens of the present invention are administered with, but not expressed in vivo by BCG, a high level of protective immunity is not achieved.

Immunization of guinea pigs with BCG plus recombinant *M. tuberculosis* 30 kDa major extracellular protein (r30) does not induce high level protection against challenge with *M. tuberculosis*.

Figure 5:
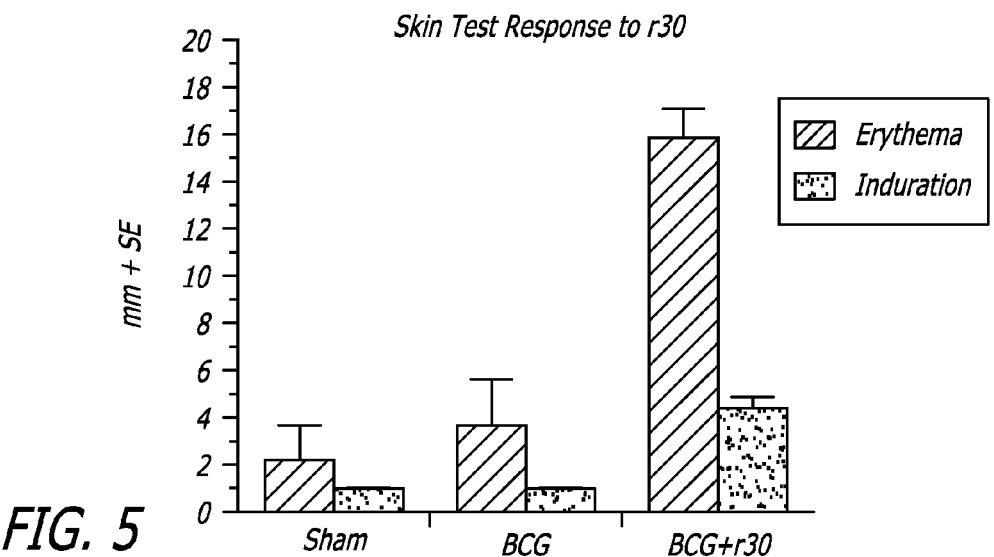
FIG. 5 graphically depicts the skin test response of guinea pigs to sham immunogenic composition, BCG alone and BCG administered with recombinant 30 kDa of *M. tuberculosis*.

Present inventors previously immunized guinea pigs with BCG plus r30 in a powerful adjuvant (SAF, Syntex Adjuvant Formulation). The r30 protein (100 mg per immunization) was administered intradermally three times. This induced a strong cutaneous delayed-type hypersensitivity (C-DTH) response to r30 (FIG. 5). Indeed, the C-DTH response was comparable to that induced by recombinant BCG expressing r30. Nevertheless, immunization with both BCG and r30 did not induce high level protection against challenge with *M. tuberculosis* (Table 13). Animals immunized with both BCG and r30 did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis*.

TABLE 13

Colony Forming Units (CFU) of *M. tuberculosis* in Lungs and Spleens of Animals Challenged by Aerosol with *M. tuberculosis* Erdman Strain: Animals Immunized with BCG or with BCG plus Recombinant *M. tuberculosis* 30 kDa Protein in Adjuvant or Sham-immunized

| | n | Lung CFU $Log_{10}$ (Mean ± SE) | Spleen CFU $Log_{10}$ (Mean ± SE) |
| --- | --- | --- | --- |
| Sham-immunized | 17 | 6.40 ± 0.18 | 5.65 ± 0.20 |
| BCG | 8 | 4.70 ± 0.13 | 2.91 ± 0.35 |
| BCG + r30 | 9 | 5.30 ± 0.23 | 3.34 ± 0.37 |

EXAMPLE 7

Example 7 demonstrates that the in vivo expression of the immunogens of the present invention using a *Mycobacterium* sp. closely related to BCG, but unable to replicate in mammalian hosts, fails to induce significant levels of protection against challenge with *M. tuberculosis*.

Immunization of guinea pigs with live recombinant *M. smegmatis* expressing the *M. tuberculosis* 30 kDa major extracellular protein (r30) in a form indistinguishable from the native form does not induce high level protection against challenge with *M. tuberculosis*.

In one of the same experiments in which present inventors immunized animals with BCG, present inventors immunized guinea pigs with live recombinant *M. smegmatis* expressing the *M. tuberculosis* 30 kDa major extracellular protein (r30) in a form indistinguishable from the native form. The expression and secretion of the *M. tuberculosis* 30 kDa major extracellular protein (r30) by *M. smegmatis* was equal to or greater than that of the recombinant BCG strain expressing and secreting the *M. tuberculosis* 30 kDa major extracellular protein. Moreover, the dose of recombinant *M. smegmatis*, $10^9$ bacteria, was very high, one million times the dose of recombinant BCG ($10^3$ bacteria), to more than compensate for the poor multiplication of *M. smegmatis* in the animal host. To compensate even further, the recombinant *M. smegmatis* was administered three times intradermally, whereas the recombinant BCG was administered only once intradermally. Immunization with recombinant *M. smegmatis* expressing the r30 protein induced a strong cutaneous delayed-type hypersensitivity (C-DTH) response to r30. Indeed, the C-DTH response was comparable to or greater than that induced by recombinant BCG expressing r30. Nevertheless, the live recombinant *M. smegmatis* expressing the *M. tuberculosis* 30 kDa major extracellular protein did not induce high level protection against challenge with *M. tuberculosis* (Table 14). Animals immunized with the live recombinant *M. smegmatis* expressing the *M. tuberculosis* 30 kDa major extracellular protein did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis*.

TABLE 14

Colony Forming Units (CFU) of *M. tuberculosis* in Lungs and Spleens of
Animals Challenged by Aerosol with *M. tuberculosis* Erdman Strain:
Animals Immunized with Live Recombinant *M. smegmatis* Expressing the
*M. tuberculosis* 30 kDa Major Extracellular Protein (r*M. smegmatis* 30)

|  | n | Lung CFU $Log_{10}$ (Mean ± SE) | Spleen CFU $Log_{10}$ (Mean ± SE) |
| --- | --- | --- | --- |
| Sham-immunized | 9 | 6.63 ± 0.27 | 6.34 ± 0.29 |
| BCG | 8 | 4.61 ± 0.14 | 4.31 ± 0.27 |
| *M. smegmatis* Control | 9 | 5.92 ± 0.31 | 5.29 ± 0.34 |
| r*M. smegmatis* 30 | 9 | 5.48 ± 0.26 | 5.55 ± 0.28 |

EXAMPLE 8

Example 8 demonstrates that the slow release of the immunogens of the present invention by synthetic immunogenic composition microcarriers also fails to induce significant levels of protection against challenge with *M. tuberculosis*.

Immunization of guinea pigs with microspheres that are of the same approximate size as BCG and like BCG slowly release the *M. tuberculosis* 30 kDa major extracellular protein (r30) over 60-90 days does not induce high level protection against challenge with *M. tuberculosis*.

In one of the same experiments in which present inventors immunized animals with rBCG30 and BCG, present inventors immunized guinea pigs with microspheres that are of the same approximate size as BCG and like BCG slowly release the *M. tuberculosis* 30 kDa major extracellular protein (r30) over 60-90 days. One set of animals was immunized once with microspheres containing 10 mg of r30. Another set of animals was immunized three times with microspheres containing 3.3 mg of r30. This amount was calculated to greatly exceed the amount of r30 protein expressed by the recombinant BCG strain. Immunization with either regimen of microspheres induced a strong cutaneous delayed-type hypersensitivity (C-DTH) response to r30. Indeed, the C-DTH response was comparable to that induced by recombinant BCG expressing r30. Nevertheless, immunization with the microspheres that are of the same approximate size as BCG and like BCG slowly release the *M. tuberculosis* 30 kDa major extracellular protein did not induce high level protection against challenge with *M. tuberculosis* (Table 15). Animals immunized with the microspheres did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis*.

TABLE 15

Colony Forming Units (CFU) of *M. tuberculosis* in Lungs and Spleens of
Animals Challenged by Aerosol with *M. tuberculosis* Erdman Strain:
Animals Immunized with Microspheres That are of the Same Approximate
Size as BCG and Like BCG Slowly Release the *M. tuberculosis* 30 kDa
Major Extracellular Protein (r30)
Animals Immunized with Liposomes That Contain the *M. tuberculosis* 30
kDa Major Extracellular Protein (r30)

|  | n | Lung CFU $Log_{10}$ (Mean ± SE) | Spleen CFU $Log_{10}$ (Mean ± SE) |
| --- | --- | --- | --- |
| Sham-immunized | 9 | 6.31 ± 0.19 | 6.20 ± 0.26 |
| BCG | 9 | 5.35 ± 0.14 | 4.81 ± 0.21 |
| rBCG30 | 9 | 4.48 ± 0.14 | 3.73 ± 0.33 |
| Control Microspheres | 9 | 6.67 ± 0.29 | 5.94 ± 0.32 |
| Microspheres with r30 (10 mg × 1) | 6 | 6.10 ± 0.32 | 5.93 ± 0.41 |
| Microspheres with r30 (3.3 mg × 3) | 9 | 6.42 ± 0.17 | 6.04 ± 0.28 |
| Control Liposomes | 9 | 6.24 ± 0.23 | 6.41 ± 0.21 |
| Liposomes with r30 | 9 | 5.77 ± 0.18 | 5.63 ± 0.16 |

EXAMPLE 9

Example 9 demonstrates that the slow release of the immunogens of the present invention by synthetic immunogenic composition microcarriers also fails to induce significant levels of protection against challenge with *M. tuberculosis*.

Immunization of guinea pigs with liposomes containing the *M. tuberculosis* 30 kDa major extracellular protein does not induce high level protection against challenge with *M. tuberculosis*.

In the same experiment as in Example 3, the present inventors immunized guinea pigs with liposomes containing the *M. tuberculosis* 30 kDa major extracellular protein. The animals were immunized three times with liposomes containing 50 mg of r30. This induced a moderately strong cutaneous delayed-type hypersensitivity (C-DTH) response to r30. The C-DTH response was greater than that induced by BCG and control liposomes but less than that induced by recombinant BCG expressing r30. Nevertheless, immunization with liposomes containing the *M. tuberculosis* 30 kDa major extracellular protein did not induce high level protection against challenge with *M. tuberculosis* (Table 15). Animals immunized with the liposomes containing the *M. tuberculosis* 30 kDa major extracellular protein did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis*.

EXAMPLE 10

Use of the Growth-Regulatable Auxotrophic Strains in Guinea Pigs

To determine if iron-loaded rBCG-mbtB could persist in guinea pigs after immunization, nine male guinea pigs (Hartley strain, 250-300 grams) were given an intradermal inoculation of approximately $5 \times 10^6$ CFU of rBCG-mbtB that had been iron-loaded by growing them in the presence of mycobactin J and iron. After three weeks (the approximate peak of in vivo growth of wild-type BCG after intradermal inoculation into guinea pigs), the animals were euthanized and the right lung and spleen were cultured for rBCG-mbtB. Colonies of rBCG-mbtB were recovered from the organs of seven of the nine animals showing that rBCG-mbtB is able to persist and/or multiply in guinea pigs over at least a three week period.

EXAMPLE 11

Use of the Growth-Regulatable Auxotrophic Strains in Humans

Example 11 provides a representative method for administering the auxotrophic embodiments of the present invention.

The growth-regulatable auxotrophic vaccines are used in humans as follows. Immunocompromised persons are immunized with the vaccines, for example the tryptophan auxotroph BCG strain. The person immediately begins supplementing his or her diet with tryptophan in sufficiently high amount so that the auxotroph multiplies at normal levels and induces a high level of protective immunity to tuberculosis. In most people, the multiplication of the recombinant BCG does not cause a health problem. The organism multiplies in the tissues to modest levels and is then cleared by the immune system. However, in some immunocompromised people, disseminated disease or other problems from bacterial multiplication develop. These people immediately stop the dietary supplement. In the absence of the dietary supplement, the auxotroph rapidly dies out and ceases to cause a health problem.

This approach is a particularly attractive one in the developing world where medical care may not be readily available. If a person has an adverse consequence from the immunization, the person does not need to access the health care system or obtain antibiotics, which may be costly and/or not readily available. The person need only stop taking the dietary supplement—a passive rather than active intervention.

EXAMPLE 12

Use of the Prototrophic Attenuated Strains

Similarly, Example 6 details the use of prototrophic attenuated strains of the present invention.

These strains are administered to immunocompromised persons in the usual way BCG vaccines are administered i.e. without any dietary supplementation.

EXAMPLE 13

The Protective Efficacy of BCG Vaccination is Enhanced by Boosting with the *M. tuberculosis* 30 kDa Major Extracellular Protein Vaccines and Challenge Strain. The live vaccines used were the parental *Mycobacterium bovis* BCG Tice (BCG) and a recombinant BCG Tice (rBCG30) over expressing the *M. tuberculosis* 30 kDa major extracellular protein. The booster vaccine used was recombinant *M. tuberculosis* 30 kDa major extracellular protein (r30), purified from culture filtrates of recombinant *Mycobacterium smegmatis* 1-2c containing plasmid pMTB30 and demonstrated to be indistinguishable from the native protein. The challenge strain was *Mycobacterium tuberculosis* Erdman strain (ATCC 35801).

Immunization of Guinea pigs. Specific-pathogen free 250-300 g outbred male Hartley strain guinea pigs from Charles River Breeding Laboratories were immunized intradermally with $10^3$ CFU of BCG or rBCG30 only or immunized first with $10^3$ CFU of BCG or rBCG30 and six weeks (Experiment 2) or seven weeks (Experiments 2 and 3) later with r30. Control animals were sham-immunized by intradermal administration of buffer (PBS). In the first two experiments, r30 was administered in Syntex Adjuvant Formulation (SAF) at a dose of 100 μg of protein in 100 μL of adjuvant. In the third experiment, each dose of 20 μg of r30 was first diluted to a final volume of 100 μL in phosphate buffered saline and then mixed with 150 μL of AS02A adjuvant (generously provided by GlaxoSmithKline Biologicals) or with no adjuvant. For studies of cutaneous delayed-type hypersensitivity (DTH), guinea pigs were immunized in groups of 6 animals each. For the simultaneously conducted studies of protective immunity, separate guinea pigs were immunized in groups of 15 animals each except for sham-immunized animals (9-15 per group) and BCG-immunized animals boosted with r30 without adjuvant in the third experiment (6 animals per group).

Cutaneous DTH. Guinea pigs were shaved over the back and injected intradermally with 10 μg of r30 in 100 μL PBS. The extent of induration was measured 24 hr later. In Experiment 1, the diameter of hard induration was measured as in previous studies by determining the area impeding the movement of a blunt instrument pushed across the skin toward the lesion from four directions. In Experiments 2 and 3, the diameter of induration was assessed by palpation and inspection in direct and oblique light, the method used to read tuberculin skin tests in humans.

In all three experiments, animals immunized with only BCG had negligible cutaneous DTH responses equivalent to sham-immunized animals (FIG. 13). Boosting BCG-immunized animals with r30 markedly increased the cutaneous DTH response by a minimum of 4-fold. As in previous studies, animals immunized with only rBCG30 had a significantly greater cutaneous DTH response than animals immunized with only BCG. Boosting rBCG30-immunized animals with r30 increased the cutaneous DTH response to r30 nearly 2-fold in Experiments 1 and 2, but not in Experiment 3 where the response in animals immunized with rBCG30 alone was very high.

Antibody Titer. Immediately after the skin test was read in the skin-tested animals described in the previous paragraph, a subset of 3-5 of the six animals were euthanized and their serum assayed for antibody titer to r30 by ELISA.

In all three experiments, animals immunized with only BCG had baseline reciprocal antibody titers equivalent to that previously measured in unimmunized animals. In Experiment 3, where a sham-immunized group was studied within the same experiment, titers for animals immunized with only BCG were not significantly different from titers for sham-immunized animals—both were negligible. Boosting BCG-immunized animals with r30 markedly increased the antibody response; in the three experiments, the geometric mean reciprocal antibody titer was increased by 27-fold to 147-fold. Animals immunized with only rBCG30 had significantly higher antibody titers than animals immunized with only BCG. In the three experiments, geometric mean titers (Table 16) for rBCG30-immunized animals were 2-fold to 32-fold higher than for BCG-immunized animals. Boosting rBCG30 with r30 also significantly increased antibody titers by 61-fold to 167-fold in the three experiments. Boosting with r30 in the absence of adjuvant lowered the mean geometric titer by more than 2-fold in both BCG- and rBCG30-immunized animals.

TABLE 16 r30 Antibody Titers

|  | Group | N | Geometric Mean Antibody Titer |
|---|---|---|---|
| Experiment 1 | BCG | 4 | 125 |
|  | BCG + r30 | 4 | 3,363 |
|  | rBCG30 | 4 | 250 |
|  | rBCG30 + r30 | 3 | 40,317 |
| Experiment 2 | BCG | 5 | 189 |
|  | BCG + r30 | 5 | 27,858 |
|  | rBCG30 | 5 | 1,741 |
|  | rBCG30 + r30 | 4 | 107,635 |
| Experiment 3 | Sham | 4 | 125 |
|  | BCG | 5 | 165 |
|  | BCG + r30 | 5 | 24,252 |
|  | BCG + r30 No Adj | 4 | 9,514 |
|  | rBCG30 | 5 | 5,278 |
|  | rBCG30 + r30 | 4 | 362,039 |
|  | rBCG30 + r30 No Adj | 5 | 147,033 |

Protective Immunity to Aerosol Challenge. Ten weeks after the first immunization (if the animals were boosted) or only immunization (if the animals were not boosted), the guinea pigs were challenged with an aerosol generated from a 7.5 mL single cell suspension containing a total of $7.\times10^4$ CFU of M. tuberculosis* using a Collison 6-jet nebulizer at a pressure of 20 psi; this dose delivered ~10 live bacteria to the lungs of each animal, based on counting primary lesions in the lungs of animals euthanized three weeks after exposure to this dose. Afterwards, guinea pigs were individually housed in stainless steel cages contained within a laminar flow biohazard safety enclosure and allowed free access to standard laboratory food and water. The animals were observed for illness and weighed weekly for 10 weeks and then euthanized. The lungs, spleen, and liver of each animal were removed aseptically and inspected immediately for pathology, and the right lung and spleen were cultured for CFU of *M. tuberculosis.*

In all three experiments, all immunized animals gained weight normally after challenge, i.e. there was no significant difference in weight gain among the different immunized groups after challenge or between immunized animals and uninfected controls. In contrast, sham-immunized animals failed to gain weight normally after challenge, most noticeably in Experiment 1, where this group of animals lost weight beginning two weeks after challenge, a time typically coinciding with dissemination of *M. tuberculosis* from the initial site of infection in the lung. In Experiments 2 and 3, weight gain in sham-immunized animals lagged that in immunized animals.

Sham-immunized animals had a very high burden of *M. tuberculosis* in their lungs and spleens (FIG. 14). Compared with sham-immunized animals, BCG-immunized animals had a markedly lower organ burden. Most importantly, in all three experiments, boosting BCG-immunized animals with r30 resulted in a substantial further reduction in the lung and spleen burden. Animals immunized with only rBCG30 had lower organ burdens of *M. tuberculosis* than animals immunized with only BCG. Remarkably, animals immunized with only rBCG30 also had fewer CFU in their organs than animals immunized with BCG and boosted.

Boosting animals immunized with rBCG30 had little impact on organ burden. In the lungs there was essentially no difference in CFU between boosted and non-boosted animals immunized with rBCG30. Whether animals were boosted with r30 in the presence or absence of adjuvant had no significant impact on organ burden in either BCG or rBCG30-immunized animals in Experiment 3, the only experiment in which this comparison was made.

The immunogenic compositions of the present invention represent an entirely new approach to the induction of immune responses against intracellular pathogens. Through a series of well designed experiments and thoughtful analysis, the present inventors have thoroughly demonstrated that protective immunity is only achieved when a precisely selected intracellular pathogen, or closely related species, is transformed to express recombinant extracellular proteins of the same or different intracellular pathogen in accordance with the teachings of the present invention.

The present invention can also be used to provide diagnostic, prophylactic and therapeutic benefits against multiple intracellular pathogens simultaneously. For example a recombinant attenuated intracellular immunogenic composition like *M. bovis* BCG can be designed to expressed immunoprotective immunogens against *M. tuberculosis* and *Legionella* sp. simultaneously. Consequently, great efficiencies in delivering immunogenic compositions could be accomplished. The non-limiting examples of recombinant BCG expressing the major extracellular proteins of *M. tuberculosis* not only serve as a fully enabling embodiment of the present invention, but represent a significant advance to medicine, and humanity as a whole.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

ADDITIONAL REFERENCES HEREIN
INCORPORATED BY REFERENCE

Anderson D H, Harth G, Horwitz M A and Eisenberg D. 2001. An interfacial mechanism and a class of inhibitors inferred from two crystal structures of the *Mycobacterium tuberculosis* 30 kDa major secretory protein (antigen 85B), a mycolyl transferase. J Mol Biol 307, 671-81.

Belisle J T, Vissa V D, Sievert T, Takayama K, Brennan P J and Besra G S. 1997. Role of the major antigen of *Mycobacterium tuberculosis* in cell wall biogenesis. Science 276, 1420-2.

Cohn D L, Bustreo F, Raviglione M C and the International Union against Tuberculosis and Lung Disease 1997. Drug-resistant tuberculosis: review of the worldwide situation and the WHO/IUATLD Global Surveillance Project. Clin Infect Dis 24(Suppl. 1), S121-S130.

Colditz G A, Brewer T F, Berkey C S, Wilson M E, Burdick E, Fineberg H V, and Mosteller F. 1994. Efficacy of BCG vaccine in the prevention of tuberculosis. Meta-analysis of the published literature. JAMA 271:698-702.

Fine P E M. 1989. The BCG story: Lessons from the past and implications for the future. Rev. Infect. Dis. 11 (Suppl. 2):S353-S359.

Gobin J and Horwitz M A. 1996. Exochelins of *Mycobacterium tuberculosis* remove iron from human iron-binding proteins and donate iron to mycobactins in the *M. tuberculosis* cell wall. J. Exp. Med. 183:1527-32.

Harth G and Horwitz M A. 1999. Export of recombinant *Mycobacterium tuberculosis* superoxide dismutase is dependent upon both information in the protein and mycobacterial export machinery. A model for studying export of leaderless proteins by pathogenic mycobacteria. J. Biol. Chem. 274: 4281-92.

Harth G, Horwitz M A, Tabatadze D and Zamecnik P C. 2002. Targeting the *Mycobacterium tuberculosis* 30/32-kDa mycolyl transferase complex as a therapeutic strategy against tuberculosis: proof of principle by using antisense technology. Proc Natl Acad Sci USA 99:15614-9.

Harth G, Lee B-Y, Wang J, Clemens D L and Horwitz M A. 1996. Novel insights into the genetics, biochemistry, and immunocytochemistry of the 30-kilodalton major extracellular protein of *Mycobacterium tuberculosis*. Infect Immun 64:3038-47.

Harth G, Zamecnik P C, Tang J-Y, Tabatadze D and Horwitz M A. 2000. Treatment of *Mycobacterium tuberculosis* with antisense oligonucleotides to glutamine synthetase mRNA inhibits glutamine synthetase activity, formation of the poly-L-glutamine/glutamate cell wall structure, and bacterial replication. Proc Natl Acad Sci USA 97:418-23.

Jungblut P R, Schaible U E, Mollenkopf H J, Zimny-Arndt U, Raupach B, Mattow J, Halada P, Lamer S, Hagens K and Kaufmann S H. 1999. Comparative proteome analysis of *Mycobacterium tuberculosis* and *Mycobacterium bovis* BCG strains: towards functional genomics of microbial pathogens. Mol Microbiol 33:1103-17.

Kaps I, Ehrt S, Seeber S, Schnappinger D, Martin C, Riley L W and Niederweis M. 2001. Energy transfer between fluorescent proteins using a co-expression system in *Mycobacterium smegmatis*. Gene 278:115-24.

Lee B-Y and Horwitz M A. 1995. Identification of macrophage and stress-induced proteins of *Mycobacterium tuberculosis*. J Clin Invest 96:245-9.

Murray P J, Aldovini A, and Young R A. 1996. Manipulation and potentiation of antimycobacterial immunity using recombinant bacille Calmette-Guerin strains that secrete cytokines. Proc. Natl. Acad. Sci. USA 93:934-9.

Pablos-Mendez A, Raviglione M C, Laszlo A, Binkin N, Rieder H L, Bustreo F, Cohn D L, Lambregts-van Weezenbeck C S B, Kim S J, Chaulet P, Nunn P and the World Health Organization-International Union against Tuberculosis and Lung Disease Working Group on Anti-Tuberculosis Drug Resistance Surveillance 1998. Global surveillance for antituberculosis-drug resistance, 1994-1997. N Engl J Med 338: 1641-9.

Rose J D, Maddry J A, Comber R N, Suling W J, Wilson L N and Reynolds R C. 2002. Synthesis and biological evaluation of trehalose analogs as potential inhibitors of mycobacterial cell wall biosynthesis. Carbohyd Res 337:105-20.

Taylor J L, Turner O C, Basaraba R J, Belisle J T, Huygen K and Orme I M. 2003. Pulmonary necrosis resulting from DNA vaccination against tuberculosis. Infect. Immun. 71:2192-8.

Turner J, Rhoades E R, Keen M, Belisle J T, Frank A A and Orme I A. 2000. Effective preexposure tuberculosis vaccines fail to protect when they are given in an immunotherapeutic mode. Infect. Immun. 68:1706-9.

What is claimed is:

1. An immunogenic composition comprising:
a growth regulatable recombinant Bacille Calmette-Guerin (rBCG) having a first extrachromosomal nucleic acid sequence comprising a gene encoding for a first *Mycobacteria* major extracellular protein selected from the group consisting of 30 kDa protein, 23.5 kDa protein, 32A kDa protein and combinations thereof;
wherein said *Mycobacteria* major extracellular proteins are over expressed and secreted and said growth regulatable rBCG is selected from the group consisting of auxotrophs and metabolically impaired mutants and combinations thereof.

2. The immunogenic composition according to claim 1 further comprising a second extrachromosomal nucleic acid sequence comprising a gene encoding for a second *Mycobacteria* major extracellular protein selected from the group consisting of 30 kDa, protein 23.5 kDa protein, 32A kDa protein and combinations thereof.

3. The immunogenic composition according to claim 2 wherein at least one of said first extrachromosomal nucleic acid sequence and second extrachromosomal nucleic acid sequence is under the control of a promoter that is not a heat shock promoter or a stress protein promoter.

4. The immunogenic composition according to claim 2 wherein at least one of said major extracellular proteins are non-fusion proteins.

5. The immunogenic composition according to claim 2 wherein said first or said second *Mycobacteria* major extracellular protein is from a species of *Mycobacterium* selected from the group consisting of *Mycobacterium tuberculosis* (Mtb), *Mycobacterium bovis* (MB), and *Mycobacterium leprae* (ML).

6. The immunogenic composition according to claim 4 wherein said extracellular non-fusion proteins are over expressed and secreted such that a protective immune response is induced in a host.

7. The immunogenic composition according to claim 1 wherein said metabolically impaired mutant is a siderophore mutant.

8. The immunogenic composition according to claim 7 wherein said siderophore is a mycobactin or an exochelin.

9. The immunogenic composition according to claim 1 wherein said growth regulatable rBCG is an auxotroph and wherein tryptophan, glutamine or pantothenic acid is used to regulate growth of said auxotroph.

* * * * *

UNITED STATES PATENT AND TRADEMARK OFFICE
CERTIFICATE OF CORRECTION

PATENT NO.       : 8,124,068 B2
APPLICATION NO.  : 12/581795
DATED            : February 28, 2012
INVENTOR(S)      : Marcus A. Horwitz, Gunter Harth and Michael V. Tullius It is certified that error appears in the above-identified patent and that said Letters Patent is hereby corrected as shown below:

Column 1, lines 21-22, "A131338 awarded by the Department of Health and Human Services" should read --AI031338 awarded by the National Institutes of Health--.

Signed and Sealed this
Twenty-second Day of May, 2012

David J. Kappos
*Director of the United States Patent and Trademark Office*